(12) United States Patent
Rychnovsky et al.

(10) Patent No.: US 9,222,943 B2
(45) Date of Patent: Dec. 29, 2015

(54) MASS SPECTROMETRY-CLEAVABLE CROSS-LINKING AGENTS TO FACILITATE STRUCTURAL ANALYSIS OF PROTEINS AND PROTEIN COMPLEXES, AND METHOD OF USING SAME

(75) Inventors: Scott Rychnovsky, Irvine, CA (US); Lan Huang, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 806 days.

(21) Appl. No.: 13/471,365

(22) Filed: May 14, 2012

(65) Prior Publication Data
US 2013/0144541 A1 Jun. 6, 2013

Related U.S. Application Data

(60) Provisional application No. 61/486,260, filed on May 14, 2011.

(51) Int. Cl.

| | | |
|---|---|---|
| G01N 33/48 | (2006.01) | |
| G01N 31/00 | (2006.01) | |
| G01N 33/50 | (2006.01) | |
| G01N 33/68 | (2006.01) | |
| H01J 49/00 | (2006.01) | |
| G06F 19/00 | (2011.01) | |
| G06F 19/24 | (2011.01) | |
| G06F 19/12 | (2011.01) | |
| G06F 19/26 | (2011.01) | |
| G06F 19/16 | (2011.01) | |
| C07D 207/46 | (2006.01) | |

(52) U.S. Cl.
CPC .......... *G01N 33/6848* (2013.01); *C07D 207/46* (2013.01); *G06F 19/12* (2013.01); *G06F 19/16* (2013.01); *G06F 19/24* (2013.01); *G06F 19/26* (2013.01); *G06F 19/705* (2013.01); *G06F 19/706* (2013.01); *H01J 49/0036* (2013.01)

(58) Field of Classification Search
None
See application file for complete search history.

(56) References Cited

PUBLICATIONS

Lai et al. avb Integrins play an essential role in BMP-2 induction of osteoplast differentiation. Journal of Bone and Mineral Research, vol. 20, 2005, pp. 330-340.*
Kao et al. Development of a novel cross-linking strategy for fast and accurate identification of cross-linked peptides of protein complexes. Molecular & Cellular Proteomics, vol. 10.1, 17 pages, published Aug. 24, 2010.*
Back, J.W., et al.; A New Crosslinker for Mass Spectrometric Analysis of the Quaternary Structure of Protein Complexes; J Am Soc Mass Spectrom, 2001, 12, 222-227.

Back, Jaap Willem, et al.; Chemical Cross-linking and Mass Spectrometry for Protein Structual Modeling; J. Mol. Biol., (2003), 331, 303-313.
Chen, Zhuo Angel, et al.; Architecture of the RNA polymerase II-TFIIF complex revealed by cross-linking and mass spectromerty; The EMBO Journal, vol. 29, No. 4, 2010.
Chowdhury, Saiful M., et al.; Identification of Cross-Linked Peptides after Click-Based Enrichment Using Sequential Collision-Induced Dissociation and Electron Transfer Dissociation Tandem Mass Spectrometry; Analyticl Chemistry, vol. 81, No. 13, Jul. 1, 2009.
Chu, Feixia, et al.; Isotope-Coded and Affinity-Tagged Cross-Linking (ICATXL): An Efficient Strategy to Probe Protein Interaction Surfaces; J. Am. Chem. Soc. , vol. 128, No. 32, 2006.
Chu, Feixia, et al.; Finding Chimeras: a Bioinformatics Strategy for Identification of Cross-linked peptides; Molecular & Cellular Proteomics, 9, 25-31, 2010.
Collins, Christopher J., et al.; Isotopically Labeled Crosslinking Reagents: Resolution of Mass Degeneracy in the Identification of Crosslinked peptides; Bioorg. Med. Chem., Lett. 13, (2003), 4023-4026.
Denison, Carilee, et al.; Toward a General Chemical Method for Rapidly Mapping Multi-Protein Complexes; Journal of Proteome Research, 2004, 3, 417-425.
Dihazi, Gary H., et al.; Mapping low-resolution three-dimensional protein structures using chemical cross-linking and Fourier transform ion-cyclotron resonance mass spectrometry; Rapid Comm. Mass Spectrom, 2003, 17, 2005-0214.
Gao, Qiuxia, et al.; Minimize the Detection of False Positives by the Software Program DetectShift for O-Labeled Cross-Linked Peptide Analysis; Eur J Mass Spectrom (Chichester, Eng), 2008, 14(5), 275-280.
Gardner, Myles W., et al.; Chromogenic Cross-Linker for the Characterization of Protein Structure by Infrared Multiphoton Dissociation Mass Spectrometry; Analytical Chemistry, vol. 80, No. 13, Jul. 1, 2008.

(Continued)

*Primary Examiner* — Russell S Negin
(74) *Attorney, Agent, or Firm* — Knobbe, Martens, Olson & Bear, LLP

(57) ABSTRACT

Novel cross-linking compounds that can be used in mass spectrometry, tandem mass spectrometry, and multi-stage tandem mass spectrometry to facilitate structural analysis of proteins and protein complexes are provided and have the formula:

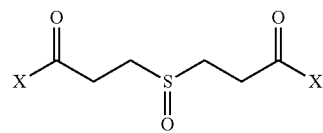

where X is an N-hydroxy-succinimidyl or similar heterocyclic group. Also provided is a method of mapping protein-protein interactions of protein complexes using various mass spectrometry techniques.

10 Claims, 106 Drawing Sheets

(56) References Cited

PUBLICATIONS

Guerrero, Cortnie, et al.; An Integrated Mass Spectrometry-based Proteomic Approach; Molecular & Cellular Proteomics, 5, 366-378, 2006.

Guerrero, Cortnie, et al.; Characterization of the proteasome interaction network using a QTAX-based tag-team strategy and protein interaction network analysis; PNAS, Sep. 9, 2008, vol. 105, No. 36.

Guo, Xin, et al.; Partial Acetylation of Lysine Residues Improves Intraprotein Cross-Linking; Analytical Chemistry, vol. 80, No. 4, Feb. 15, 2008.

Kaake, Robyn M., et al.; Characterization of Cell Cycle Specific Protein Interaction Networks of the Yeast 26S Proteasome Complex by the QTAX Strategy; J. Proteome Res., Apr. 5, 2010, 9(4), 2016-2029.

Kasper, Piotr T., et al.; An Aptly Positioned Azido Group in the Spacer of a Protein Cross-Linker for Facile Mapping of Lysines in Close Proximity; ChemBioChem, 2007, 8, 1281-1292.

Kruppa, Gary H., et al.; A topdown approach to protein structural studies using chemical cross-linking and Fourier transform mass spectrometry; Rapid Commun. Mass Spectrom, 2003, 17, 155-162.

Lee, Young Jin, et al.; Shotgun Cross-Linking Analysis for Studying Quaternary and Tertiary Protein Structures; Journal of Proteome Research, 2007, 6, 3908-3917.

Leggett, David S., et al.; Multiple Associated Proteins Regulate Proteasome Structure and Function; Molecular Cell, vol. 10, 495-507, Sep. 2002.

Leitner, Alexander, et al.; Probing Native Protein Structures by Chemical Cross-Linking, Mass Spectrometry, and Bioinformatics; Molecular & Cellular Proteomics, 9, 1634-1649, 2010.

Lu, Yali, et al.; Ionic Reagent for Controlling the Gas-Phase Fragmentation Reactions of Cross-Linked Peptides; Analytical Chemistry, vol. 80, No. 23, Dec. 1, 2008.

Maiolica, Alessio, et al.; Structual Analysis of Multiprotein Complexes by Cross-linking, Mass Spectrometry, and Database Searching; MCP Papers in Press, Oct. 5, 2007.

Mirkin, Nurit, et al.; High resolution X-ray crystallographic structure of bovine heart cytochrome c and its application to the design of an electron transfer biosensor; Proteins 2008; 70-83-92, 2007, Wiley-Liss, Inc.

Nadeau, Owen W., et al.; CrossSearch, a User-friendly Search Engine for Detecting Chemically Cross-linked Peptides in Conjugated Proteins; MCP Papers in Press, Feb. 16, 2008.

Nessen, Mere A., et al.; Selective Enrichment of Azide-Containing Peptides from Complex Mixtures;Journal of Proteome Research 2009, 8, 3702-3711.

Pearson, Kara M., et al.; Intramolecular cross-linking experiments on cytochrome c and ribonuclease A using an isotope multiplet method; Raipd Commun. Mass Spectrom, 2002, 16: 149-159.

Petrotchenko, Evgeniy V., et al.; ICC-CLASS: isotopically-coded cleavable crosslinking analysis software suite; Petrotchenki and Borchers MNC Bioinformatics 2010, 11:64.

Petrotchenko, Evgeniy V., et al.; Isotopically Coded Cleavable Crosslinker for Studying Protein-Protein Interaction and Protein Complexes; Molecular & Cellular Proteomics, 4,1167-1179, 2005.

Pettersen, Eric F., et al.; UCSF Chimera-A Visualization System for Exploratory Research and Analysis; 2004 Wiley Periodicals, Inc. J Comput Chem, 25, 1605-1612, 2004.

Pickart, Cecile M., et al.; Proteasomes and Their Kin: Proteases in the Machine Age; Molecular Cell Biology, vol. 5, Mar. 2004.

Rappsilber, Juri, et al.; A Generic Strategy to Analyze the Spatial Organization of Multi-Protein Complexes by Cross-Linking and Mass Spectrometry; Analytical Chemistry, vol. 72, No. 2, Jan. 15, 2000.

Reid, Gavin E., et al.; Statistical and Mechanistic Approaches to Understanding the Gas-Phase Fragmentation Behavior of Methionine Sulfoxide Containing Peptides; Journal of Proteome Research 2004, 3, 751-759.

Rinner, Oliver, et al.; Identification of cross-linked peptides from large sequence databases; Nature Methods, vol. 5, No. 4, Apr. 2008.

Schilling, Birgit, et al.; MS2Assign, Automated Assignment and Nomenclature of Tandem Mass Spectra of Chemically Crosslinked Peptides; Am Soc Mass Spectrom, 2003, 14, 834-850.

Singh, Pragya, et al.; Characterization of Protein Cross-Links via Mass Spectrometry and an Open-Modification Search Strategy; Anaytical Chemistry, vol. 80, No. 22, Nov. 15, 2008.

Sinz, Andrea; Chemical cross-linking and mass spectrometry for mapping three-dimensional structures of proteins and protein complexes; J. Mass Spectrom., 2003, 38, 1225-1237.

Sinz, Andrea; Chemical Cross-Linking and Mass Spectrometry to Map Three-Dimensional Protein structures and Protein-Protein interactions; Mass Spectrometry Reviews, 2006, 25, 663-682.

Sinz, Andrea; Investigation of protein-protein interactions in living cells by chemical cross-linking and mass spectrometry; Anal Bioanal Chem, (2010), 397, 3433-3440.

Sinz, Andrea, et al.; Mapping spatial proximities of sulfhydryl groups in proteins using a flurorogenic cross-linker and mass spectrometry; Analytical Biochemistry, 331, (2004), 27-32.

Soderblom, Erik J., et al.; Collision-Induced Dissociative Chemical Cross-Linking Reagents and Methodology; Applications to Protein Structual Characterization Using Tandem Mass Spectrometry Analysis; Anal. Chem., 2006, 78, 8059-8068.

Soderblom, Erik J., et al.; Tandem mass spectrometry acquisition approaches to enhance identification of protein-protein interactions using low-energy collision-induced dissociative chemical crosslinking reagents; Rapid Comm. Mass Spectrom, 2007, 21, 3395-3408.

Tagwerker, Christian, et al.; A Tandem Affinity Tag for Two-step Purification under Fully Denaturing Conditions; Molecular & Cellular Proteomics, 5, 737-748, 2006.

Tang, Xiaoting, et al.; Mass Spectrometry Identfiable Cross-Linking Strategy for Studying Protein-Protein Interactions; Analytical Chemistry, vol. 77, No. 1, Jan. 1, 2005.

Trester-Zedlitz, Michelle, et al.; A Modular Cross-Linking Approach for Exploring Protein Interactions; J. Am. Chem. Soc., 2003, 125, 2416-2425.

Vasilescu, Julian, et al.; Identification of protein-protein interactions using in vivo cross-linking and mass spectrometry; Proteomics, 2004, 4, 3845-3854.

Vellucci, Danielle, et al.; Selective Enrichment and Identification of Azide-tagged Cross-Linked Peptides Using Chemical Ligation and Mass Spectrometry; J Am Soc Mass Spectrom, 2010, 21, 1432-1445.

Yang, Li, et al.; A Photocleavable and Mass Spectrometry Identifiable Cross-Linker for Protein Interaction Studies; Analytical Chemistry, vol. 82, No. 9, May 1, 2010.

Zhang, Haizhen, et al.; Identification of Protein-Protein Ineractions and Topologies in Living Cells with Chemical Cross-linking and Mass Spectrometry; Molecular & Cellular Protemics, 8, 409-420, 2009.

* cited by examiner

Compound 1

General Structure 2

Compound 3    X =

Compound 4    X =

Compound 5    X =

Compound 6    X =

Compound 7    X =    Where R is any organic group

Compound 8    X =

Compound 9    X =

| | | | |
|---|---|---|---|
| 687.115 | b-H2O,6,+1 | -0.22 | |
| 705.192 | b,6,+1 | -0.15 | |
| 789.537 | y,6,+1 | 0.05 | |
| 800.144 | b-H2O,7,+1 | -0.27 | |
| 818.321 | b,7,+1 | -0.11 | |
| 902.486 | y,7,+1 | -0.085 | |
| 982.046 | b-H2O,8,+1 | -0.48 | |
| 1000.27 | b,8,+1 | -0.26 | |
| | y-NH3,8,+1 | -0.3 | |
| | y-H2O,8,+1 | 0.68 | |

| Type | Peptide Sequence | AA Location | Mod. Position | MS/MS m/z (Observed) | z |
|---|---|---|---|---|---|
| 2 | Ac-GDVEKGKK | G1-K8 | K$_A$7 | | 2 |
| | KK | K87-K88 | K87* | 478.76 | 2 |

FIG. 11A CONTINUED

| | | | |
|---|---|---|---|
| 371.743 | y,6,+2 | 0.016 | |
| 424.952 | b-H2O,5,+1 | -0.21 | |
| 443.242 | b,5,+1 | 0.065 | |
| 469.699 | MH-H2O,,+2 | -0.052 | |
| | MH-NH3,,+2 | -0.54 | |
| 514.326 | y,4,+1 | -0.0088 | |
| 625.2 | b,6,+1 | -0.083 | |
| | y-H2O,5,+1 | -0.17 | |
| 643.363 | y,5,+1 | -0.014 | |
| 681.997 | b,7,+1 | -0.31 | |
| 742.194 | y,6,+1 | -0.25 | |

| Type | Peptide Sequence | AA Location | Mod. Position | MS/MS m/z (Observed) | z |
|---|---|---|---|---|---|
| 2 | Ac-GDVEKGKK | G1-K8 | K$_A$7 | 478.76 | 2 |
| | KKGER | K87-K91 | K$_T$87 | 352.18 | 2 |

FIG. 11A CONTINUED

| | | |
|---|---|---|
| 510.1 | b-H2O,4,+1 | 0.18 |
| 525.843 | b,4,+1 | -0.11 |
| 534.51 | y-NH3,10,+2 | 0.065 |
| 549.337 | y,10,+2 | 0.22 |
| 576.299 | y,5,+1 | 0.023 |
| | y-NH3,11,+2 | -0.0024 |
| | y-H2O,11,+2 | 0.49 |
| 585.057 | y,11,+2 | 0.24 |
| 683.056 | y-H2O,12,+2 | 0.21 |
| | y-NH3,12,+2 | -0.28 |
| 686.331 | y,6,+1 | -0.042 |
| 692.113 | y,12,+2 | 0.26 |
| 721.125 | b,6,+1 | -0.18 |
| 751.37 | MH-H2O,,+2 | -0.0077 |
| | MH-NH3,,+2 | -0.5 |
| 799.474 | y,7,+1 | 0.017 |
| 816.316 | b-H2O,7,+1 | -0.066 |
| 834.345 | b,7,+1 | -0.048 |
| 953.557 | b-H2O,8,+1 | 0.12 |
| 971.289 | b,8,+1 | -0.16 |
| 1010.51 | y,9,+1 | -0.043 |
| | b-H2O,9,+1 | 0.048 |
| 1067.53 | y,10,+1 | -0.044 |
| 1141.4 | b,10,+1 | -0.16 |
| 1150.59 | y-H2O,11,+1 | -0.022 |
| 1168.55 | y,11,+1 | -0.072 |
| 1288.59 | b,11,+1 | -0.036 |

FIG. 11A CONTINUED

| | | |
|---|---|---|
| 414.862 | a,3,+1 | -0.41 |
| 443.2 | b,3,+1 | -0.065 |
| 504.243 | y-NH3,4,+1 | -0.039 |
| 514.026 | a,4,+1 | -0.31 |
| 521.26 | y,4,+1 | -0.048 |
| 542.101 | b,4,+1 | -0.23 |
| 634.367 | y,5,+1 | -0.025 |
| 653.135 | b-NH3,5,+1 | -0.23 |
| 670.314 | b,5,+1 | -0.078 |

FIG. 11A CONTINUED

| | | |
|---|---|---|
| 268.216 | a,4,+2 | 0.4 |
| 275.275 | a,2,+1 | 0.014 |
| 279.294 | y,2,+1 | 0.1 |
| 296.088 | b-NH3,2,+1 | 0.12 |
| 374.252 | b,2,+1 | -0.11 |
| 399.785 | y,3,+1 | 0.012 |
| 415.258 | MH-NH3,,+2 | -0.45 |
| 426.146 | a,3,+1 | -0.012 |
| 443.211 | b-NH3,3,+1 | -0.093 |
| 504.453 | b,3,+1 | -0.054 |
| 514.293 | y-NH3,4,+1 | 0.17 |
| 521.26 | a,4,+1 | -0.046 |
| 542.195 | y,4,+1 | -0.048 |
| 634.314 | b,4,+1 | -0.14 |
| 670.131 | y,5,+1 | -0.078 |
| | b,5,+1 | -0.26 |

FIG. 11A CONTINUED

|  |  |  |  |  |  |  |
|---|---|---|---|---|---|---|
| 841.274 | b,8,+1 | -0.15 |  |  |  |  |
| 928.312 | y-NH3,8,+1 | -0.093 |  |  |  |  |
|  | b,9,+1 | -0.14 |  |  |  |  |
| 945.191 | y,8,+1 | -0.24 |  |  |  |  |
| 1002.39 | y,9,+1 | -0.063 |  |  |  |  |
| 1074.45 | b-NH3,10,+1 | -0.039 |  |  |  |  |
| 1082.47 | y-NH3,10,+1 | -0.0089 |  |  |  |  |
| 1099.38 | y,10,+1 | -0.13 |  |  |  |  |
| 1170.35 | y,11,+1 | -0.19 |  |  |  |  |
| 1192.38 | b,11,+1 | -0.18 |  |  |  |  |
| 1298.4 | y,12,+1 | -0.2 |  |  |  |  |
| 1307.2 | b,12,+1 | -0.39 |  |  |  |  |
| 1338.68 | y-NH3,13,+1 | 0.084 |  |  |  |  |
| 1355.41 | y,13,+1 | -0.21 |  |  |  |  |

| Type | Peptide Sequence | AA Location | Mod. Position | MS/MS m/z (Observed) | z |
|---|---|---|---|---|---|
| 2 | KTGQAPGFSYTDANK | K39-K53 | K$_A$39 | 819.89 | 2 |
|  | EDLLAYLKK | E92-K100 | K$_T$99 | 1178.62 | 1 |

FIG. 11A CONTINUED

| | | |
|---|---|---|
| 1525.44 | b,14,+1 | 0.8 |
| 945.525 | y,8,+1 | 0.094 |
| 1002.5 | y,9,+1 | 0.047 |
| 332.199 | y,3,+1 | 0.0062 |
| 316.108 | b,2,+1 | -0.025 |
| 447.194 | y,4,+1 | -0.026 |
| 501.187 | b,4,+1 | -0.026 |
| 873.361 | b,8,+1 | -0.031 |
| 572.194 | b,5,+1 | -0.056 |
| 711.251 | y,6,+1 | -0.08 |
| 548.161 | y,5,+1 | -0.11 |
| 1099.4 | y,10,+1 | -0.11 |
| 1355.47 | y,13,+1 | -0.15 |
| 1170.38 | y,11,+1 | -0.16 |
| 798.195 | y,7,+1 | -0.17 |
| 1123.23 | b,10,+1 | -0.26 |
| 1224.22 | b,11,+1 | -0.32 |
| 286.161 | b,5,+2 | -0.47 |
| 1339.03 | b,12,+1 | -0.53 |

| Type | Peptide Sequence | AA Location | Mod. Position | MS/MS m/z (Observed) | z |
|---|---|---|---|---|---|
| 2 | TGQAPGFSYTDANKNK | T40-K55 | $K_T53$ | 892.90 | 2 |
| | YIPGTKMoxIFAGIK | Y74-K86 | $K_A79$ | 1508.82 | 1 |

FIG. 11A CONTINUED

| | | |
|---|---|---|
| 708.117 | b-NH3,6,+1 | -0.2 |
| | b-H2O,6,+1 | 0.78 |
| 722.605 | y-H2O,6,+1 | 0.25 |
| | y-NH3,6,+1 | -0.74 |
| 725.34 | b,6,+1 | -0.0064 |
| 740.223 | y,6,+1 | -0.15 |
| 820.894 | b-H2O,7,+1 | 0.47 |
| | b-NH3,7,+1 | -0.51 |
| 838.068 | b,7,+1 | -0.36 |
| 910.536 | y,8,+1 | 0.062 |
| 935.332 | b,8,+1 | -0.15 |
| 1039.44 | y,9,+1 | -0.077 |
| 1148.03 | b,10,+1 | 0.47 |
| 1221.98 | y,10,+1 | 0.36 |
| 1403.23 | b,12,+1 | -0.45 |

FIG. 11B CONTINUED

| | | |
|---|---|---|
| 474.097 | a,5,+1 | -0.21 |
| 476.234 | y,4,+1 | 0.024 |
| 502.06 | b,5,+1 | -0.24 |
| 578.741 | y-H2O,10,+2 | -0.05 |
| | y-NH3,10,+2 | -0.54 |
| 587.905 | y,10,+2 | 0.11 |
| 635.245 | y-H2O,11,+2 | -0.088 |
| | y-NH3,11,+2 | -0.58 |
| 683.905 | b,6,+1 | 0.5 |
| 692.402 | MH-NH3,,+2 | 0.035 |
| | MH-H2O,,+2 | 0.53 |
| 717.124 | y,6,+1 | -0.23 |
| 812.252 | b,7,+1 | -0.21 |
| 899.333 | y,7,+1 | -0.13 |
| 908.225 | b-NH3,8,+1 | -0.3 |
| 924.926 | b,8,+1 | -0.62 |
| 956.291 | y,8,+1 | -0.19 |
| 1027.29 | y,9,+1 | -0.23 |
| 1054.93 | a,9,+1 | 0.69 |
| 1168.96 | b,9,+1 | 0.34 |
| 1174.33 | b,10,+1 | -0.66 |
| 1210.35 | y,10,+1 | -0.26 |
| 1227.38 | b-NH3,11,+1 | 0.73 |
| | b,11,+1 | 0.74 |

FIG. 11B CONTINUED

| | | |
|---|---|---|
| 603.673 | y-H2O,10,+2 | 0.25 |
| 699.424 | y,10,+2 | -0.11 |
| | b-NH3,6,+1 | 0.071 |
| 707.709 | y-H2O,6,+1 | 0.082 |
| | MH-H2O,,+2 | -0.15 |
| | MH-NH3,,+2 | -0.64 |
| 844.448 | b,7,+1 | 0.0094 |
| 913.251 | y-H2O,7,+1 | -0.17 |
| 940.246 | b-NH3,8,+1 | -0.25 |
| 957.313 | b,8,+1 | -0.21 |
| 988.266 | y,8,+1 | -0.19 |
| 1059.39 | y,9,+1 | -0.099 |
| 1086.18 | b,9,+1 | -0.39 |
| 1189.46 | y-NH3,10,+1 | -0.071 |
| 1201.23 | b,10,+1 | -0.36 |
| 1206.67 | y,10,+1 | 0.11 |

FIG. 11B CONTINUED

| | | |
|---|---|---|
| 458.239 | y-H2O,4,+1 | 0.04 |
| 476.138 | y,4,+1 | -0.072 |
| 501.924 | b,5,+1 | -0.38 |
| 514.4 | y,9,+2 | 0.14 |
| | a,9,+2 | 0.6 |
| 570.503 | y-H2O,5,+1 | -0.78 |
| 578.838 | y-H2O,10,+2 | 0.047 |
| | y-NH3,10,+2 | -0.44 |
| 587.67 | y,10,+2 | -0.13 |
| 635.443 | y-H2O,11,+2 | 0.11 |
| | y-NH3,11,+2 | -0.38 |
| 643.835 | y,11,+2 | -0.5 |
| 684.196 | b,6,+1 | -0.21 |
| 691.941 | MH-H2O,,+2 | 0.066 |
| | MH-NH3,,+2 | -0.43 |
| 717.342 | y,6,+1 | -0.011 |
| 812.256 | b,7,+1 | -0.21 |
| 899.369 | y,7,+1 | -0.089 |
| 925.166 | b,8,+1 | -0.38 |
| 956.306 | y,8,+1 | -0.17 |
| 1027.44 | y,9,+1 | -0.077 |
| 1054.2 | b,9,+1 | -0.39 |
| 1169.22 | b,10,+1 | -0.4 |
| 1174.37 | y,10,+1 | -0.22 |

FIG. 11B CONTINUED

SUPPLEMENTAL FIG. 1B CONTINUED

| | | |
|---|---|---|
| 790.389 | b,13,+2 0.02 | |
| | b-NH3,7,+1 | 0.027 |
| 851.587 | y,7,+1 0.041 | |
| 900.694 | y,14,+2 0.22 | |
| | a,15,+2 -0.75 | |
| 918.3 | b-NH3,8,+1 | -0.12 |
| 938.54 | y,8,+1 -0.038 | |
| 993.359 | y-NH3,16,+2 | 0.37 |
| 1001.66 | y,16,+2 0.15 | |
| 1067.46 | y,9,+1 -0.16 | |
| 1100.17 | MH-NH3,,+2 | 0.11 |
| | MH-H2O,,+2 | 0.6 |
| 1132.41 | b-NH3,9,+1 | -0.086 |
| 1392.72 | y-NH3,11,+1 | -0.01 |
| 1409.59 | y,11,+1 -0.17 | |
| 1522.79 | y,12,+1 -0.051 | |
| 1636.81 | y,13,+1 -0.074 | |
| 1717.29 | b,14,+1 0.5 | |
| 1829.68 | b,15,+1 -0.19 | |

FIG. 11B CONTINUED

| | | |
|---|---|---|
| 383.568 | b-H2O,5,+1 | -0.62 |
| 396.105 | b-H2O,8,+2 | -0.1 |
| | b-NH3,8,+2 | -0.59 |
| 402.139 | b,5,+1 | -0.059 |
| 405.206 | b,8,+2 | -0.0052 |
| 443.073 | y-H2O,11,+3 | -0.15 |
| | y-NH3,7,+2 | 0.36 |
| | y-NH3,11,+3 | -0.48 |
| | y-NH3,14,+4 | 0.6 |
| 446.503 | a-NH3,9,+2 | -0.23 |
| | y,14,+4 | -0.23 |
| 451.74 | y,7,+2 | 0.51 |
| 459.863 | b-H2O,9,+2 | -0.37 |
| 469.173 | b,9,+2 | -0.068 |
| 485.656 | y-H2O,12,+3 | -0.26 |
| | y,16,+4 | 0.41 |
| | y-NH3,12,+3 | -0.58 |
| 491.999 | y,12,+3 | 0.083 |
| | y-H2O,8,+2 | -0.75 |
| 502.222 | y,8,+2 | 0.47 |
| 525.061 | b-NH3,10,+2 | -0.19 |
| | b-H2O,10,+2 | 0.3 |
| 528.479 | y-H2O,13,+3 | -0.12 |
| | y,18,+4 | 0.21 |
| | y-NH3,4,+1 | 0.22 |
| | y-NH3,13,+3 | -0.45 |
| 533.792 | b,10,+2 | 0.03 |
| 552.301 | y,9,+2 | 0.023 |
| 581.826 | b-NH3,11,-2 | 0.035 |
| | b-H2O,11,-2 | 0.53 |
| 595.48 | y,14,+3 | 0.18 |
| 608.653 | y,10,+2 | -0.17 |
| 622.248 | y-NH3,15,-3 | 0.27 |
| | y-H2O,15,-3 | 0.6 |

FIG. 13 CONTINUED

| | | |
|---|---|---|
| 627.966 | y,15,+3 | 0.31 |
| 637.134 | a-NH3,7,+1 | 0.8 |
| 640.673 | y-H2O,16,+3 | 0.014 |
|  | b,12,+2 | -0.15 |
| 646.569 | y-NH3,16,+3 | -0.31 |
| 655.12 | y,16,+3 | -0.093 |
| 664.345 | a,18,+3 | 0.79 |
|  | y-H2O,11,+2 | 0.0093 |
|  | b-NH3,7,+1 | 0.015 |
|  | y-NH3,11,+2 | -0.48 |
|  | b,18,+3 | 0.68 |
| 668.667 | a-NH3,13,+2 | -0.17 |
| 673.306 | y,11,+2 | -0.035 |
| 680.438 | y,17,+3 | 0.093 |
| 698.257 | y-NH3,18,+3 | -0.091 |
|  | y-H2O,18,+3 | 0.24 |
|  | a-NH3,19,+3 | 0.58 |
| 704.306 | y,18,+3 | 0.28 |
| 728.472 | y-H2O,12,+2 | 0.11 |
|  | y-NH3,12,+2 | -0.38 |
| 731.029 | y-H2O,19,+3 | -0.67 |
| 737.545 | y,19,+3 | -0.16 |
|  | y,12,+2 | 0.17 |
| 792.724 | y-NH3,13,+2 | -0.16 |
|  | y-H2O,13,+2 | 0.33 |
|  | b-NH3,8,+1 | 0.34 |
| 796.572 | b-NH3,15,+2 | 0.17 |
|  | b-H2O,15,+2 | 0.66 |
| 801.373 | y,13,+2 | -0.027 |
| 861.098 | b-NH3,16,+2 | 0.17 |
|  | b-H2O,16,+2 | 0.67 |
| 883.185 | y-H2O,7,+1 | -0.26 |
|  | y-H2O,14,+2 | -0.26 |
|  | y-NH3,14,+2 | -0.75 |
| 901.628 | y,7,+1 | 0.18 |

FIG. 13 CONTINUED

| | | |
|---|---|---|
| 936.875 | b,9,+1 | -0.6 |
| 1002.504 | y,8,+1 | 0.0037 |
| 1022.264 | a-NH3,10,+1 | 0.77 |
| 1048.5 | b-H2O,10,+1 | -0.0058 |
| 1067.152 | b,10,+1 | 0.64 |
| 1085.999 | y-H2O,9,+1 | 0.46 |
| | y-NH3,9,+1 | -0.52 |
| 1327.638 | y-H2O,11,+1 | -0.026 |
| 1456.001 | y-H2O,12,+1 | 0.28 |
| | y-NH3,12,+1 | -0.71 |

FIG. 13 CONTINUED

| | | |
|---|---|---|
| 297.287 | a,2,+1 | -0.029 |
| | b-H2O,7,+3 | 0.33 |
| | b-NH3,2,+1 | 0.16 |
| 310.146 | b+H2O,7,+3 | -0.52 |
| | y,2,+1 | -0.03 |
| | y-NH3,5,+2 | 0.5 |
| 314.171 | b,2,+1 | 0.018 |
| 318.277 | y,5,+2 | 0.12 |
| 344.673 | y-H2O,6,+2 | -0.0013 |
| | y-NH3,6,+2 | -0.49 |
| 354.011 | y,6,+2 | 0.33 |
| 357.025 | a,3,+1 | -0.17 |
| 379.376 | y-H2O,3,+1 | 0.18 |
| 385.256 | b,3,+1 | 0.066 |
| 397.27 | y,3,+1 | 0.062 |
| 402.78 | y,7,+2 | -0.43 |
| 414.207 | a-NH3,7,+2 | -0.48 |
| 437.254 | b,7,+2 | 0.054 |
| 498.202 | y,4,+1 | -0.054 |
| 501.237 | MH-H2O,,+2 | -0.01 |
| | MH-NH3,,+2 | -0.5 |
| 522.143 | b,4,+1 | -0.11 |
| 617.535 | y-H2O,5,+1 | 0.23 |
| | y-NH3,5,+1 | -0.75 |
| 623.368 | b,5,+1 | 0.071 |
| 635.309 | y,5,+1 | -0.0058 |
| 688.23 | y-H2O,6,+1 | -0.11 |
| 692.321 | b-H2O,6,+1 | 0.0025 |
| 706.319 | y,6,+1 | -0.033 |
| 787.464 | y-H2O,7,+1 | 0.054 |
| 805.55 | y,7,+1 | 0.13 |
| 845.253 | a,7,+1 | -0.14 |
| 855.303 | b-H2O,7,+1 | -0.079 |
| 873.283 | b,7,+1 | -0.11 |
| 891.579 | b+H2O,7,+1 | 0.18 |

FIG. 13 CONTINUED

| | | |
|---|---|---|
| 260.791 | b,2,+1 | -0.37 |
| | y,2,+1 | 0.59 |
| | y-H2O,3,+1 | 0.24 |
| 371.466 | y-NH3,3,+1 | -0.75 |
| 389.2 | y,3,+1 | -0.039 |
| 414.747 | y,6,+2 | 0.029 |
| | b,6,+2 | -0.45 |
| 447.296 | a,3,+1 | 0.054 |
| 458.124 | b-NH3,3,+1 | -0.087 |
| | a,7,+2 | 0.38 |
| 472.092 | b,7,+2 | 0.35 |
| 475.145 | b,3,+1 | -0.092 |
| 488.468 | y,7,+2 | 0.22 |
| 517.077 | y,4,+1 | -0.22 |
| 537.076 | MH-NH3,,+2 | 0.8 |
| 572.165 | b,4,+1 | -0.13 |
| 597.137 | y-NH3,5,+1 | -0.19 |
| | y-H2O,5,+1 | 0.8 |
| 614.311 | y,5,+1 | -0.04 |
| 699.877 | b,5,+1 | -0.47 |
| 828.342 | y,6,+1 | -0.086 |
| 924.13 | b-H2O,7,+1 | -0.33 |

FIG. 13 CONTINUED

| m/z | ion | error |
|---|---|---|
| 459.241 | b,3,+1 | -0.019 |
| 465.245 | MH-H2O,,+2 | -0.013 |
| | MH-NH3,,+2 | -0.51 |
| 489.27 | y,4,+1 | 0.0033 |
| 544.416 | a,4,+1 | 0.067 |
| 555.974 | b-NH3,4,+1 | 0.66 |
| 572.273 | b,4,+1 | -0.071 |
| 654.333 | y-NH3,5,+1 | -0.013 |
| 671.263 | y,5,+1 | -0.11 |
| 686.301 | b,5,+1 | -0.086 |
| 756.694 | a-NH3,6,+1 | 0.3 |
| 801.101 | b,6,+1 | -0.31 |
| 834.393 | y,6,+1 | -0.043 |

FIG. 13 CONTINUED

| | | |
|---|---|---|
| 727.414 | b,6,+1 | 0.062 |
| 771.915 | y,-H2O,13,+2 | 0.0032 |
| | b,-H2O,12,+2 | -0.44 |
| | y,-NH3,13,+2 | -0.49 |
| 825.493 | y,7,+1 | -0.026 |
| | a,13,+2 | 0.62 |
| 840.398 | b,7,+1 | -0.038 |
| 938.488 | y,8,+1 | -0.12 |
| 1037.41 | b,-NH3,8,+1 | -0.077 |
| 1054.55 | b,8,+1 | 0.036 |
| 1100.69 | a,18,+2 | 0.15 |
| 1182.79 | y,10,+1 | 0.12 |
| | y,19,+2 | 0.19 |
| 1460.57 | y,12,+1 | 0.79 |
| 1561.77 | b,12,+1 | 0.06 |
| 1790.47 | b,14,+1 | 0.65 |

FIG. 13 CONTINUED

| | | |
|---|---|---|
| 277.866 | b,2,+1 | 0.75 |
| 290.353 | y,2,+1 | 0.21 |
| 371.994 | b-H2O,3,+1 | -0.2 |
| 408.216 | b,6,+2 | 0.016 |
| 431.241 | y-NH3,6,+2 | 0.051 |
| | y-H2O,6,+2 | 0.54 |
| 436.581 | y-NH3,3,+1 | 0.4 |
| 439.865 | y,6,+2 | 0.16 |
| 453.308 | y,3,+1 | 0.099 |
| 488.336 | y-NH3,7,+2 | 0.6 |
| 490.439 | b,7,+2 | 0.71 |
| 496.23 | y,7,+2 | -0.016 |
| 501.079 | b-H2O,4,+1 | -0.16 |
| 550.328 | y-NH3,4,+1 | 0.1 |
| 567.306 | y,4,+1 | 0.054 |
| 625.089 | MH-H2O,,+2 | -0.21 |
| | MH-NH3,,+2 | -0.7 |
| 684.094 | b-NH3,5,+1 | -0.23 |
| | b-H2O,5,+1 | 0.75 |
| 701.495 | b,5,+1 | 0.14 |
| 732.521 | y-NH3,5,+1 | 0.19 |
| 749.404 | y,5,+1 | 0.046 |
| 769.87 | a-NH3,6,+1 | -0.5 |
| 798.629 | b-NH3,6,+1 | 0.26 |
| 861.619 | y-NH3,6,+1 | 0.25 |
| 878.443 | y,6,+1 | 0.043 |
| 961.075 | b-NH3,7,+1 | -0.36 |
| | b-H2O,7,+1 | 0.63 |
| 978.525 | b,7,+1 | 0.068 |
| 991.519 | y,7,+1 | 0.035 |
| 996.837 | b+H2O,7,+1 | 0.37 |
| 1075.047 | b-H2O,8,+1 | -0.43 |

FIG. 13 CONTINUED

| | | |
|---|---|---|
| 276.483 | y-H2O,4,+2 | -0.46 |
| | b-NH3,4,+2 | -0.16 |
| | y,2,+1 | 0.33 |
| 387.321 | y-H2O,3,+1 | 0.13 |
| 391.527 | b-NH3,6,+2 | -0.17 |
| 405.092 | y,3,+1 | -0.11 |
| 441.256 | b,3,+1 | 0.003 |
| 456.066 | b-NH3,7,+2 | -0.16 |
| | b-H2O,7,+2 | 0.34 |
| 465.016 | b,7,+2 | 0.28 |
| 473.82 | b-H2O,7,+2 | 0.08 |
| 489.194 | y,7,+2 | -0.031 |
| 536.093 | y,4,+1 | -0.15 |
| | y-H2O,8,+2 | -0.67 |
| 545.779 | y,8,+2 | 0.012 |
| 552.37 | b-NH3,4,+1 | 0.085 |
| 569.303 | b,4,+1 | -0.0086 |
| 593.894 | MH-NH3,,+2 | 0.098 |
| | MH-H2O,,+2 | 0.59 |
| 635.249 | y,5,+1 | -0.058 |
| 668.242 | b,5,+1 | -0.14 |
| 745.868 | y-NH3,6,+1 | -0.47 |
| | y-H2O,6,+1 | 0.51 |
| 754.043 | a-NH3,6,+1 | -0.36 |
| 763.211 | y,6,+1 | -0.15 |
| 772.151 | a,6,+1 | 0.73 |
| 782.194 | b-NH3,6,+1 | -0.2 |
| 799.25 | b,6,+1 | -0.17 |
| 883.94 | a-NH3,7,+1 | 0.5 |
| 928.087 | b,7,+1 | -0.38 |
| 959.175 | y-H2O,7,+1 | -0.26 |
| 977.268 | y,7,+1 | -0.18 |
| 1057.305 | b,8,+1 | -0.2 |
| 1090.506 | y,8,+1 | -0.021 |

FIG. 13 CONTINUED

| | | |
|---|---|---|
| 240.106 | y,1,+1 | -0.018 |
| 289.392 | b,3,+2 | 0.0044 |
| 293.128 | b-NH3,4,+2 | 0.78 |
| 310.229 | y-NH3,2,+1 | -0.022 |
| | y,2,+1 | 0.053 |
| | y-H2O,5,+2 | -0.44 |
| 350.172 | a,2,+1 | 0.019 |
| 361.226 | b-NH3,2,+1 | 0.1 |
| 378.026 | b,2,+1 | -0.12 |
| 423.386 | y,3,+1 | 0.13 |
| 426.804 | y,6,+2 | 0.086 |
| | b-NH3,6,+2 | 0.12 |
| | b-H2O,6,+2 | 0.61 |
| 435.138 | b,6,+2 | -0.059 |
| 444.31 | b+H2O,6,+2 | 0.11 |
| 479.131 | b,3,+1 | -0.065 |
| 499.526 | MH-NH3,+2 | -0.21 |
| | MH-H2O,+2 | 0.28 |
| 537.589 | y,4,+1 | 0.29 |
| 576.857 | b-NH3,4,+1 | 0.64 |
| 593.188 | b,4,+1 | -0.051 |
| 620.111 | y-H2O,5,+1 | -0.23 |
| 638.212 | y,5,+1 | -0.14 |
| 678.321 | a,5,+1 | -0.007 |
| 688.351 | b-H2O,5,+1 | 0.039 |
| 706.271 | b,5,+1 | -0.052 |
| 824.418 | a-NH3,6,+1 | 0.053 |
| 834.554 | y-H2O,6,+1 | 0.14 |
| 841.471 | a,6,+1 | 0.08 |
| 852.459 | y,6,+1 | 0.031 |
| | b-NH3,6,+1 | 0.099 |
| 869.326 | b,6,+1 | -0.06 |

FIG. 13 CONTINUED

| | | |
|---|---|---|
| 408.398 | b-NH3,3,+1 | 0.19 |
| 415.276 | y-H2O,3,+1 | 0.082 |
| 425.142 | b,3,+1 | -0.097 |
| 433.167 | y,3,+1 | -0.037 |
| 443.364 | b+H2O,3,+1 | 0.11 |
| 526.131 | a,4,+1 | -0.16 |
| 536.173 | b-H2O,4,+1 | -0.098 |
| 554.157 | b,4,+1 | -0.13 |
| 572.691 | b+H2O,4,+1 | 0.4 |
| 597.264 | y-H2O,4,+1 | -0.035 |
| 615.3 | y,4,+1 | -0.0097 |

FIG. 13 CONTINUED

| | | |
|---|---|---|
| 427.424 | a-NH3,5,+1 | -0.79 |
| 442.162 | y,11,+3 | 0.61 |
| 455.431 | b-H2O,5,+1 | 0.21 |
| | b-NH3,5,+1 | -0.78 |
| 470.325 | y,12,+3 | -0.24 |
| 473.299 | b,5,+1 | 0.064 |
| 554.33 | y,9,+2 | 0.051 |
| 558.367 | a,6,+1 | 0.042 |
| 568.172 | b-H2O,6,+1 | -0.14 |
| 586.161 | b,6,+1 | -0.16 |
| 615.41 | a,7,+1 | 0.064 |
| 625.479 | b-H2O,7,+1 | 0.15 |
| 637.276 | y,4,+1 | -0.025 |
| 643.042 | b,7,+1 | -0.3 |
| | b-H2O,12,+2 | -0.77 |
| 653.007 | y-H2O,11,+2 | 0.19 |
| | b,12,+2 | 0.19 |
| | y-NH3,11,+2 | -0.3 |
| 661.738 | b-H2O,12,+2 | -0.086 |
| | y,11,+2 | -0.086 |
| 696.647 | y-NH3,12,+2 | -0.18 |
| | y-H2O,12,+2 | 0.31 |
| 714.444 | a-NH3,8,+1 | -0.74 |
| 725.28 | a,8,+1 | 0.03 |
| | y-NH3,13,+2 | -0.058 |
| | b-NH3,8,+1 | -0.1 |
| 734.361 | y-H2O,13,+2 | 0.43 |
| | y-NH3,5,+1 | 0.043 |
| | y,13,+2 | 0.51 |
| 742.284 | b,8,+1 | -0.13 |
| 751.322 | y,5,+1 | -0.022 |
| 781.608 | MH-H2O,,+2 | 0.22 |

FIG. 13 CONTINUED

| | | |
|---|---|---|
| 802.084 | MH-NH3,,+2 | -0.27 |
| 811.538 | a,9,+1 | 0.64 |
| 821.133 | b-H2O,9,+1 | 0.11 |
| | y-NH3,6,+1 | -0.22 |
| | y-H2O,6,+1 | 0.77 |
| 829.283 | b,9,+1 | -0.16 |
| 838.352 | y,6,+1 | -0.024 |
| 919.034 | y-H2O,7,+1 | -0.4 |
| 926.447 | b-NH3,10,+1 | -0.011 |
| 937.46 | y,7,+1 | 0.015 |
| 943.01 | b,10,+1 | -0.47 |
| 977.627 | y-NH3,8,+1 | 0.19 |
| 994.411 | y,8,+1 | -0.055 |
| 1090.315 | y-NH3,9,+1 | -0.21 |
| | y-H2O,9,+1 | 0.78 |
| 1107.34 | y,9,+1 | -0.21 |
| 1129.251 | a,11,+1 | -0.32 |
| 1139.879 | b-H2O,11,+1 | 0.33 |
| | b-NH3,11,+1 | -0.66 |
| 1157.547 | b,11,+1 | -0.015 |
| 1176.534 | y-H2O,10,+1 | -0.038 |
| 1194.382 | y,10,+1 | -0.2 |
| 1287.483 | b-NH3,12,+1 | -0.12 |
| 1304.209 | b,12,+1 | -0.42 |
| | y-H2O,11,+1 | -0.42 |
| 1410.095 | y,12,+1 | 0.42 |
| 1415.764 | b-H2O,13,+1 | 0.1 |
| 1433.707 | b,13,+1 | 0.034 |
| 1451.378 | b+H2O,13,+1 | -0.31 |

FIG. 13 CONTINUED

| | | |
|---|---|---|
| 678.129 | y-H2O,6,+1 | -0.22 |
| 720.379 | y,12,+2 | 0.0045 |
| 800.047 | b,6,+1 | 0.65 |
| 810.678 | y,13,+2 | -0.75 |
| 859.49 | MH-H2O,,+2 | 0.047 |
| | MH-NH3,+2 | -0.45 |
| 909.806 | b-H2O,7,+1 | 0.36 |
| | b-NH3,7,+1 | -0.62 |
| 927.101 | b,7,+1 | -0.36 |
| 937.522 | y,8,+1 | 0.023 |
| 1023.373 | b-NH3,8,+1 | -0.14 |
| 1155.548 | b,9,+1 | -0.02 |
| 1213.531 | y,10,+1 | -0.12 |
| 1318.201 | b,10,+1 | -0.43 |
| 1342.843 | y,11,+1 | 0.15 |
| 1414.62 | b-NH3,11,+1 | -0.069 |
| 1421.539 | y-H2O,12,+1 | -0.19 |
| 1432.511 | b,11,+1 | 0.8 |
| 1439.616 | y,12,+1 | -0.13 |

FIG. 13 CONTINUED

| | | |
|---|---|---|
| 637.469 | y,4,+1 | 0.17 |
| 643.214 | b,7,+1 | -0.13 |
| | b-H2O,12,+2 | -0.6 |
| 653.492 | y-NH3,11,+2 | 0.18 |
| | y-H2O,11,+2 | 0.67 |
| | b,12,+2 | 0.67 |
| 662.115 | y,11,+2 | 0.29 |
| | b+H2O,12,+2 | 0.29 |
| 694.194 | a-NH3,13,+2 | -0.64 |
| 697.323 | a-NH3,8,+1 | -0.065 |
| | y-NH3,12,+2 | 0.5 |
| 713.924 | a,8,+1 | -0.49 |
| 724.266 | b-H2O,8,+1 | -0.13 |
| | y-H2O,13,+2 | -0.58 |
| 734.19 | y-NH3,5,+1 | -0.13 |
| | y,13,+2 | 0.34 |
| 742.115 | b,8,+1 | -0.29 |
| 751.299 | y,5,+1 | -0.045 |
| 781.46 | MH-H2O,,+2 | 0.072 |
| | MH-NH3,,+2 | -0.42 |
| 811.466 | b-H2O,9,+1 | 0.035 |
| 821.057 | y-NH3,6,+1 | -0.29 |
| | y-H2O,6,+1 | 0.69 |
| 838.34 | y,6,+1 | -0.036 |
| 937.309 | y,7,+1 | -0.14 |
| 943.251 | b,10,+1 | -0.23 |
| 994.302 | y,8,+1 | -0.16 |
| 1089.669 | y-H2O,9,+1 | 0.13 |
| 1107.337 | y,9,+1 | -0.21 |
| 1139.432 | b-H2O,11,+1 | -0.12 |
| 1194.464 | y,10,+1 | -0.12 |
| 1287.619 | b-NH3,12,+1 | 0.015 |
| 1322.772 | y,11,+1 | 0.13 |
| | b+H2O,12,+1 | 0.13 |
| 1415.416 | b-H2O,13,+1 | -0.25 |
| 1451.699 | b+H2O,13,+1 | 0.015 |

FIG. 13 CONTINUED

| | | |
|---|---|---|
| 437.224 | y-NH3,4,+1 | 0.04 |
| 446.383 | y-NH3,8,+2 | 0.56 |
| 485.117 | y,8,+2 | -0.019 |
| | y,4,+1 | 0.11 |
| | y-NH3,9,+2 | -0.15 |
| | y-H2O,9,+2 | 0.34 |
| 493.81 | y,9,+2 | 0.025 |
| 583.038 | b-H2O,11,+2 | 0.22 |
| | b-NH3,11,+2 | -0.27 |
| 591.794 | b,11,+2 | -0.028 |
| | y-NH3,11,+2 | 0.45 |
| 627.389 | b,12,+2 | 0.049 |
| 642.003 | b,6,+1 | -0.34 |
| 676.892 | b,13,+2 | 0.017 |
| 691.528 | y-H2O,13,+2 | -0.36 |
| 700.94 | y,13,+2 | 0.049 |
| 717.937 | b-H2O,14,+2 | -0.46 |
| 727.19 | b,14,+2 | -0.21 |
| | a,7,+1 | -0.24 |
| 755.118 | b,7,+1 | -0.31 |
| 808.419 | b-H2O,8,+1 | -0.037 |
| 826.746 | b,8,+1 | 0.28 |
| 855.235 | y-H2O,8,+1 | -0.23 |
| 873.469 | y,8,+1 | -0.0099 |
| 969.608 | y-NH3,9,+1 | 0.072 |

FIG. 13 CONTINUED

| | | |
|---|---|---|
| 404.231 | y,3,+1 | -0.031 |
| 442.511 | a,5,+1 | 0.21 |
| | b-H2O,12,+3 | -0.7 |
| 453.066 | b-H2O,5,+1 | 0.78 |
| 455.318 | b-H2O,12,+3 | 0.099 |
| 470.084 | b,5,+1 | -0.21 |
| 479.245 | a-NH3,9,+2 | 0.52 |
| 502.535 | y-NH3,4,+1 | 0.27 |
| 519.35 | y,4,+1 | 0.061 |
| 525.87 | y,8,+2 | 0.14 |
| 535.901 | a-NH3,10,+2 | -0.34 |
| 582.222 | y,9,+2 | -0.05 |
| 608.487 | a,11,+2 | -0.31 |
| 622.936 | y-H2O,10,+2 | 0.14 |
| | b,11,+2 | 0.14 |
| 631.695 | y-NH3,10,+2 | -0.36 |
| | b-H2O,11,+2 | -0.11 |
| | y,10,+2 | -0.11 |
| 639.064 | a-NH3,6,+1 | -0.29 |
| 665.86 | y-H2O,11,+2 | -0.46 |
| | b-H2O,6,+1 | -0.5 |
| 675.37 | y,11,+2 | 0.048 |
| 703.389 | y-H2O,6,+1 | 0.052 |
| 721.32 | y,6,+1 | -0.028 |
| 731.883 | y,12,+2 | 0.019 |
| 751.336 | MH-H2O,+2 | -0.033 |
| | MH-NH3,+2 | -0.53 |
| 781.179 | b-H2O,7,+1 | -0.21 |
| 798.956 | b,7,+1 | -0.45 |
| 819.487 | y-NH3,7,+1 | 0.14 |
| 836.384 | y,7,+1 | 0.0095 |
| 984.943 | b-NH3,9,+1 | 0.51 |
| 1032.171 | y-H2O,8,+1 | -0.27 |
| 1050.288 | y,8,+1 | -0.16 |
| 1097.99 | b-H2O,10,+1 | -0.49 |

FIG. 13 CONTINUED

| | | |
|---|---|---|
| 165.016 | b,2,+2 | -0.58 |
| 210.695 | y,5,+3 | 0.24 |
| 228.373 | y-NH3,2,+1 | -0.78 |
| 246.209 | y,2,+1 | 0.028 |
| 301.14 | a,5,+2 | -0.53 |
| 306.179 | y-H2O,5,+2 | -2.10E-04 |
| | b-H2O,5,+2 | -0.48 |
| | y-NH3,5,+2 | -0.49 |
| 313.2 | b-NH3,2,+1 | 0.045 |
| 330.145 | b,2,+1 | -0.036 |
| 380.102 | MH-NH3,,+2 | -0.1 |
| | MH-H2O,,+2 | 0.39 |
| 429.313 | y-H2O,4,+1 | 0.067 |
| 444.248 | b,3,+1 | 0.024 |
| 447.206 | y,4,+1 | -0.05 |
| 513.375 | b-H2O,4,+1 | 0.13 |
| 531.209 | b,4,+1 | -0.047 |
| 585.255 | a-NH3,5,+1 | -0.048 |
| 602.306 | a,5,+1 | -0.024 |
| 612.192 | b-H2O,5,+1 | -0.12 |
| | y-NH3,5,+1 | -0.14 |
| 629.27 | y,5,+1 | -0.092 |
| 647.852 | b+H2O,5,+1 | -0.48 |

FIG. 13 CONTINUED

| | | |
|---|---|---|
| 428.229 | y,3,+1 | -0.058 |
| | y,8,+2 | 0.49 |
| 484.359 | y-NH3,9,+2 | 0.61 |
| 507.488 | a,4,+1 | 0.27 |
| 518.264 | b-NH3,4,+1 | 0.076 |
| 535.081 | b,4,+1 | -0.13 |
| 573.764 | y,10,+2 | -0.029 |
| 599.231 | a-NH3,11,+2 | -0.049 |
| | y,5,+1 | -0.12 |
| 621.088 | b,11,+2 | -0.7 |
| 628.767 | y-H2O,11,+2 | -0.05 |
| | y-NH3,11,+2 | -0.54 |
| 685.887 | MH-H2O,,+2 | 0.048 |
| | MH-NH3,,+2 | -0.44 |
| 757.545 | y,7,+1 | 0.12 |
| 790.594 | b,7,+1 | 0.26 |
| 837.663 | y-NH3,8,+1 | 0.22 |
| 854.498 | y,8,+1 | 0.025 |
| 887.428 | b-NH3,8,+1 | 0.075 |
| 965.404 | y-H2O,9,+1 | -0.1 |
| 983.665 | y,9,+1 | 0.15 |
| 1128.361 | y-H2O,10,+1 | -0.21 |
| 1146.677 | y,10,+1 | 0.098 |

FIG. 13 CONTINUED

MASS SPECTROMETRY-CLEAVABLE CROSS-LINKING AGENTS TO FACILITATE STRUCTURAL ANALYSIS OF PROTEINS AND PROTEIN COMPLEXES, AND METHOD OF USING SAME

CROSS-REFERENCE TO RELATED APPLICATIONS

This application is based on U.S. provisional patent application No. 61/486,260, filed May 14, 2011, the entire contents of which are incorporated by reference herein.

STATEMENT REGARDING FEDERALLY SPONSORED RESEARCH OR DEVELOPMENT

This invention was made with Government support under Grant No. GM074830, awarded by the National Institute of Health. The Government has certain rights in this invention.

FIELD OF THE INVENTION

The invention relates to the field of cross-linking agents and, more specifically, MS-cleavable cross-linkers that are diester derivatives of 3,3'-sulfinylbispropanoic acid, and the use of such compounds to facilitate structural analysis of proteins and protein complexes.

BACKGROUND OF THE INVENTION

Knowledge of elaborate structures of protein complexes is fundamental for understanding their functions and regulations. Although cross-linking coupled with mass spectrometry (MS) has been presented as a feasible strategy for structural elucidation of large multi-subunit protein complexes, this method has proven challenging due to technical difficulties in unambiguous identification of cross-linked peptides and determination of cross-linked sites by MS analysis.

Proteins form stable and dynamic multi-subunit complexes under different physiological conditions to maintain cell viability and normal cell homeostasis. Detailed knowledge of protein interactions and protein complex structures is fundamental to understanding how individual proteins function within a complex and how the complex functions as a whole. However, structural elucidation of large multi-subunit protein complexes has been difficult due to lack of technologies which can effectively handle their dynamic and heterogeneous nature. Traditional methods such as nuclear magnetic resonance (NMR) analysis and X-ray crystallography can yield detailed information on protein structures; however, NMR spectroscopy requires large quantities of pure protein in a specific solvent while X-ray crystallography is often limited by the crystallization process.

In recent years, chemical cross-linking coupled with mass spectrometry (MS) has become a powerful method for studying protein interactions. See for example the disclosures of Sinz, A. (2003) Chemical Cross-Linking and Mass Spectrometry for Mapping Three-Dimensional Structures of Proteins and Protein Complexes. *J Mass Spectrom.* 38, 1225-1237; Sinz, A. (2006) Chemical Cross-Linking and Mass Spectrometry to Map Three-Dimensional Protein Structures and Protein-Protein Interactions. *Mass Spectrom Rev* 25, 663-682; and Leitner, A., Walzthoeni, T., Kahraman, A., Herzog, F., Rinner, O., Beck, M., and Aebersold, R. (2010) Probing Native Protein Structures by Chemical Cross-Linking, Mass Spectrometry and Bioinformatics. *Molecular & Cellular Proteomics* 9, 1634-1649. Chemical cross-linking stabilizes protein interactions through the formation of covalent bonds and allows the detection of stable, weak and/or transient protein-protein interactions in native cells or tissues See for example the disclosures of Sinz, A. (2010) Investigation of Protein-Protein Interactions in Living Cells by Chemical Crosslinking and Mass Spectrometry. *Anal Bioanal Chem* 397, 3433-3440; Vasilescu, J., Guo, X., and Kast, J. (2004) Identification of Protein-Protein Interactions Using in Vivo Cross-Linking and Mass Spectrometry. *Proteomics* 4, 3845-3854; Guerrero, C., Tagwerker, C., Kaiser, P., and Huang, L. (2006) An Integrated Mass Spectrometry-Based Proteomic Approach: Quantitative Analysis of Tandem Affinity-Purified in Vivo Cross-Linked Protein Complexes (Qtax) to Decipher the 26 S Proteasome-Interacting Network. *Mol Cell Proteomics* 5, 366-378; Tagwerker, C., Flick, K., Cui, M., Guerrero, C., Dou, Y., Auer, B., Baldi, P., Huang, L., and Kaiser, P. (2006) A Tandem Affinity Tag for Two-Step Purification under Fully Denaturing Conditions: Application in Ubiquitin Profiling and Protein Complex Identification Combined with in Vivo cross-Linking. *Mol Cell Proteomics* 5, 737-748; Guerrero, C., Milenkovic, T., Przulj, N., Kaiser, P., and Huang, L. (2008) Characterization of the Proteasome Interaction Network Using a Qtax-Based Tag-Team Strategy and Protein Interaction Network Analysis. *Proc Natl Acad Sci U.S.A* 105, 13333-13338; and Kaake, R. M., Milenkovic, T., Przulj, N., Kaiser, P., and Huang, L. (2010) Characterization of Cell Cycle Specific Protein Interaction Networks of the Yeast 26s Proteasome Complex by the Qtax Strategy. *J Proteome Res* 9, 2016-2019. In addition to capturing protein interacting partners, many studies have shown that chemical cross-linking can yield low-resolution structural information about the constraints within a molecule. See for example the disclosures of Sinz, A. (2006) Chemical Cross-Linking and Mass Spectrometry to Map Three-Dimensional Protein Structures and Protein-Protein Interactions. *Mass Spectrom Rev* 25, 663-682; Leitner, A., Walzthoeni, T., Kahraman, A., Herzog, F., Rinner, O., Beck, M., and Aebersold, R. (2010) Probing Native Protein Structures by Chemical Cross-Linking, Mass Spectrometry and Bioinformatics. *Molecular & Cellular Proteomics* 9, 1634-1649; and Back, J. W., de Jong, L., Muijsers, A. O., and de Koster, C. G. (2003) Chemical Cross-Linking and Mass Spectrometry for Protein Structural Modeling. *J Mol Biol.* 331, 303-313, or protein complex, as disclosed in Rappsilber, J., Siniossoglou, S., Hurt, E. C., and Mann, M. (2000) A Generic Strategy to Analyze the Spatial Organization of Multi-Protein Complexes by Cross-Linking and Mass Spectrometry. *Anal Chem.* 72, 267-275; Maiolica, A., Cittaro, D., Borsotti, D., Sennels, L., Ciferri, C., Tarricone, C., Musacchio, A., and Rappsilber, J. (2007) Structural Analysis of Multiprotein Complexes by Cross-Linking, Mass Spectrometry, and Database Searching. *Mol Cell Proteomics* 6, 2200-2211; and Chen, Z. A., Jawhari, A., Fischer, L., Buchen, C., Tahir, S., Kamenski, T., Rasmussen, M., Lariviere, L., Bukowski-Wills, J. C., Nilges, M., Cramer, P., and Rappsilber, J. (2010) Architecture of the Rna Polymerase Ii-Tfiif Complex Revealed by Cross-Linking and Mass Spectrometry. *Embo J* 29, 717-726. The application of chemical cross-linking, enzymatic digestion, and subsequent mass spectrometric and computational analysis for the elucidation of three dimensional protein structures offers distinct advantages over traditional methods due to its speed, sensitivity, and versatility. Identification of cross-linked peptides provides distance constraints that aid in constructing the structural topology of proteins and/or protein complexes. Although this approach has been successful, effective detection and accurate identification of cross-linked peptides as well as unambiguous assignment of cross-linked sites remain extremely challenging due to their low abundance and complicated fragmentation behavior in MS analysis. See for the example the disclosures of Sinz, A. (2006) Chemical Cross-Linking and Mass Spectrometry to Map Three-Dimensional Protein Structures and Protein-Protein Interactions. *Mass Spectrom Rev* 25, 663-682; Leitner, A., Walzthoeni, T., Kahraman, A., Herzog, F., Rinner, O., Beck, M., and Aebersold, R. (2010) Probing Native Protein Structures by Chemical Cross-Linking, Mass Spectrometry and Bioinformatics. *Molecular & Cellular Proteomics* 9, 1634-1649; Back, J. W., de Jong, L., Muijsers, A. O., and de Koster, C. G. (2003) Chemical Cross-Linking and Mass Spectrometry for Protein Structural Modeling. *J Mol Biol.* 331, 303-313; and Schilling, B., Row, R. H., Gibson, B. W., Guo, X., and Young, M. M. (2003) Ms2assign, Automated Assignment and Nomenclature of Tandem Mass Spectra of Chemically Crosslinked Peptides. *J Am Soc Mass Spectrom.* 14, 834-850. Therefore, new reagents and methods are urgently needed to allow unambiguous identification of cross-linked products and to improve the speed and accuracy of data analysis to facilitate its application in structural elucidation of large protein complexes.

A number of approaches have been developed to facilitate MS detection of low abundance cross-linked peptides from complex mixtures. These include selective enrichment using affinity purification with biotinylated cross-linkers, for example, as described in Trester-Zedlitz, M., Kamada, K., Burley, S. K., Fenyo, D., Chait, B. T., and Muir, T. W. (2003) A Modular Cross-Linking Approach for Exploring Protein Interactions. *J Am Chem Soc.* 125, 2416-2425; Tang, X., Munske, G. R., Siems, W. F., and Bruce, J. E. (2005) Mass Spectrometry Identifiable Cross-Linking Strategy for Studying Protein-Protein Interactions. *Anal Chem* 77, 311-318; and Chu, F., Mahrus, S., Craik, C. S., and Burlingame, A. L. (2006) Isotope-Coded and Affinity-Tagged Cross-Linking (Icatxl): An Efficient Strategy to Probe Protein Interaction Surfaces. *J Am Chem Soc* 128, 10362-10363, and click chemistry with alkyne-tagged (Chowdhury, S. M., Du, X., Tolic, N., Wu, S., Moore, R. J., Mayer, M. U., Smith, R. D., and Adkins, J. N. (2009) Identification of Cross-Linked Peptides after Click-Based Enrichment Using Sequential Collision-Induced Dissociation and Electron Transfer Dissociation Tandem Mass Spectrometry. *Anal Chem* 81, 5524-5532) or azide tagged cross-linkers, see for example Kasper, P. T., Back, J. W., Vitale, M., Hartog, A. F., Roseboom, W., de Koning, L. J., van Maarseveen, J. H., Muijsers, A. O., de Koster, C. G., and de Jong, L. (2007) An Aptly Positioned Azido Group in the Spacer of a Protein Cross-Linker for Facile Mapping of Lysines in Close Proximity. *Chembiochem* 8, 1281-1292; and Nessen, M. A., Kramer, G., Back, J., Baskin, J. M., Smeenk, L. E., de Koning, L. J., van Maarseveen, J. H., de Jong, L., Bertozzi, C. R., Hiemstra, H., and de Koster, C. G. (2009) Selective Enrichment of Azide-Containing Peptides from Complex Mixtures. *J Proteome Res* 8, 3702-3711. In addition, Staudinger ligation has recently been shown to be effective for selective enrichment of azide-tagged cross-linked peptides (Vellucci, D., Kao, A., Kaake, R. M., Rychnovsky, S. D., and Huang, L. (2010) Selective Enrichment and Identification of Azide-Tagged Cross-Linked Peptides Using Chemical Ligation and Mass Spectrometry. *J Am Soc Mass Spectrom* 21, 1432-1445). Apart from enrichment, detection of cross-linked peptides can be achieved by isotope-labeled, as described in Collins, C. J., Schilling, B., Young, M., Dollinger, G., and Guy, R. K. (2003) Isotopically Labeled Crosslinking Reagents: Resolution of Mass Degeneracy in the Identification of Crosslinked Peptides. *Bioorg Med Chem Lett.* 13, 4023-4026; Petrotchenko, E. V., Olkhovik, V. K., and Borchers, C. H. (2005) Isotopically Coded Cleavable Cross-Linker for Studying Protein-Protein Interaction and Protein Complexes. *Mol Cell Proteomics* 4, 1167-1179; and Petrotchenko, E., and Borchers, C. (2010) Icc-Class: Isotopically-Coded Cleavable Crosslinking Analysis Software Suite. *BMC bioinformatics* 11, 64, fluorescently labeled (Sinz, A., and Wang, K. (2004) Mapping Spatial Proximities of Sulfhydryl Groups in Proteins Using a Fluorogenic Cross-Linker and Mass Spectrometry. *Anal Biochem.* 331, 27-32), and mass-tag labeled cross-linking reagents, for example as described in Tang, X., Munske, G. R., Siems, W. F., and Bruce, J. E. (2005) Mass Spectrometry Identifiable Cross-Linking Strategy for Studying Protein-Protein Interactions. *Anal Chem* 77, 311-318; and Back, J. W., Hartog, A. F., Dekker, H. L., Muijsers, A. O., de Koning, L. J., and de Jong, L. (2001) A New Crosslinker for Mass Spectrometric Analysis of the Quaternary Structure of Protein Complexes. *J. Am. Soc. Mass Spectrom.* 12, 222-227. These methods can identify cross-linked peptides with MS analysis, but interpretation of the data generated from inter-linked peptides (two peptides connected with the cross-link) by automated database searching remains difficult. Several bioinformatics tools have thus been developed to interpret MS/MS data and determine inter-linked peptide sequences from complex mixtures, as described in Maiolica, A. et al.; Schilling, B. et al.; Chu, F., Baker, P. R., Burlingame, A. L., and Chalkley, R. J. (2009) Finding Chimeras: A Bioinformatic Strategy for Identification of Cross-Linked Peptides. *Mol Cell Proteomics* 9, 25-31; Gao, Q., Xue, S., Shaffer, S. A., Doneanu, C. E., Goodlett, D. R., and Nelson, S. D. (2008) Minimize the Detection of False Positives by the Software Program Detectshift for 18o-Labeled Cross-Linked Peptide Analysis. *Eur J Mass Spectrom (Chichester, Eng)* 14, 275-280; Singh, P., Shaffer, S. A., Scherl, A., Holman, C., Pfuetzner, R. A., Larson Freeman, T. J., Miller, S. I., Hernandez, P., Appel, R. D., and Goodlett, D. R. (2008) Characterization of Protein Cross-Links Via Mass Spectrometry and an Open-Modification Search Strategy. *Anal Chem* 80, 8799-8806; Rinner, O., Seebacher, J., Walzthoeni, T., Mueller, L. N., Beck, M., Schmidt, A., Mueller, M., and Aebersold, R. (2008) Identification of Cross-Linked Peptides from Large Sequence Databases. *Nat Methods* 5, 315-318; Lee, Y. J., Lackner, L. L., Nunnari, J. M., and Phinney, B. S. (2007) Shotgun Cross-Linking Analysis for Studying Quaternary and Tertiary Protein Structures. *J Proteome Res* 6, 3908-3917; and Nadeau, O. W., Wyckoff, G. J., Paschall, J. E., Artigues, A., Sage, J., Villar, M. T., and Carlson, G. M. (2008) Crosssearch, a User-Friendly Search Engine for Detecting Chemically Cross-Linked Peptides in Conjugated Proteins. *Mol Cell Proteomics* 7, 739-749. Although promising, further developments are still needed to make such data analyses as robust and reliable as analyzing MS/MS data of single peptide sequences using existing database searching tools (e.g. Protein Prospector, Mascot or SEQUEST).

Various types of cleavable cross-linkers with distinct chemical properties have been developed to facilitate MS identification and characterization of cross-linked peptides. These include UV photocleavable (Nadeau, O. W., Wyckoff, G. J., Paschall, J. E., Artigues, A., Sage, J., Villar, M. T., and Carlson, G. M. (2008) Crosssearch, a User-Friendly Search Engine for Detecting Chemically Cross-Linked Peptides in Conjugated Proteins. *Mol Cell Proteomics* 7, 739-749), chemical cleavable (Kasper, P. T., et al.), isotopically-coded cleavable (Petrotchenko, E. V., et al.), and MS-cleavable reagents, as described in Tang, X, et. al.; Back, J. W., et. al.; Zhang, H., Tang, X., Munske, G. R., Tolic, N., Anderson, G. A., and Bruce, J. E. (2009) Identification of Protein-Protein Interactions and Topologies in Living Cells with Chemical Cross-Linking and Mass Spectrometry. *Mol Cell Proteomics* 8, 409-420; Soderblom, E. J., and Goshe, M. B. (2006) Collision-Induced Dissociative Chemical Cross-Linking Reagents and Methodology: Applications to Protein Structural Characterization Using Tandem Mass Spectrometry Analysis. *Anal Chem* 78, 8059-8068; Soderblom, E. J., Bobay, B. G., Cavanagh, J., and Goshe, M. B. (2007) Tandem Mass Spectrometry Acquisition Approaches to Enhance Identification of Protein-Protein Interactions Using Low-Energy Collision-Induced Dissociative Chemical Crosslinking Reagents. *Rapid Commun Mass Spectrom* 21, 3395-3408; Lu, Y., Tanasova, M., Borhan, B., and Reid, G. E. (2008) Ionic Reagent for Controlling the Gas-Phase Fragmentation Reactions of Cross-Linked Peptides. *Anal Chem* 80, 9279-9287; and Gardner, M. W., Vasicek, L. A., Shabbir, S., Anslyn, E. V., and Brodbelt, J. S. (2008) Chromogenic Cross-Linker for the Characterization of Protein Structure by Infrared Multiphoton Dissociation Mass Spectrometry. *Anal Chem* 80, 4807-4819. MS-cleavable cross-linkers have received considerable attention since the resulting cross-linked products can be identified based on their characteristic fragmentation behavior observed during MS analysis. Gas-phase cleavage sites result in the detection of a "reporter" ion (Back, J. W., et al.), single peptide chain fragment ions (Soderblom, E. J., and Goshe; Soderblom, E. J., Bobay, B. G., et al.; Lu, Y., et al. and Gardner, M. W. et al.), or both reporter and fragment ions (Tang, X., et al.; and Zhang, H. et. al.). In each case, further structural characterization of the peptide product ions generated during the cleavage reaction can be accomplished by subsequent $MS^{n1}$ analysis. Among these linkers, the "fixed charge" sulfonium ion containing cross-linker developed by Lu. et. al appears to be the most attractive as it allows specific and selective fragmentation of cross-linked peptides regardless of their charge and amino acid composition based on their studies with model peptides.

Despite the availability of multiple types of cleavable cross-linkers, most of the applications have been limited to the study of model peptides and single proteins. Additionally, complicated synthesis and fragmentation patterns have impeded most of the known MS-cleavable cross-linkers from wide adaptation by the community.

SUMMARY OF THE INVENTION

The present invention provides novel cross-linking compounds that can be coupled with multi-stage tandem mass spectrometry ($MS^n$) to facilitate structural analysis of proteins and protein complexes. In a first aspect of the invention, a new crosslinking compound is provided and has the formula:

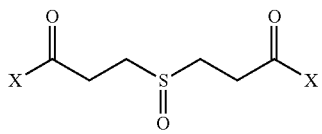

where x is selected from the group consisting of

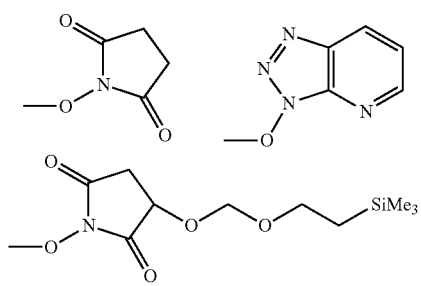

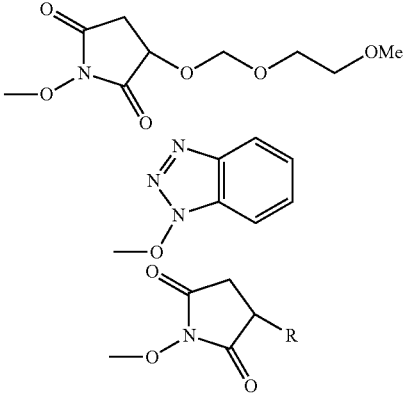

wherein R is methyl or ethyl, and

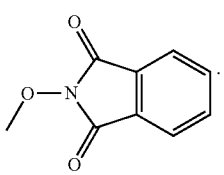

Compounds of the general formula shown above are symmetric diester derivatives of 3,3'-sulfinylbispropanoic acid, also known as 3,3'-sulfinyldipropanoic acid, $C_6H_{10}O_5S$. Like the diacid, the diesters have two symmetric collision-induced dissociation (CID)-cleavable sites that allow effective identification of diestercross-linked peptides based on their distinct fragmentation patterns unique to cross-linking types (i.e. inter-link, intra-link, and dead-end).

In a second aspect of the invention, the new cross-linking agents are used to facilitate mapping of protein-protein interactions of protein complexes. In one embodiment, the method comprises the steps of providing a MS-cleavable cross-linker having the formula described above; forming a cross-linked protein complex by cross-linking proteins with the MS-cleavable cross-linker; forming protein and/orpeptide fragments that are chemically bound to the MS-cleavable cross-linker by digesting the cross-linked protein complex with an enzyme such as trypsin; and using mass spectrometry (MS) and $MS^n$ analysis to identify the protein and/or peptide fragments.

In another aspect of the invention, a method for integrated data analysis work flow for identification of cross-linked peptides is provided and comprises the steps of providing cross-linked peptides, each cross-linked peptide comprising an MS-cleavable cross-linker as described above; performing mass spectrometry on the cross-linked peptides to obtain MS data, MS/MS data, and $MS^3$ data; identifying the MS/MS data comprising characteristic fragmentation profiles of MS-cleavable cross-linker-containing cross-linked peptides to obtain an MS/MS result comprising a list of parent ions corresponding to cross-linked peptide candidates; peptide sequencing the cross-linked peptides using the $MS^3$ data to obtain an $MS^3$ result comprising identities of cleaved crosslinked peptide fragments generated during MS/MS analysis; mass mapping the MS data using the list of parent ions corresponding to the cross-linked peptide candidates against a database comprising known protein sequences and the MS-cleavable cross-linker to obtain an MS result comprising possible cross-linked peptide sequences based on theoretical masses; and integrating the MS result, the MS/MS result, and $MS^3$ result to identify cross-linked peptides.

DESCRIPTION OF THE TABLES

Figure 1:
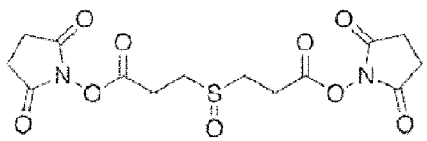
FIG. 1 shows exemplary Compounds 1 and 3-9 and General Structure 2 according to the invention.
Figure 1:
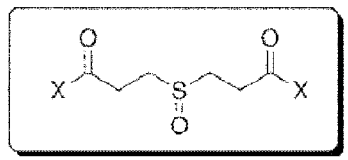
Figure 1:
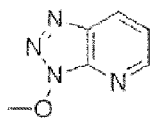
Figure 1:
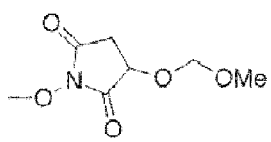
Figure 1:
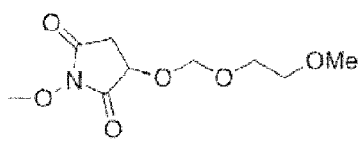
Figure 1:
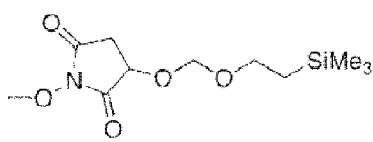
Figure 1:
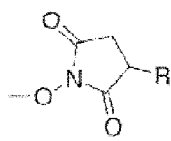
Figure 1:
Figure 1:
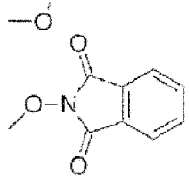

TABLE 1 Summary of DSSO-interlinked peptides of cytochrome c identified by LC MS$^n$.

TABLE 2 Summary of DSSO-interlinked peptides of the yeast 20 S proteasome complex identified by LC MS$^n$.

TABLE 3 Summary of DSSO cross-linked peptides—DSSO dead-end, intra-linked and multilinked peptides—of cytochrome c by LC MS$^n$.

TABLE 4 Summary of DSSO cross-linked peptides of ubiquitin by LC MS$^n$.

TABLE 5 Summary of DSSO inter-linked and dead-end peptides of the yeast 20S proteasome complex by LC MS$^n$.

TABLE 1

| Type | Peptide Sequence | AA Location | MS m/z (Observed) | z | Δ(PPM) | Mod. Position | m/z sequenced in MS3 | z | Distance (Cα-Cα) | References |
|---|---|---|---|---|---|---|---|---|---|---|
| 2 | Ac-GDVEKGK | G1-K7 | 565.30 | 3 | 1 | K$_T$5 | 860.38 | 1 | 5.3 Å | 19, 20, 21, 31 |
|   | K\|FVQK | K8-K13 |   |   |   | K$_A$8 | 408.75 | 2 |   |   |
| 2 | Ac-GDVEKGK | G1-K7 | 603.81 | 2 | 0 | K$_A$6 | 828.41 | 1 | 13.0 Å | 21, 31, 43 |
|   | KK | K87-K88 |   |   |   | K87* |   |   |   |   |
| 2 | Ac-GDVEKGK | G1-K7 | 516.93 | 3 | 0 | K$_T$5 | 860.38 | 1 | 13.0 Å | 21, 31 |
|   | KKGER | K87-R91 |   |   |   | K$_A$87 | 336.20 | 2 |   |   |
| 2 | Ac-GDVEKGK | G1-K7 | 474.23 | 3 | 2 | K$_A$5 | 414.71 | 2 | 13.0 Å | N/A |
|   | KGER | K88-R91 |   |   |   | K88* |   |   |   |   |
| 2 | Ac-GDVEKGK | G1-K7 | 675.35 | 3 | 4 | K$_T$5 | 860.38 | 1 | 13.2 Å | N/A |
|   | EDL\|AYLKK | E92-K100 |   |   |   | K$_A$99 | 573.83 | 2 |   |   |
| 2 | Ac-GDVEKGKK | G1-K8 | 445.57 | 3 | 1 | K$_A$7* | 478.76 | 2 | 15.7 Å | 21, 31 |
|   | KK | K87-K88 |   |   |   | K87* |   |   |   |   |
| 2 | Ac-GDVEKGKK | G1-K8 | 419.97 | 4 | 0 | K$_A$7 | 478.76 | 2 | 15.7 Å | 21, 31 |
|   | KKGER | K87-K91 |   |   |   | K$_T$87 | 352.18 | 2 |   |   |
| 2 | GKK | G6-K8 | 641.67 | 3 | 0 | K7* | 760.39 | 2 | 18.7 Å | 14, 31, 43 |
|   | HKTGPNLHGLFGR | H26-R38 |   |   |   | K$_T$27 |   |   |   |   |
| 2 | GKK | G6-K8 | 526.26 | 2 | 0 | K7* | 616.29 | 1 | 9.9 Å | 21, 43 |
|   | KATNE | K100-E104 |   |   |   | K$_A$100 |   |   |   |   |
| 2 | K\|FVQK | K8-K13 | 398.90 | 3 | 2 | K$_T$8 | 424.74 | 2 | 14.8 Å | 31 |
|   | KK | K87-K88 |   |   |   | K87* |   |   |   |   |
| 2 | K\|FVQK | K8-K13 | 384.97 | 4 | 2 | K$_A$8 | 408.75 | 2 | 14.8 Å | 31 |
|   | KKGER | K87-R91 |   |   |   | K$_T$87 | 352.18 | 2 |   |   |
| 2 | K\|FVQK | K8-K13 | 494.59 | 3 | 2 | K$_A$8 | 408.75 | 2 | 13.7 Å | 21, 31 |
|   | KATNE | K100-E100 |   |   |   | K100* |   |   |   |   |
| 2 | GGKHK | G23-K27 | 756.70 | 3 | 2 | K$_T$25 | 612.29 | 1 | 19.3 Å | N/A |
|   | KTGQAPGFSYTDANK | K39-K53 |   |   |   | K$_A$39 | 819.89 | 2 |   |   |
| 2 | KTGQAPGFSYTDANK | K39-K53 | 945.47 | 3 | 3 | K$_A$39 | 819.89 | 2 | 15.1 Å | 31 |
|   | EDL\|AYLKK | E92-K100 |   |   |   | K$_T$99 | 1178.62 | 1 |   |   |
| 2 | KTGQAPGFSYTDANK | K39-K53 | 768.69 | 3 | 0 | K$_T$39 | 835.88 | 2 | 18.0 Å | 21, 31, 43 |
|   | KATNE | K100-E104 |   |   |   | K100* |   |   |   |   |
| 2 | TGQAPGFSYTDANKNK | T40-K55 | 1104.21 | 3 | 2 | K$_T$53 | 892.90 | 2 | 11.6 Å | 31 |
|   | Y\|PGTKMox\|FAG\|K | Y74-K86 |   |   |   | K$_A$79 | 1508.82 | 1 |   |   |
| 2 | KY\|PGTK | K73-K79 | 629.68 | 3 | 2 | K$_T$73‡ | 892.46 | 1 | 13.2 Å | 31 |
|   | Mox\|FAG\|KK | M80-K87 |   |   |   | K$_T$86‡ | 1009.52 | 1 |   |   |
| 2 | M\|FAG\|KK | M80-K87 | 389.21 | 4 | 2 | KT86 | 497.27 | 2 | 6.4 Å | 31 |
|   | KGER | K88-R91 |   |   |   | K88* |   |   |   |   |
| 2 | Mox\|FAG\|KK | M80-K87 | 393.21 | 4 | 2 | KT86 | 505.27 | 2 | 6.4 Å | 31 |
|   | KGER | K88-R91 |   |   |   | K88* |   |   |   |   |

All of the interlinked peptides displayed characteristic fragment pairs and were identified by Batch-Tag, MS-Bridge, and Link-Finder. AA, amino acid; Mod., modification.
*Peptide fragments containing these sites were not sequenced by MS³.
‡They were identified from different fragment pair ions by MS³.

TABLE 2

| Type | Peptide Sequence | Subunit | AA Location | MS m/z (Observed) | z | Δ(PPM) | Mod. Position | m/z sequenced in MS3 | z | Distance (Cα-Cα) |
|---|---|---|---|---|---|---|---|---|---|---|
| 2 | ATATGPKQQEITTNLENHFK | α1 (PRS2/SCL1) | A168-K187 | 595.10 | 5 | 2 | K$_A$174 | 571.29 | 4 | 14.8 Å |
|   | KVPDK | α1 (PRS2/SCL1) | K58-K62 |   |   |   | K$_T$58 | 672.34 | 1 |   |
| 2 | KVAHTSYK | α2 (PRE8) | K91-K98 | 477.51 | 4 | 2 | K$_T$91 | 510.25 | 2 | 5.1 Å |
|   | VLVDKSR | α2 (PRE8) | V84-R90 |   |   |   | K$_A$88 | 435.76 | 2 |   |
| 2 | IFKPQEIK | α3 (PRE9) | I229-K236 | 514.03 | 4 | 0 | K$_T$231 | 544.80 | 2 | 14.2 Å |
|   | LYKLNDK | α3 (PRE9) | L66-K72 |   |   |   | K$_A$68 | 474.26 | 2 |   |
| 2 | IHAQNYLKTYNEDIPVEILVR | α3 (PRE9) | I93-R113 | 904.47 | 4 | 1 | K$_T$100 | 1307.68 | 2 | 10.6 Å |
|   | YKTNLYK | β3 (PL1P3) | Y69-K75 |   |   |   | K$_A$70 | 492.27 | 2 |   |
| 2 | EFLEKNYDR | α4 (PRE6) | E173-R181 | 692.33 | 3 | 2 | K$_A$177‡ | 634.30 | 2 | 13.1 Å |
|   | NSKTVR | α4 (PRE6) | N167-R172 |   |   |   | K$_A$169‡ | 379.71 | 2 |   |
| 2 | ILKQVMEEK | α5 (PUP2) | I203-K211 | 641.01 | 3 | 0 | K$_T$205 | 602.31 | 2 | 10.5 Å |
|   | ELKEK | α5 (PUP2) | E242-K246 |   |   |   | K244* |   |   |   |
| 2 | SYKFPR | β2 (PUP1)† | S202-R207 | 539.26 | 3 | 1 | K$_A$204 | 426.23 | 2 | 12.1 Å |
|   | EEKQK | β2 (PUP1)† | E197-K201 |   |   |   | K$_T$199 | 747.34 | 1 |   |

TABLE 2-continued

| Type | Peptide Sequence | Subunit | AA Location | MS m/z (Observed) | z | Δ(PPM) | Mod. Position | m/z sequenced in MS3 | z | Distance (Cα-Cα) |
|---|---|---|---|---|---|---|---|---|---|---|
| 2 | YKTNLYK | β3 (PUP3) | Y69-K75 | 587.64 | 3 | 2 | $K_A70$‡ | 492.26 | 2 | 10.7 Å |
|  | LKEER | β3 (PUP3) | L76-R80 |  |  |  | $K_T77$‡ | 364.70 | 2 |  |
| 2 | LGSQSLGVNKFEK | β3 (PUP3) | L29-K42 | 595.05 | 4 | 2 | $K_T39$ | 790.40 | 2 | 13.2 Å |
|  | YLKMoxR | β3 (PUP3) | Y199-R203 |  |  |  | $K_A201$ | 390.71 | 2 |  |
| 2 | NKPELYQIDYLGTK | β4 (PRE1) | N112-K125 | 833.92 | 4 | 0 | $K_A113$ | 868.45 | 2 | 19.1 Å |
|  | LGSQSLGVSNKFEK | β3 (PUP3) | L29-K42 |  |  |  | $K_T39$ | 790.39 | 2 |  |
| 2 | VQDSVILASSKAVTR | β4 (PRE1) | V9-R23 | 633.74 | 5 | 1 | $K_A19$ | 543.30 | 3 | 7.8 Å |
|  | GISVLKDSDDKTR | β4 (PRE1) | G24-R36 |  |  |  | $K_T29$ | 760.38 | 2 |  |
| 2 | FKNSVK | β6 (PRE7)† | F59-K64 | 532.29 | 3 | 2 | $K_T60$ | 808.40 | 1 | 16.2 Å |
|  | KLAVER | α6 (PRE5) | K102-R107 |  |  |  | $K_A102$ | 385.23 | 2 |  |
| 2 | NQYEPGTNGKVK | β6 (PRE7)† | N149-K150 | 659.68 | 3 | 0 | $K_A158$ | 694.84 | 2 | 9.8 Å |
|  | KPLK | β6 (PRE7)† | K161-K164 |  |  |  | K161* |  |  |  |

All of the interlinked peptides displayed characteristic fragment pairs and were identified by Batch-Tag, MS-Bridge, and Link-Finder. AA, amino acid; Mod., modification.
†Mature sequence from crystal data was used for data analysis.
‡They were identified from different fragment pair ions by $MS^3$.
*Peptide fragments containing these sites were not sequenced by $MS^3$.

TABLE 3

| Type | Peptide Sequence | AA Location | MS m/z (Observed) | z | Δ (PPM) | Mod. Position | m/z sequenced in MS3 | z | Peptide Score | Expectation Value | Identified in Other Refs |
|---|---|---|---|---|---|---|---|---|---|---|---|
| 0 | Ac-GDVEKGKK | G1-K8 | 539.76 | 2 | 1 | $K_T5$ | 494.74 | 2 | 22.7 | 1.90E-05 | 21 |
| 0 | KIFVQK | K8-K13 | 469.76 | 2 | 2 | $K_A8$ | 408.75 | 2 | 19.1 | 1.00E-04 | 19, 20, 21, 31 |
| 0 | KTGQAPGFSYTDANK | K39-K53 | 880.90 | 2 | 2 | $K_T39$ | 835.88 | 2 | 41.5 | 2.10E-10 | 19, 20, 21, 41 |
| 0 | TGQAPGFSYTDANKNK | T40-K55 | 937.92 | 2 | 0 | $K_T53$ | 892.90 | 2 | 28.8 | 4.60E-08 | 19, 31 |
| 0 | KYIPGTK | K73-K79 | 491.75 | 2 | 2 | $K_A73$ | 430.75 | 2 | 23.9 | 1.40E-05 | 20, 21, 31 |
| 0 | YIPGTKMoxIFAGIK | Y74-K86 | 815.92 | 2 | 2 | $K_T79$ | 770.90 | 2 | 18.3 | 5.00E-06 | 19, 31 |
| 0 | MoxIFAGIKK | M80-K87 | 550.28 | 2 | 1 | $K_T86$ | 505.27 | 2 | 22.0 | 4.20E-06 | 31 |
| 0 | EDLIAYLKK | E92-K100 | 634.83 | 2 | 1 | $K_A99$ | 573.83 | 2 | 32.9 | 2.70E-07 | 21, 31 |

| Type | Peptide Sequence | AA Location | MS m/z (Observed) | z | Δ (PPM) | Mod. Position | m/z sequenced in MS3 | z | Peptide Score | Expectation Value | Distance (Cα-Cα) | Identified in Other Refs |
|---|---|---|---|---|---|---|---|---|---|---|---|---|
| 1 | Ac-GDVEKGKK | G1-K8 | 530.75 | 2 | 2 | $K_A5$, $K_T7$ | 521.75 | 2 | 19.5 | 6.20E-05 | 5.4 Å | 21 |
| 1 | GGKHKTGPNLHGLFGR | G23-R38 | 611.98 | 3 | 0 | $K_A25$, $K_T27$ | 605.98 | 3 | 37.7 | 2.80E-08 | 6.3 Å | 14, 19, 20, 21, 31, 42 |
| 1 | KYIPGTKMOxIFAGIK | K73-K86 | 870.96 | 2 | 2 | K73, K79* | — | — | — |  | 12.1 Å | 31 |
| 1 | KYIPGTKMoxIFAGIKK | K73-K87 | 623.67 | 3 | 2 | K73, K86* | — | — | — |  | 13.2 Å | 31 |
| 1 | MoxIFAGIKKK | M80-K88 | 605.32 | 2 | 2 | $K_A86$, $K_T87$ | 596.32 | 2 | 29.5 | 1.10E-08 | — | 14, 19, 20, 21, 31, 42 |
| 1 | KKGER | K87-R91 | 388.19 | 2 | 1 | $K_A87$, $K_S88$* | — | — | — |  | — | 20, 21 |
| 1 | EDLIAYLKKATNE | E92-E104 | 833.41 | 2 | 3 | $K_A99$, $K_T100$ | 824.40 | 2 | 28.7 | 1.50E-06 | — | 21, 31 |

| Type | Peptide Sequence | AA Location | MS m/z (Observed) | z | Δ (PPM) | Mod. Position | m/z sequenced in MS3 | z | Best Discovery Score | Best Expectation Value | Distance (Cα-Cα) | References |
|---|---|---|---|---|---|---|---|---|---|---|---|---|
| 2 | Ac-GDVEKGK | G1-K7 | 565.30 | 3 | 1 | $K_T5$ | 860.38 | 1 | 19.7 | 270E-05 | 5.3 Å | 19, 20, 21, 31 |
|  | KIFVQK | K8-K13 |  |  |  | $K_A8$ | 408.75 | 2 | 20.3 | 1.90E-05 |  |  |
| 2 | Ac-GDVEKGK | G1-K7 | 603.81 | 2 | 0 | $K_A5$ | 828.41 | 1 | 23.1 | 2.70E-06 | 13.0 Å | 21, 31, 43 |
|  | KK | K87-K88 |  |  |  | K87* |  |  |  |  |  |  |
| 2 | Ac-GDVEKGK | G1-K7 | 516.93 | 3 | 0 | $K_T5$ | 860.38 | 1 | 19.7 | 2.70E-05 | 13.0 Å | 21, 31 |
|  | KKGER | K87-891 |  |  |  | $K_A87$ | 336.20 | 2 | 14.8 | 1.50E-04 |  |  |
| 2 | Ac-GDVEKGK | G1-K7 | 474.23 | 3 | 2 | $K_A5$ | 414.71 | 2 | 25.5 | 8.60E-07 | 13.0 Å | — |
|  | KGER | K88-R91 |  |  |  | K88* |  |  |  |  |  |  |
| 2 | Ac-GDVEKGK | G1-K7 | 675.35 | 5 | 4 | $K_T5$ | 860.38 | 1 | 19.7 | 2.70E-05 | 13.2 Å | — |
|  | EDLIAYLKK | E92-K100 |  |  |  | $K_A99$ | 573.83 | 2 | 32.9 | 2.10E-07 |  |  |
| 2 | Ac-GDVEKGKK | G1-K8 | 445.57 | 3 | 1 | $K_A7$ | 478.76 | 2 | 23.1 | 7.50E-06 | 15.7 Å | 21, 31 |
|  | KK | K87-K88 |  |  |  | K87* |  |  |  |  |  |  |
| 2 | Ac-GDVEKGKK | G1-K8 | 419.97 | 4 | 0 | $K_A7$ | 478.76 | 2 | 22.0 | 2.20E-05 | 15.7 Å | 21, 31 |
|  | KKGER | K87-K91 |  |  |  | $K_T87$ | 352.18 | 2 | 15.5 | 1.40E-03 |  |  |
| 2 | GKK | G6-K8 | 641.67 | 3 | 0 | K7* | 760.39 | 2 | 35.0 | 7.10E-11 | 18.7 Å | 14, 31, 43 |
|  | HKTGPNLHGLFGR | H26-838 |  |  |  | $K_T27$ |  |  |  |  |  |  |
| 2 | GKK | G6-K8 | 526.26 | 2 | 0 | K7* | 616.29 | 1 | 14.2 | 2.40E-09 | 9.9 Å | 21, 43 |
|  | KATNE | K100-E104 |  |  |  | $K_A100$ |  |  |  |  |  |  |
| 2 | KIFVQK | K8-K13 | 398.90 | 3 | 2 | $K_T8$ | 424.74 | 2 | 19.4 | 1.40E-04 | 14.8 Å | 31 |
|  | KK | K87-K88 |  |  |  | K87* |  |  |  |  |  |  |
| 2 | KIFVQK | K8-K13 | 384.97 | 4 | 2 | $K_A8$ | 408.75 | 2 | 20.3 | 1.90E-05 | 14.8 Å | 31 |
|  | KKGER | K87-R91 |  |  |  | $K_T87$ | 352.18 | 2 | 15.0 | 1.00E-04 |  |  |

TABLE 3-continued

| Type | Peptide Sequence | AA Location | MS m/z (Observed) | z | Δ (PPM) | Mod. Position | m/z sequenced in MS3 | z | Peptide Score | Expectation Value | Distance (Cα-Cα) | Identified in Other Refs |
|---|---|---|---|---|---|---|---|---|---|---|---|---|
| 2 | KIFVQK KATNE | K8-K13 K100-E104 | 494.59 | 3 | 2 | $K_A8$ $K_A100*$ | 408.75 | 2 | 20.6 | 3.20E-05 | 13.7 Å | 21, 31 |
| 2 | GGKHK KTGQAPGFSYTDANK | G23-K27 K39-K53 | 756.70 | 3 | 2 | $K_T25$ $K_A39$ | 612.29 819.89 | 1 2 | 9.0# 44.7 | 8.00E-03 5.70E-11 | 19.3 Å | — |
| 2 | KTGQAPGFSYTDANK EDLIAYLKK | K39-K53 E92-K100 | 945.47 | 3 | 3 | $K_A39$ $K_T99$ | 819.89 1178.62 | 2 1 | 42.5 22.9 | 2.50E-10 1.80E-05 | 15.1 Å | 31 |
| 2 | KTGQAPGFSYTDANK KATNE | K39-K53 K100-E104 | 768.69 | 3 | 0 | $K_T39$ $K_A100*$ | 835.88 | 2 | 39.9 | 1.20E-09 | 18.0 Å | 21, 31, 43 |
| 2 | TGQAPGFSYTDANKNK YIPGTKMoxIFAGIK | T40-K55 Y74-K86 | 1104.21 | 3 | 2 | $K_T53$ $K_A79$ | 892.90 1508.82 | 2 1 | 28.8 9.3# | 4.60E-08 1.00E-03 | 11.6 Å | 31 |
| 2 | KYIPGTK MoxIFAGIKK | K73-K79 M80-K87 | 629.68 | 3 | 2 | $K_T73‡$ $K_T86‡$ | 892.46 1009.52 | 1 1 | 17.6 15.0 | 2.00E-05 2.10E-05 | 13.2 Å | 31 |
| 2 | MIFAGIKK KGER | M80-K87 K88-R91 | 389.21 | 4 | 2 | $K_T86$ $K88*$ | 497.27 | 2 | 18.9 | 5.00E-05 | 6.4 Å | 31 |
| 2 | MoxIFAGIKK KGER | M80-K87 K88-R91 | 393.21 | 4 | 2 | $K_T86$ $K88*$ | 505.27 | 2 | 24.0 | 4.20E-07 | 6.4 Å | 31 |

| Type | Peptide Sequence | AA Location | MS m/z (Observed) | z | Δ (PPM) | Mod. Position | m/z sequenced in MS3 | z | Peptide Score | Expectation Value | Distance (Cα-Cα) | Identified in Other Refs |
|---|---|---|---|---|---|---|---|---|---|---|---|---|
| 0,0 | GGKHKTGPNLHGLFGR | G23-R38 | 507.74 | 4 | −2 | $K_A25, K_A27$ | 446.74 | 4 | 28.0 | 1.10E-06 | — | — |
| 0,1 | YIPGTKMoxIFAGIKKK | Y74-K88 | 682.34 | 3 | 1 | $K_A79, K_A86, K_T87$ | 635.67 | | 24.6 | 3.60E-05 | | |
| 0,1 | MoxIFAGIKKKGER | M80-R91 | 576.61 | 3 | 2 | $K_A86, K_A87, K_A88$ | 529.94 | | 31.8 | 1.20E-05 | — | |
| 0,1 | MoxIFAGIKKKGER | M80-R91 | 864.41 | 2 | 1 | $K_T86, K_A87, K_A88$ | 794.41 | 2 | 34.0 | 2.00E-08 | — | |
| 0,2 | Ac-GDVEKGKK KATNE | G1-K8 K100-E104 | 899.40 | 2 | 1 | K5, K7* $K_A100$ | 616.29 | 1 | 14.2 | 2.60E-08 | ~11.3 Å | — |
| 0,2 | GKK GGKHKTGPNLHGLFGR | G6-K8 G23-R38 | 469.04 | 5 | 0 | K7* $K_A25, K_A27$ | 446.74 | 4 | 22.3 | 4.20E-06 | ~18.7 Å | — |
| 0,2 | GKKIFVQK KK | G6-K13 K87-K88 | 519.28 | 3 | 2 | $K_T7, K_A8$ K87* | 544.30 | 2 | 23.1 | 1.90E-05 | ~15.3 Å | |
| 1,2 | Ac-GDVEKGK MoxIFAGIKKKGER | G1-K7 M80-R91 | 828.40 | 3 | 0 | $K_T5$ $K_A86, K_A87, K_T88$ | 860.38 794.41 | 1 2 | 19.5 36.3 | 3.20E-05 2.00E-09 | ~13.8 Å | |
| 1,2 | Ac-GDVEKGKKIFVQK KATNE | G1-K13 K100-E104 | 799.06 | 3 | 2 | $K_T5, K_T7, K_A8$ $K_A100$ | 872.43 616.30 | 2 1 | 18.7 14.2 | 1.20E-04 2.40E-09 | ~12.1 Å | |
| 1,2 | KYIPGTK MoxIFAGIKKKGER | K73-K79 M80-R91 | 839.10 | 3 | 1 | $K_T73$ $K_A86, K_T87, K_A88$ | 892.46 794.41 | 1 2 | 17.6 36.3 | 2.00E-05 2.00E-09 | ~15.3 Å | — |
| 2,2 | Ac-GDVEKGKK KKGER KATNE | G1-K8 K87-R91 K100-E104 | 599.79 | 4 | 0 | K5, K7* $K_A87$ $K100*$ | 336.20 | 2 | 14.8 | 1.50E-04 | ~14.38 Å, ~11.3 Å | — |

*Peptide fragments containing these sites were not sequenced by MS3.
**These intra-linked were identified by MS/MS.
These MS3 data were considered due to the presence of other lines of evidence for identifying the cross-linked peptides.
‡They were identified from different charged fragment pair ions by MS3

Note:
Type 0: dead-end
Type 1: intra-linked
Type 0,1; 0,2; 1,2; 2,2: multi-linked
All of the peptides displayed characteristic fragment pairs.
All of the cross-linked peptides were identified by Link-Finder, Batch-tag and MS-Bridge.

TABLE 4

| Type | Peptide Sequence | AA Location | MS m/z (Observed) | z | Δ (PPM) | Mod. Position | m/z sequenced in MS3 | z | Peptide Score | Expectation Value | Identified in Other Refs |
|---|---|---|---|---|---|---|---|---|---|---|---|
| 0 | MQIFVKTLTGK | M1-K11 | 721.38 | 2 | 9 | $K_T6$ | 676.36 | 2 | 30.1 | 5.40E-08 | 19, 38 |
| 0 | AKIQDK | A28-K33 | 439.72 | 2 | 7 | $K_T29$ | 394.71 | 2 | 18.0 | 2.40E-04 | — |
| 0 | LIFAGKQLEDGR | L43-R54 | 761.89 | 2 | 2 | $K_T48$ | 716.87 | 2 | 35.1 | 1.10E-07 | 19, 38 |
| 0 | LIFAGKQLEDGRTLSDYNIQK | L43-K62 | 862.44 | 3 | 8 | $K_T48$ | 832.43 | 3 | 34.1 | 1.20E-07 | — |
| 0 | TLSDYNIQKESTLHLVLR | T55-R72 | 769.40 | 3 | 10 | $K_A63$ | 728.73 | 3 | 36.1 | 1.40E-07 | 19, 38 |

| Type | Peptide Sequence | AA Location | MS m/z (Observed) | z | Δ (PPM) | Mod. Position | m/z sequenced in MS2 | z | Peptide Score | Expectation Value | Distance (Cα-Cα) | Identified in Other Refs |
|---|---|---|---|---|---|---|---|---|---|---|---|---|
| 1 | AKIQDKEGIPPDQQR | A28-R42 | 940.97 | 2 | 5 | K29, K33 | 940.97 | | 28.5 | 4.40E-07 | 6.42 Å | 19 |

TABLE 4-continued

| Type | Peptide Sequence | AA Location | MS m/z (Observed) | z | Δ (PPM) | Mod. Position | m/z sequenced in MS3 | z | Peptide Score | Expectation Value | Distance (Cα-Cα) | References |
|---|---|---|---|---|---|---|---|---|---|---|---|---|
| 2 | TLTGKTITLEVEPSDTIENVK IQDKEGIPPDQQR | T7-K27 I30-R42 | 993.01 | 4 | 5 | K11* $K_A33$ | 789.41 | 2 | 28.6 | 3.20E-08 | 13.3 Å | 38 |
| 2 | LIFAGKQLEDGR LIFAGKQLEDGR | L43-R54 L43-R54 | 713.38 | 4 | 5 | $K_A48$ $K_T48$ | 700.88 716.87 | 2 2 | 39.2 36.4 | 1.00E-08 1.90E-08 | 15.3 Å | 19 |
| 2 | LIFAGKQLEDGR TLSDYNIQKESTLHLVLR | L43-R54 T55-R72 | 909.24 | 4 | 9 | $K_A48$ $K_T63$ | 700.89 1108.58 | 2 2 | 35.5 31.3 | 1.80E-08 1.20E-08 | 18.4 Å | 19, 38 |

*Peptide fragments containing these sites were not sequenced by MS3.

Note:

Type 0: dead-end

Type 1: intra-linked

Type 2: inter-linked

All of the peptides displayed characteristic fragment pairs.

All of the cross-linked peptides were identified by Link-Finder, Batch-tag and MS-Bridge.

TABLE 5

| Type | Peptide Sequence | Subunit | AA Location | MS m/z (Observed) | z | Δ (PPM) | Mod. Position | m/z sequenced in MS3 | z | peptide Score | Expectation Value |
|---|---|---|---|---|---|---|---|---|---|---|---|
| 0 | AKAEAAEFR | α1 (PRS2/SCL1) | A97-R105 | 584.77 | 2 | −1 | $K_T98$ | 539.75 | 2 | 35.0 | 1.50E-04 |
| 0 | VLVDKSR | α2 (PRE8) | V84-R90 | 496.76 | 2 | 0 | $K_A88$ | 435.76 | 2 | 23.8 | 4.60E-04 |
| 0 | TFLEKR | α2 (PRE8) | T173-R178 | 485.24 | 2 | 1 | $K_A177$ | 424.24 | 2 | 22.9 | 3.30E-04 |
| 0 | KVTSTLLEQDTSTEK | α3 (PRE9) | K51-K65 | 928.45 | 2 | 1 | $K_A51$ | 867.45 | 2 | 47.2 | 3.50E-09 |
| 0 | STLKLQDTR | α4 (PRE6) | S50-R58 | 619.31 | 2 | 1 | $K_A53$ | 558.31 | 2 | 36.3 | 3.90E-05 |
| 0 | ITPSKVSK | α4 (PRE6) | I59-K66 | 518.27 | 2 | 1 | $K_T63$ | 473.26 | 2 | 21.3 | 2.30E-03 |
| 0 | ILIEKAR | α4 (PRE6) | I84-R90 | 509.78 | 2 | −1 | $K_T88$ | 464.77 | 2 | 27.4 | 1.40E-03 |
| 0 | NSKTVR | α4 (PRE6) | N167-R172 | 440.71 | 2 | 1 | $K_T176$ | 395.70 | 2 | 22.1 | 5.90E-03 |
| 0 | EFLEKNYDR | α4 (PRE6) | E173-R181 | 695.30 | 2 | −1 | $K_T177$ | 650.29 | 2 | 30.9 | 1.40E-05 |
| 0 | TAELIKELK | α5 (PUP2) | T236-K244 | 610.82 | 2 | −4 | $K_T241$ | 565.81 | 2 | 36.3 | 1.80E-04 |
| 0 | KLAVER | α6 (PRE5) | K102-R107 | 446.23 | 2 | 2 | $K_A102$ | 385.23 | 2 | 18.1 | 3.00E-04 |
| 0 | LLVPQKNVK | α7 (PRE10) | L58-K66 | 607.84 | 2 | 1 | $K_T63$ | 562.83 | 2 | 24.2 | 9.20E-05 |
| 0 | AELEKLVDHHPEGLSAR | α7 (PRE10) | A174-R190 | 693.00 | 3 | −2 | $K_T178$ | 663.00 | 3 | 33.5 | 6.70E-06 |
| 0 | EAVKQAAK | α7 (PRE10) | E191-K198 | 510.76 | 2 | 2 | $K_T194$ | 465.74 | 2 | 26.9 | 7.10E-04 |
| 0 | YKTNLYK | β3 (PUP3) | Y69-K75 | 553.27 | 2 | 3 | $K_T70$ | 508.25 | 2 | 25.7 | 9.60E-05 |
| 0 | TNLYKLK | β3 (PUP3) | T71-K77 | 528.27 | 2 | −5 | $K_A75$ | 467.27 | 2 | 25.9 | 2.50E-03 |
| 0 | QELAKSIR | β4 (PRE1) | Q86-R93 | 560.79 | 2 | 1 | $K_A90$ | 499.79 | 2 | 22.5 | 4.00E-03 |
| 0 | IVDKDGIR | β4 (PRE1) | I183-R190 | 546.27 | 2 | 1 | $K_T186$ | 501.26 | 2 | 30.6 | 1.40E-03 |
| 0 | FKNSVK | β6 (PRE7)† | F59-K64 | 449.72 | 2 | 1 | $K_T60$ | 404.71 | 2 | 19.0 | 1.90E-02 |
| 0 | KLSINSAAR | β6 (PRE7)† | K74-R82 | 568.29 | 2 | 3 | $K_A74$ | 507.29 | 2 | 32.8 | 2.00E-04 |
| 0 | KEFYELK | β6 (PRE7)† | K205-K211 | 566.77 | 2 | 2 | $K_A205$ | 505.77 | 2 | 24.7 | 5.40E-03 |

| Type | Peptide Sequence | Subunit | AA Location | MS m/z (Observed) | z | Δ (PPM) | Mod. Position | m/z sequenced in MS3 | z | Peptide Score | Expectation Value | Distance (Cα-Cα) |
|---|---|---|---|---|---|---|---|---|---|---|---|---|
| 2 | ATATGPKQQEITTNLENHFK KVPDK | α1 (PRS2/SCL1) α1 (PRS2/SCL1) | A168-K187 K58-K62 | 595.10 | 5 | 2 | $K_A174$ $K_T58$ | 571.29 672.34 | 4 1 | 24.5 12.3 | 2.90E-04 0.71** | 14.8 Å |
| 2 | KVAHTSYK VLVDKSR | α2 (PRE8) α2 (PRE8) | K91-K98 V84-R90 | 477.51 | 4 | 2 | $K_T91$ $K_A88$ | 510.25 435.76 | 2 2 | 29.9 27.6 | 7.60E-05 2.50E-03 | 5.1 Å |
| | KVAHTSYK VLVDKSR | α2 (PRE8) α2 (PRE8) | K91-K98 V84-R90 | 382.21 | 5 | 1 | $K_A91$ $K_T88$ | 329.85 451.74 | 3 2 | 19.3 25.4 | 1.90E-02 2.50E-04 | |
| 2 | IFKPQEIK LYKLNDK | α3 (PRE9) α3 (PRE9) | I229-K236 L66-K72 | 514.03 | 4 | 0 | $K_T231$ $K_A68$ | 544.80 474.26 | 2 2 | 21.6 25.5 | 1.50E-02 5.50E-03 | 14.2 Å |
| 2 | IHAQNYLKTYNEDIPVEILVR YKTNLYK | α3 (PRE9) β3 (PUP3) | I93-R113 Y69-K75 | 904.47 | 4 | 1 | $K_T100$ $K_A70$ | 1307.68 492.27 | 2 2 | 26.6 23.9 | 7.90E-05 3.00E-03 | 10.6 Å |
| | IHAQNYLKTYNEDIPVEILVR YKTNLYK | α3 (PRE9) 83 (PUP3) | I93-R113 Y69-K75 | 723.78 | 5 | 5 | K100* $K_A70$ | 492.27 | 2 | 24.2 | 2.90E-03 | |
| 2 | EFLEKNYDR NSKTVR | α4 (PRE6) α4 (PRE6) | E173-R181 N167-R172 | 692.33 | 3 | 2 | $K_A177$+ $K_A169$+ | 634.30 379.71 | 2 2 | 23.6 22.6 | 2.60E-04 2.80E-03 | 13.1 Å |
| | EFLEKNYDR NSKTVR | α4 (PRE6) α4 (PRE6) | E173-R181 N167-R172 | 519.50 | 4 | 2 | $K_T177$ $K_A169$ | 650.29 379.71 | 2 2 | 33.2 22.6 | 1.70E-05 2.80E-03 | |
| 2 | ILKQVMEEK ELKEK | α5 (PUP2) α5 (PUP2) | I203-K211 E242-K246 | 641.01 | 3 | 0 | $K_T205$ K244* | 602.31 | 2 | 29.2 | 3.50E-03 | 10.5 Å |
| | ILKQVMEEK ELKEK | α5 (PUP2) α5 (PUP2) | I203-K211 E242-K246 | 481.01 | 4 | 0 | $K_T205$ K244* | 602.31 | 2 | 27.6 | 2.60E-04 | |
| 2 | SYKFPR EEKQK | β2 (PUP1)† β2 (PUP1)† | S202-R207 E197-K201 | 539.26 | 3 | 1 | $K_A204$ $K_T199$ | 426.23 747.34 | 2 1 | 23.1 10.4 | 6.40E-03 0.33** | 12.1 Å |
| | SYKFPR EEKQK | β2 (PUP1)† β2 (PUP1)† | S202-R207 E197-K201 | 404.70 | 4 | 2 | $K_T204$ K199* | 442.21 | 2 | 21.1 | 8.20E-04 | |

TABLE 5-continued

| 2 | YKTNLYK | β3 (PUP3) | Y69-K75 | 587.64 | 3 | 2 | $K_A70^+$ | 492.26 | 2 | 23.8 | 4.60E-04 | 10.7 Å |
|---|---|---|---|---|---|---|---|---|---|---|---|---|
|   | LKEER | β3 (PUP3) | L76-R80 |   |   |   | $K_A77^+$ | 364.70 | 2 | 17.0 | 2.70E-02 |   |
|   | YKTNLYK | β3 (PUP3) | Y69-K75 | 440.98 | 4 | 2 | $K_T70$ | 508.25 | 2 | 25.7 | 1.10E-04 |   |
|   | LKEER | β3 (PUP3) | L76-R80 |   |   |   | $K_T77$ | 364.70 | 2 | 16.5 | 8.40E-03 |   |
| 2 | LGSQSLGVSNKFEK | β3 (PUP3) | L29-K42 | 793.07 | 3 | 2 | $K_A39$ | 774.41 | 2 | 42.0 | 5.30E-07 | 13.2 Å |
|   | YLKMoxR | β3 (PUP3) | Y199-R203 |   |   |   | $K_T201$ | 406.69 | 2 | 16.2 | 1.10E-03 |   |
|   | LGSQSLGVSNKFEK | β3 (PUP3) | L29-K42 | 595.05 | 4 | 2 | $K_T39$ | 790.40 | 2 | 40.7 | 8.40E-07 |   |
|   | YLKMoxR | β3 (PUP3) | Y199-R203 |   |   |   | $K_A201$ | 390.71 | 2 | 18.1 | 6.10E-03 |   |
| 2 | NKPELYQIDYLGTK | β4 (PRE1) | N112-K125 | 833.92 | 4 | 0 | $K_A113$ | 868.45 | 2 | 32.0 | 9.50E-08 | 19.1 Å |
|   | LGSQSLGVSNKFEK | β3 (PUP3) | L29-K42 |   |   |   | $K_T39$ | 790.39 | 2 | 26.5 | 3.90E-05 |   |
| 2 | VQDSVILASSKAVTR | β4 (PRE1) | V9-R23 | 633.74 | 5 | 1 | $K_A19$ | 543.30 | 3 | 23.0 | 4.90E-03 | 7.8 Å |
|   | GISVLKDSDDKTR | β4 (PRE1) | G24-R36 |   |   |   | $K_T29$ | 760.38 | 2 | 35.4 | 2.40E-05 |   |
| 2 | FKNSVK | β6 (PRE7)† | F59-K64 | 532.29 | 3 | 2 | $K_T60$ | 808.40 | 1 | 16.2 | 2.00E-02 | 16.2 Å |
|   | KLAVER | α6 (PRE5) | K102-R107 |   |   |   | $K_A102$ | 385.23 | 2 | 21.2 | 9.80E-04 |   |
|   | FKNSVK | β6 (PRE7)† | F59-K64 | 399.47 | 4 | 2 | $K_T60$ | 404.71 | 2 | 16.5 | 1.10E-02 |   |
|   | KLAVER | α6 (PRE5) | K102-R107 |   |   |   | $K_A102$ | 385.23 | 2 | 18.3 | 1.60E-04 |   |
| 2 | NQYEPGTNGKVK | β6 (PRE7)† | N149-K160 | 659.68 | 3 | 0 | $K_A158$ | 694.84 | 2 | 29.8 | 4.20E-05 | 9.8 Å |
|   | KPLK | β6 (PRE7)† | K161-K164 |   |   |   | K161* |   |   |   |   |   |
|   | NQYEPGTNGKVK | β6 (PRE7)† | N149-K160 | 495.01 | 4 | 2 | $K_T158$ | 710.83 | 2 | 26.3 | 3.00E-04 |   |
|   | KPLK | β6 (PRE7)† | K161-K164 |   |   |   | K161* |   |   |   |   |   |

*Peptide fragment containing these sites were not sequenced by MS3
**The peptide identification was above 1% false positive rate but MS3 was validated manually.
‡They were identified from different fragment pair ions by MS3
†Mature sequence from crystal data was used for data analysis.
Note:
Type 0: dead-end
All of the peptides displayed characteristic fragment pairs.
All of the cross-linked peptides were identified by Link-Finder, Batch-tag and MS-Bridge.

DETAILED DESCRIPTION OF THE INVENTION

In a first aspect of the invention, a new crosslinking compound is provided and has the formula:

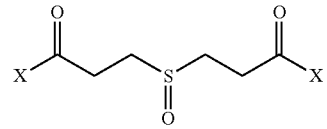

where x is selected from the group consisting of

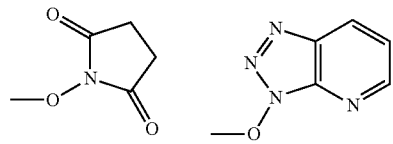

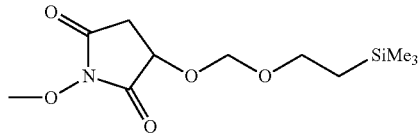

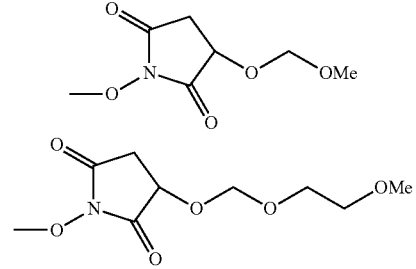

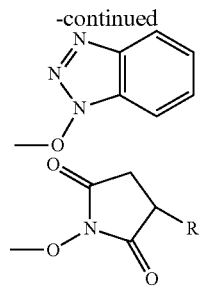

wherein R is methyl or ethyl, and

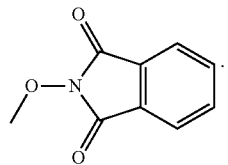

A particularly preferred cross-linking agent is bis(2,5-dioxopyrrolidin-1-yl) 3,3'-sulfinyldipropanoate ("DSSO"):

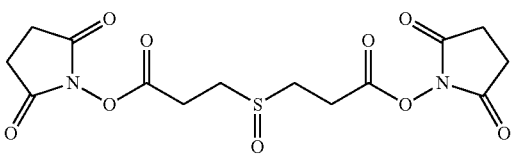 [SMILES: O=C(CCS(=O)CCC(=O)ON1C(=O)CCC1=O)ON1C(=O)CCC1=O]

In a second aspect of the invention, the new cross-linking agents are used to facilitate mapping of protein-protein interactions of protein complexes. In one embodiment, the method comprises the steps of providing a MS-cleavable cross-linker having the formula described above; forming a cross-linked protein complex by cross-linking proteins with the MS-cleavable cross-linker; forming cross-linked peptide fragments that are chemically bound to the MS-cleavable cross-linker by digesting the cross-linked protein complex with an enzyme such as trypsin; and using mass spectrometry (MS) and MS$^n$ analysis to identify the protein and/or peptide fragments. For convenience, in the discussion that follows, reference is sometimes made to the particular crosslinker, DSSO. It will be understood, however, that any of the other MS-cleavable crosslinkers that fit the general formula may also be used. Thus, DSSO fragments, DSSO remnants, DSSO cross-linked peptides, and like language applies equally to other crosslinkers as described herein.

ABBREVIATIONS

MS: mass spectrometry
MS/MS: tandem mass spectrometry
MS$^n$: multi-stage tandem mass spectrometry (n=2, 3, ...)
LC MS$^n$: liquid chromatography multi-stage tandem mass spectrometry
CID: collision induced dissociation
DSSO: bis(2,5-dioxopyrrolidin-1-yl) 3,3'-sulfinyldipropanoate
NMR: nuclear magnetic resonance The CID-induced separation of inter-linked peptides in MS/MS permits MS$^3$ analysis of single peptide chain fragment ions with defined modifications (due to diamide remnants) for easy interpretation and unambiguous identification using existing database searching tools. Integration of data analyses from three generated datasets (MS, MS/MS and MS$^3$) allows high confidence identification of DSSO cross-linked peptides. The efficacy of the newly developed DSSO-based cross-linking strategy has been demonstrated using model peptides and proteins. In addition, this method has been successfully employed for structural characterization of the yeast 20 S proteasome complex. In total, 13 non-redundant inter-linked peptides of the 20 S proteasome have been identified, representing the first application of an MS-cleavable cross-linker for the characterization of a multi-subunit protein complex. Given its effectiveness and simplicity, this cross-linking strategy can find a broad range of applications in elucidating structural topology of proteins and protein complexes.

In combination with new software developed for data integration, the inventors were able to identify DSSO cross-linked peptides from complex peptide mixtures with speed and accuracy. Given its effectiveness and simplicity, the inventors anticipate a broader application of this MS-cleavable cross-linker in the study of structural topology of other protein complexes using cross-linking and mass spectrometry.

EXPERIMENTAL PROCEDURES

Materials and Reagents

General chemicals were purchased from Fisher Scientific (Hampton, N.H.) or VWR International (West Chester, Pa.). Bovine heart cytochrome c (98% purity) and bovine erythrocyte ubiquitin (98% purity) were purchased from Sigma Aldrich (St. Louis, Mo.). Synthetic peptide Ac-IR7 (Ac-IE-AEKGR, 98.1% purity) was synthesized by GL Biochem (Shanghai, China). Sequencing grade modified trypsin was purchased from Promega (Fitchburg, Wis.). The 20 S proteasome core particle was affinity purified using Pre1-TAP expressing yeast strain as previously described in Leggett, D. S., Hanna, J., Borodovsky, A., Crosas, B., Schmidt, M., Baker, R. T., Walz, T., Ploegh, H., and Finley, D. (20032) Multiple Associated Proteins Regulate Proteasome Structure and Function. *Mol Cell.* 10, 495-507.

Synthesis and Characterization of DSSO—

FIG. 2A displays a two-step synthesis scheme of DSSO with an extended spacer length of 10.1 Å. Sulfide S-1 was first synthesized by mixing 3,3'-thiodipropionic acid (2.50 g, 14.0 mmol) with N-hydroxysuccinimide (3.30 g, 28.6 mmol) in dioxane (60 ml). The reaction mixture was stirred under an atmosphere of argon, and a solution of DCC (5.79 g, 28.1 mmol) in dioxane (20 ml) was added drop-wise. After 12 h, the insoluble urea was filtered from the reaction. The filtrate was concentrated to form a white solid. The solid residue was washed with cold diethyl ether followed by cold hexanes. After drying under reduced pressure, 5.20 g (70%) of sulfide S-1 was recovered and used without further purification: 1H (500 MHz, DMSO-d6) δ 3.02; (t, J=7.0 Hz, 4H), 2.86; (t, J=7.0 Hz, 4H), 2.81; (s, 8H); $^{13}$C (125 MHz, DMSO-d6) δ 170.1, 167.8, 31.4, 25.6, 25.4; IR (KBr pellet) 1801, 1732 cm$^{-1}$; HRMS (ES/MeOH) m/z calcd for $C_{14}H_{16}N_2O_8$SNa [M+Na]$^+$ 395.0525, found 395.0531.

To synthesize DSSO, a solution of sulfide S-1 (0.600 g, 1.61 mmol) in CHCl$_3$ (30 ml) at 0° C. was mixed with a solution of m-chloroperbenzoic acid (MCPBA) (0.371 g, 1.61 mmol) in CHCl$_3$ (10 ml). The reaction product was filtered and washed with cold CHCl$_3$ (10 ml) and cold MeOH (10 ml). The filtrate was cooled to −10° C. for 1 h, washed again with CHCl$_3$ and MeOH, and dried under reduced pressure to yield 0.400 g (64%) of DSSO: 1H (600 MHz, DMSO-d6) δ 3.28-3.21; (m, 2H), 3.17-3.13; (m, 4H), 3.08-2.99; (m, 2H), 2.88-2.75; (s, 8H); $^{13}$C (125 MHz, DMSO-d6) δ 170.08, 167.74, 44.62, 25.46, 23.41; IR (KBr pellet) 2943, 1786, 1720 cm$^{-1}$; HRMS (ES/MeOH) m/z calculated for $C_{14}H_{16}N_2O_9$Na [M+Na]$^+$ 411.0474, found 411.0471.

A similar synthetic approach is used to make the other symmetric diesters identified above and having the general structure 2, where X is as defined above. Thus, the symmetric sulfide is prepared by reacting 3,3'-thiodipropionic acid with the appropriate N-hydroxyamine (e.g., a functionalized analogue of N-hydroxysucinimide (compounds 4-7), or other N-hydroxy-functionalized heterocycle (compounds 3, 8, and 9), and then the sulfinyl group is made by treating the symmetric sulfide with MCPBA in CHCl$_3$ or another appropriate solvent.

Cross-Linking of Synthetic Peptides with DSSO—

Synthetic peptides Ac-IR7, Ac-myelin and substance P were dissolved in DMSO to 1 mM and cross-linked with DSSO dissolved in DMSO in a ratio of 1:1 in the presence of 1 equivalent diisopropylethylamine similarly as described Vellucci, D, et al. The cross-linked peptide solution was then diluted to 1 pmol/μl in 4% ACN, 0.1% formic acid for liquid chromatography multi-stage tandem mass spectrometry (LC MS$^n$) analysis.

Cross-Linking of Cytochrome C and Ubiquitin with DSSO—

Lyophilized bovine cytochrome c or ubiquitin was reconstituted in 1× PBS (pH 7.5) to 200 μM, 20 μl of which was mixed with 2 μl 20 mM DSSO (in DMSO) in a molar ratio of 1:10 (protein:cross-linker) for the cross-linking reaction as described in Vellucci, D., et al. The cross-linked protein was digested with trypsin (1% w/w) overnight at 37° C. The cross-linked peptide digest was then diluted to 1 pmol/μl in 4% ACN, 0.1% formic acid for LC MS$^n$ analysis.

Cross-Linking of the Yeast 20 S Proteasome with DSSO—

Affinity purified yeast 20S proteasome complex was concentrated by Microcon (Billerica, Mass.) to ~1.2 μM in 1× PBS buffer (pH 7.5). Typically 50 μl of the 20S proteasome was cross-linked with 3 μl DSSO (20 mM) dissolved in DMSO (final concentration ~1 mM) at a molar ratio of 1:1000 (protein:cross-linker). Cross-linking was performed for a half hour or overnight and quenched with excess ammonium bicarbonate buffer. Cysteine residues were reduced with 5 mM DTT at 56° C. for 30 mins, and alkylated with 10 mM choloroacetamide for 30 min at room temperature. The cross-linked protein complex was digested with trypsin (2% w/w) overnight at 37° C. Digested peptides were desalted by C18 OMIX ZipTip (Varian, Palo Alto, Calif.) prior to LC MS$^n$ analysis.

For some analyses, 2-dimensional LC MS$^n$ analysis was carried out. Off-line strong cation exchange (SCX) chromatography was performed as the first dimension of separation using an ÄKTA HPLC system (GE Healthcare Life Sciences, Uppsala, Sweden) as described in Kaake, R. M., et al. Each fraction was desalted by ZipTip prior to LC MS$^n$ analysis.

LC MS$^n$ Analysis—

LC MS$^n$ analysis of DSSO cross-linked peptides was performed using a LTQ-Orbitrap XL MS (Thermo Scientific, San Jose, Calif.) with an on-line Eksigent NanoLC system (Eksigent, Dublin, Calif.). The LC separation was the same as previously described by Vellucci, D., et al. The MS$^n$ method was set specifically for analyzing DSSO cross-linked peptides. Each acquisition cycle of a MS$^n$ experiment includes one MS scan in FT mode (350-1800 m/z, resolution of 60,000 at m/z 400) followed by two data-dependent MS/MS scans with normalized collision energy at 10 or 15% on the top two peaks from the MS scan, and then three MS$^3$ scans operated in LTQ with normalized collision energy at 29% on the top three peaks from each of the MS/MS scans. For initial analyses, MS/MS spectra were acquired in LTQ in LC MS$^n$ experiments. For automated data analysis, MS/MS spectra were obtained in FT mode (resolution of 7500).

Data Analysis of DSSO Cross-Linked Peptides—

Monoisotopic masses of parent ions and corresponding fragment ions, parent ion charge states and ion intensities from LC MS/MS and LC MS$^3$ spectra were extracted using in-house software based on Raw_Extract script from Xcalibur v2.4 (Thermo Scientific, San Jose, Calif.). Database searching was performed with a developmental version of Protein Prospector (v. 5.5.0, University of California, San Francisco) (http://prospector.ucsf.edu/prospector/mshome.htm) using its software suite, i.e. Batch-Tag and MS-Bridge as described in Chu, F., et al. Using in-house scripts, extracted MS$^3$ data were reformatted such that MS$^3$ fragment ions were directly linked to their MS/MS parent ions. For cytochrome c (P62894) and ubiquitin (P62990) analyses, database searching of MS$^3$ spectra was performed using Batch-Tag against their accession numbers in SwissProt.2009.09.01 database. For the 20S proteasome, Batch-Tag search of MS$^3$ data was performed against a decoy database consisting of a normal SGD yeast database concatenated with its reversed version (total 13490 protein entries). The mass tolerances for parent ions and fragment ions were set as ±20 ppm and 0.6 Da, respectively. Trypsin was set as the enzyme and a maximum of two missed cleavages were allowed. Protein N-terminal acetylation, methionine oxidation, and N-terminal conversion of glutamine to pyroglutamic acid were selected as variable modifications. In addition, three defined modifications on uncleaved lysines were chosen, including alkene ($C_3H_2O$, +54 Da), sulfenic acid ($C_3H_4O_2S$, +104 Da), and thiol ($C_3H_2SO$, +86 Da) modifications due to remnants of the cross-linker (FIG. 1). Initial acceptance criteria for peptide identification required a reported expectation value ≤0.05. For the 20S proteasome analysis, the false positive rate for peptide identification is less than 1%.

Figure 2:
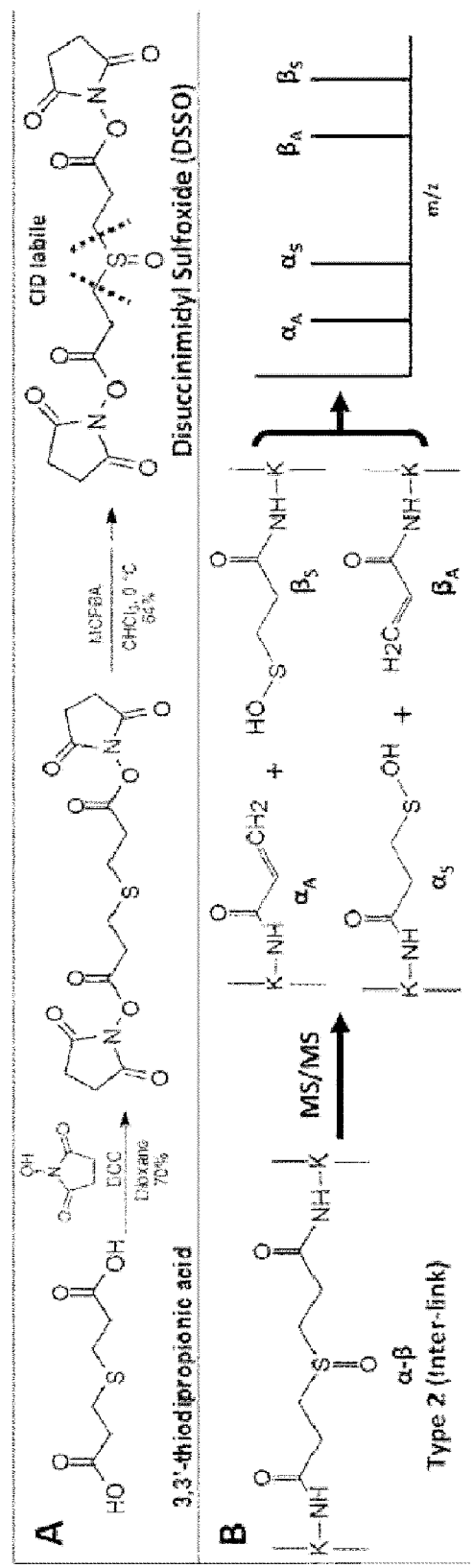
FIG. 2 shows proposed fragmentation schemes of DSSO-cross-linked peptides. A, DSSO synthesis and structure. B-D, MS/MS fragmentation patterns of the three types of DSSO-cross-linked peptides: interlinked (B), dead end (C), and intralinked (D). E, conversion of a sulfenic acid-modified fragment to an unsaturated thiol-modified fragment after a water loss. F, mass relationships between MS/MS fragment ions shown in B-D and their parent ions. DCC, N,N'-dicyclohexylcarbodiimide; MCPBA, m-chloroperbenzoic acid.
Figure 2:
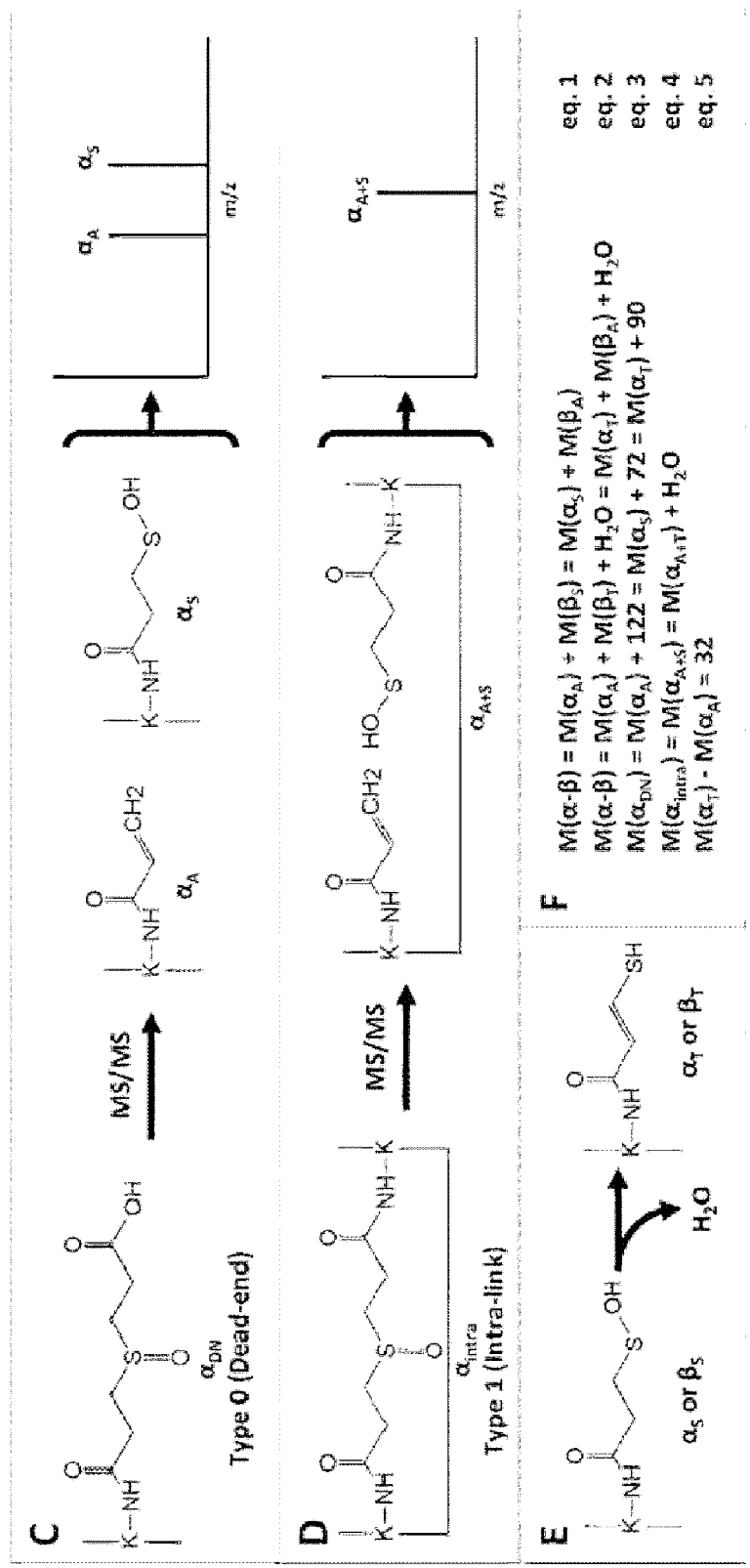
Figure 3:
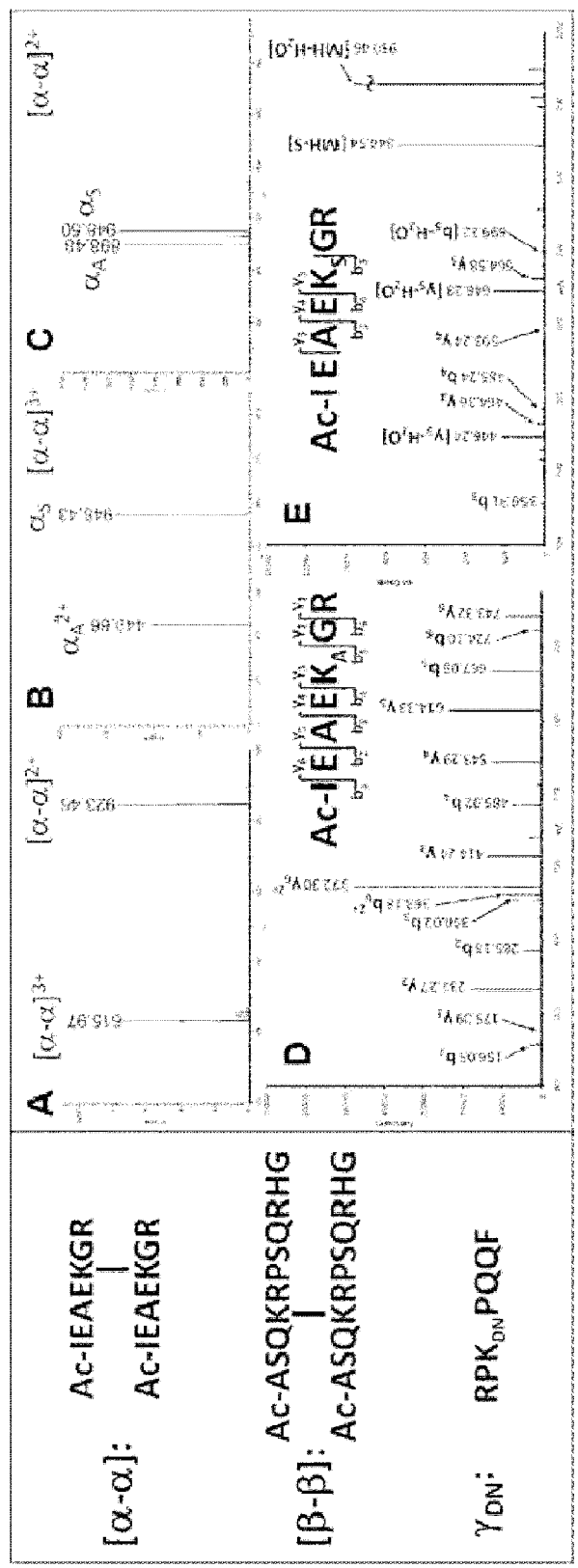
FIG. 3 is an exemplary $MS^n$ analysis of DSSO-cross-linked model peptides. A-E, $MS^n$ analysis of the DSSO-interlinked Ac-IR7 (α-α). A, MS spectrum of α-α: $[α-α]^{3+}$ (m/z $615.97^3$) and $[α-α]^{2+}$ (m/z $923.46^{2+}$). B and C, MS/MS spectra of $[α-α]^{3+}$ (B) and $[α-α]^{2+}$ (C) in which alkene ($α_A$) and sulfenic acid ($α_S$) fragments were detected. D and E, $MS^3$ spectra of $α_A$ (m/z $449.66^{2+}$) (D) and $α_S$ (m/z 948.43) (E). F-I, $MS^n$ analysis of DSSO-interlinked Ac-myelin (β-β). F, MS spectrum of β-β: $[β-β]^{6+}$ (m/z $458.23^{6+}$), $[β-β]^{5+}$ (m/z $549.68^5$), and $[β-β3]^{4+}$ (m/z $686.84^{4+}$). G-I, MS/MS spectra of $[β-β]^{6+}$ in which $β_A/β_T$ pair was observed (G), $[β-β]^{5+}$ in which the $β_A/β_S$ pair was observed (H), and $[β-β]^{4+}$ in which $β_A/α_S$ pair was observed (I). J-L, $MS^n$ analysis of DSSO dead end-modified substance P peptide $γ_{DN}$. J, MS spectrum of $γ_{DN}$ (m/z $538.76^{2+}$). K, MS/MS spectrum of $γ_{DN}$ in which two fragments, $γ_A$ (m/z $478.03^{2+}$) and $γ_s$ (m/z $502.95^{2+}$), were detected. L, $MS^3$ spectrum of $γ_A$ (m/z $478.03^{2+}$). Sequences of Ac-IR7, Ac-myelin, and substance P are Ac-IEAEKGR, Ac-ASQKRPSQRHG, and RPKPQQF, respectively.
Figure 3:
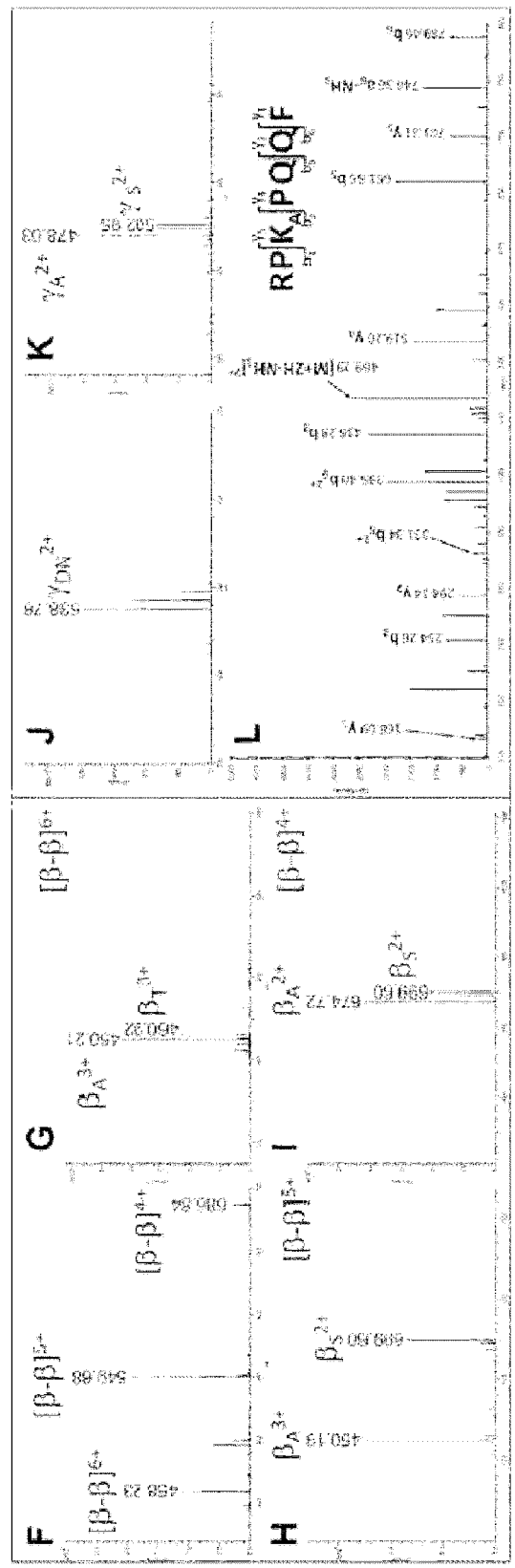

The Link-Finder program (http://www.ics.uci.edu/~baldig/Link-Finder/) was developed to search MS/MS data and identify the list of putative DSSO inter-linked and dead-end products based on their unique MS fragmentation patterns as illustrated in FIG. 2 (details see results section). For example, one embodiment of the invention includes identifying the MS/MS data that display characteristic fragmentation profiles of DSSO cross-linked peptides based on the unique mass relationships between parent ions of cross-linked peptides and their fragment ions to obtain an MS/MS result including a list of parent ions corresponding to cross-linked peptide candidates (e.g., the putative or potential identities of the cross-linked peptides being analyzed). In one embodiment, analysis of the MS/MS data is carried out using the Link-Finder program. Monoisotopic masses and charges of parent ions measured in MS scans for those putative cross-linked peptides identified by the Link-Finder program were subsequently submitted to MS-Bridge to determine cross-linked peptide sequences by mass mapping with a given cross-linker (i.e. DSSO) and protein sequences (see Chu, F., et al.). For example, one embodiment of the invention further includes mass mapping the MS data using the list of parent ions corresponding to the cross-linked peptide candidates and the MS-cleavable cross-linker againt known protein sequences to obtain an MS result comprising possible cross-linked peptide sequences. In one embodiment, the mass mapping is carried out using MS-Bridge. The parent mass error for MS-Bridge search was set as ±10 ppm and only one cross-link was allowed in the cross-linked peptides for general search. All of the three types of the cross-linked peptides (Schilling, B., et al.), i.e. inter-linked (type 2), intra-linked (type 1) and dead-end modified (type 0), can be computed and matched in MS-Bridge (see Chu, F., et al.).

The search results from Link-Finder, Batch-Tag and MS-Bridge programs are integrated together using in-house scripts to compile a list of cross-linked peptides identified with high confidence. The final results were validated manually by examining MS/MS spectra and MS$^3$ spectra respectively.

Results

Development of a Novel Sulfoxide Containing MS-Cleavable Cross-Linker—

In order to develop a robust MS-cleavable cross-linking reagent, the incorporated MS-labile bond must have the ability to selectively and preferentially fragment prior to peptide backbone breakage independent of peptide charges and sequences. It is well documented that methionine sulfoxide containing peptides have preferential fragmentation at the C—S bond adjacent to the sulfoxide during collision induced dissociation (CID) analysis (see Reid, G. E., Roberts, K. D., Kapp, E. A., and Simpson, R. I. (2004) Statistical and Mechanistic Approaches to Understanding the Gas-Phase Fragmentation Behavior of Methionine Sulfoxide Containing Peptides. *J Proteome Res* 3, 751-759), and this fragmentation is dominant and much more labile than peptide bonds. Such labile fragmentation has often been observed as the loss of 64 Da (—SOCH$_4$) from oxidized methionine containing peptides in our routine peptide analysis. Therefore, the inventors expect that if a sulfoxide is incorporated in the spacer region of a NHS ester, the C—S bond adjacent to the sulfoxide will be MS-labile and prone to preferential fragmentation. To test this, the inventors have designed and synthesized a CID cleavable cross-linker having a general formula of 3,3'-sulfinylbispropanoic acid, also known as 3,3-'sulfonyldipropanoic acid. The molecular formula is $C_6H_{10}O_5S$, and it has a general structure as shown in General Structure 2 of FIG. 1 where X==—OH. The molecular formula is $C_6H_{10}O_5S$, and it has a general structure as shown in General Structure 2 of FIG. 1 where X=—OH. More specific cleaving agents are as shown in FIG. 1 including Compound 1, namely Disuccinimidyl Sulfoxide (sometimes hereinafter referred to as "DSSO"), which is one exemplary compound of the invention. Other compounds where the X in the General Structure 2 are substituted are shown as Compounds 3-6 in FIG. 1. Hereinafter, while reference is made to DSSO, other MS-cleavable cross-linker having the general, structure as shown in General Structure 2 of FIG. 1 are included as MS-cleavable cross-linkers of invention. Turning back to disuccinimidyl sulfoxide (DSSO), it contains two NHS ester functional groups and two symmetric MS-labile C—S bonds adjacent to the sulfoxide (FIG. 2A). DSSO has a spacer length of 10.1 Å, making it well suited for detecting protein interaction interfaces of protein complexes and generating highly informative distance constraints. In comparison to existing MS-cleavable cross-linkers, DSSO can be easily synthesized in a two-step process as shown in FIG. 2A.

Proposed CID Fragmentation Pattern of DSSO Cross-Linked Peptides—

Three types of cross-linked peptides can be formed during the cross-linking reaction: inter-linked (type 2), intra-linked (type 1) and dead-end (type 0) modified peptides (Schilling, B., et al.), among which inter-linked peptides are the most informative for generating distance constraints. FIGS. 2B-D shows the proposed fragmentation schemes of DSSO cross-linked peptides. As shown in FIG. 2B, during CID analysis of a DSSO inter-linked peptide α-β, the cleavage of one C—S bond next to the sulfoxide separates the inter-linked peptide into a pair of peptide fragments, i.e. $\alpha_A/\beta_S$, in which the α peptide fragment is modified with the alkene (A) moiety (+54 Da) and the β peptide fragment is modified with the sulfenic acid (S) moiety (+104 Da). If peptides α and β have different sequences, two possible pairs of fragments (i.e. $\alpha_A/\beta_S$ and $\alpha_S/\beta_A$) will be observed due to the breakage of either of the two symmetric C—S bonds next to the sulfoxide in the spacer region of DSSO (FIG. 2B), thus resulting in four individual peaks in the MS/MS spectrum. But if peptides a and β have the same sequences, only one fragment pair, i.e. two peaks, will be detected in the MS/MS spectrum. To determine sequences of inter-linked peptides and assign the cross-linking site, the resulting peptide fragments (i.e. $\alpha_A$, $\beta_S$, $\alpha_S$, or $\beta_A$) generated in MS/MS can be further subjected to LTQ-Orbitrap XL MS for MS$^3$ analysis. Because these fragments represent single peptide sequences, the interpretation of the MS$^3$ spectra by Batch-Tag program in Protein Prospector is identical to the identification of a single peptide with a defined modification (remnant of the cross-linker). This will dramatically simplify data interpretation and improve the identification accuracy of cross-linked products.

DSSO dead-end modified peptides have a defined mass modification (+176 Da) due to the half-hydrolyzed DSSO (FIG. 2C). MS/MS analysis of a dead-end modified peptide $\alpha_{DN}$ would result in two possible fragment ions, i.e. $\alpha_A$ and $\alpha_S$, due to the cleavage of the C—S bond on either side of the sulfoxide. The inventors name the $\alpha_A$ and $\alpha_S$ fragments as the dead end fragment pair and the mass difference between these fragments correlates to the difference between the remnants of DSSO attached to the fragments. Similarly, intra-linked peptides (e.g. $\alpha_{intra}$) also have a defined mass modification (+158 Da) due to DSSO cross-linking of two distinct lysines in the same peptide sequence (FIG. 2D). The cleavage of the C—S bond will result in only one fragment peak in MS/MS with the same mass as the parent ion observed in MS. MS$^3$ analysis of fragment ions detected in MS/MS will lead to the detection of y or b ions containing either alkene (A) or sulfenic acid (S) modifications.

As shown in FIG. 2E, the sulfenic acid containing fragment (e.g. $\alpha_S$, $\beta_S$, or $\alpha_{A+S}$) may undergo further fragmentation and lose a water molecule (−18 Da) to generate a new fragment containing an unsaturated thiol (T) moiety (+86 Da) (e.g. $\alpha_T$, $\beta_T$, or $\alpha_{A+T}$). The inventors do not expect any complication with data analysis as the thiol-containing fragment ion will become the dominant ion instead of the sulfenic acid modified fragment ion in the MS/MS spectrum. Thus the inventors anticipate that the total number of pairs and peaks will remain similar as shown in FIGS. 2B-D. Due to specific and unique MS/MS fragmentation patterns for different types of DSSO cross-linked peptides, there are fixed mass relationships between parent ions and their fragment ions as listed in FIG. 2F. For DSSO inter-linked peptides (α-β), the mass sum of each fragment pair ($\alpha_A/\beta_S$ or $\alpha_S/\beta_A$) is equivalent to the mass of the parent ion (FIG. 2F, Eq. 1). If $\alpha_S$ or $\beta_S$ loses a water and becomes $\alpha_T$ or $\beta_T$ respectively, the fragment pairs will be $\alpha_A/\beta_T$ and $\alpha_T/\beta_A$ and the mass sum of each fragment pair plus a water will be the same as the parent mass (FIG. 2F, Eq. 2). As for the dead-end (DN) modified peptide $\alpha_{DN}$, each fragment (i.e. $\alpha_A$, $\alpha_S$ or $\alpha_T$) has a distinct mass difference from the parent ion (FIG. 2F, Eq. 3). For the intra-link peptide aintra, the fragment mass could be either the same as the parent mass (i.e. $\alpha_{A+S}$), or 18 Da less than the parent mass (i.e. $\alpha_{A+T}$) (FIG. 2F, Eq. 4). Moreover, there is a definite mass difference (Δ32 Da) between the thiol (T) and alkene (A) modified forms of the same sequence (FIG. 2F, Eq. 5). These characteristic mass relationships have been incorporated into the Link-Finder program to identify DSSO cross-linked peptides.

Data Analysis of DSSO Cross-linked Peptides—Monoisotopic masses of parent ions and corresponding fragment ions, parent ion charge states and ion intensities from LC MS/MS and LC MS$^3$ spectra were extracted using in-house software based on Raw_Extract script from Xcalibur v2.4 (Thermo Scientific, San Jose, Calif.). Database searching was performed with a developmental version of Protein Prospector (v. 5.5.0, University of California, San Francisco) using its software suite, i.e. Batch-Tag and MS-Bridge as described in Chu, F., et al. Using in-house scripts, extracted MS$^3$ data were reformatted such that MS$^3$ fragment ions were directly linked to their MS/MS parent ions. For cytochrome c (P62894) and ubiquitin (P62990) analyses, database searching of MS$^3$ spectra was performed using Batch-Tag against their accession numbers in SwissProt.2009.09.01 database. For the 20S proteasome, Batch-Tag search of MS$^3$ data was performed against a decoy database consisting of a normal SGD yeast database concatenated with its reversed version (total 13490 protein entries). The mass tolerances for parent ions and fragment ions were set as ±20 ppm and 0.6 Da, respectively. Trypsin was set as the enzyme and a maximum of two missed cleavages were allowed. Protein N-terminal acetylation, methionine oxidation, and N-terminal conversion of glutamine to pyroglutamic acid were selected as variable modifications. In addition, three defined modifications on uncleaved lysines were chosen, including alkene ($C_3H_2O$, +54 Da), sulfenic acid ($C_3H_4O_2S$, +104 Da), and thiol ($C_3H_2SO$, +86 Da) modifications due to remnants of the cross-linker (FIG. 1). Initial acceptance criteria for peptide identification required a reported expectation value ≤0.05. For the 20S proteasome analysis, the false positive rate for peptide identification is less than 1%.

The Link-Finder program was developed to search MS/MS data and identify the list of putative DSSO inter-linked and dead—end products based on their unique MS fragmentation patterns as illustrated in FIG. 2 (details see results section).

For example, one embodiment of the invention includes identifying the MS/MS data that display characteristic fragmentation profiles of DSSO cross-linked peptides based on the unique mass relationships between parent ions of cross-linked peptides and their fragment ions to obtain an MS/MS result including a list of parent ions corresponding to cross-linked peptide candidates (e.g., the putative or potential identities of the cross-linked peptides being analyzed). In one embodiment, analysis of the MS/MS data is carried out using the Link-Finder program. Monoisotopic masses and charges of parent ions measured in MS scans for those putative cross-linked peptides identified by the Link-Finder program were subsequently submitted to MS-Bridge to determine cross-linked peptide sequences by mass mapping with a given cross-linker (i.e. DSSO) and protein sequences (see Chu, F., et al.). For example, one embodiment of the invention further includes mass mapping the MS data using the list of parent ions corresponding to the cross-linked peptide candidates and the MS-cleavable cross-linker against known protein sequences to obtain an MS result comprising possible cross-linked peptide sequences. In one embodiment, the mass mapping is carried out using MS-Bridge. The parent mass error for MS-Bridge search was set as ±10 ppm and only one cross-link was allowed in the cross-linked peptides for general search. All of the three types of the cross-linked peptides (Schilling, B., et al.), i.e. inter-linked (type 2), intra-linked (type 1) and dead-end modified (type 0), can be computed and matched in MS-Bridge (see Chu, F., et al.).

Characterization of DSSO Cross-Linked Peptides of Model Proteins by MS$^n$ Analysis—

Figure 4:
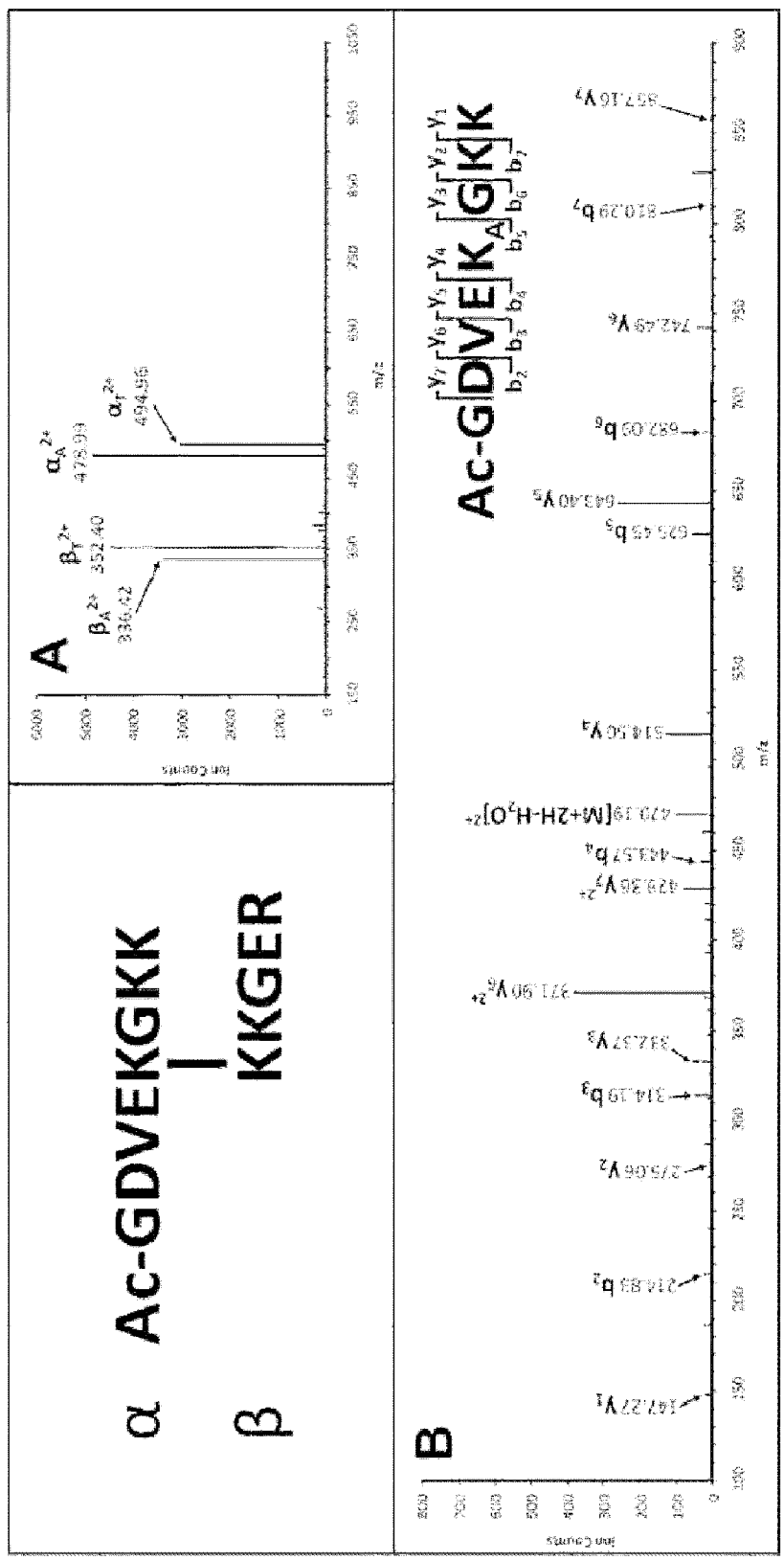
FIG. 4 is an exemplary $MS^n$ analysis of DSSO heterodimeric interlinked peptide of cytochrome c (α-β: Ac-GDVEKGKK interlinked to KKGER). A, MS/MS spectrum of $[α-β]^{4+}$ (m/z $419.9716^{4+}$) in which two fragment pairs were observed: $α_A$ (m/z $478.99^{2+}$)/$β_T$(m/z $352.40^{2+}$) and $α_T$ (m/z $494.96^{2+}$/$β_A$ (m/z $336.42^{2+}$). B, $MS^3$ spectrum of $α_A$ (m/z $478.99^{2+}$) in which detection of $y_1$-$y_7$ and $b_2$-$b_7$ determined the sequence unambiguously as Ac-GDVEK$_A$GKK. C, $MS^3$ spectrum of $β_T$ (m/z $352.40^{2+}$) in which detection of $y_1$-$y_4$, $a_1$, and $b_2$-$b_7$ ions determined the sequence unambiguously as K$_T$KGER. K$_A$ is modified with the alkene moiety, and K$_T$ is modified with the unsaturated thiol moiety.
Figure 4:
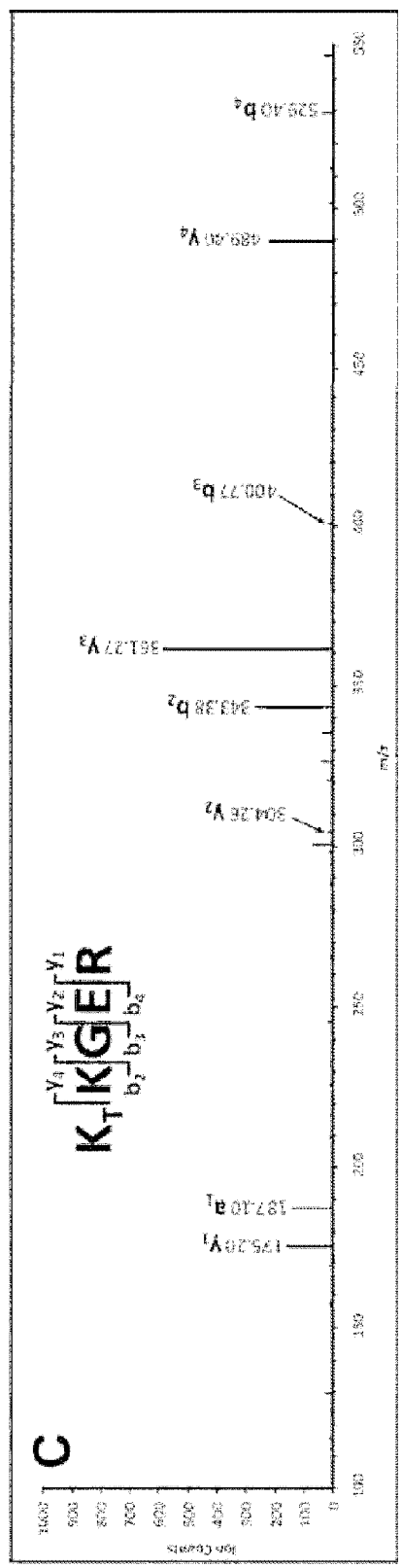

The inventors next evaluated the applicability of DSSO for protein cross-linking under physiological conditions. Model proteins cytochrome c (see for previously described Sinz, A. (2003); Kasper, P. T., et al.; Nessen, M. A., et al.; Vellucci, D., et al.; Lee, Y. J., et al.; Pearson, K. M., Pannell, L. K., and Fales, H. M. (2002) Intramolecular Cross-Linking Experiments on Cytochrome C and Ribonuclease a Using an Isotope Multiplet Method. *Rapid Commun. Mass Spectrom.* 16, 149-159; Dihazi, G. H., and Sinz, A. (2003) Mapping Low-Resolution Three-Dimensional Protein Structures Using Chemical Cross-Linking and Fourier Transform Ion-Cyclotron Resonance Mass Spectrometry. 17, 2005-2014; and Guo, X., Bandyopadhyay, P., Schilling, B., Young, M. M., Fujii, N., Aynechi, T., Guy, R. K., Kuntz, I. D., and Gibson, B. W. (2008) Partial Acetylation of Lysine Residues Improves Intraprotein Cross-Linking. *Anal Chem* 80, 951-960) and ubiquitin (Chowdhury, S. M., et al.; and Gardner, M. W., et al.) have been extensively utilized to test various new cross-linking strategies since they have a relatively large number of lysine residues accessible for cross-linking. Based on our previous work (see Vellucci, D., et al.), cytochrome c was cross-linked with a 10-fold excess of DSSO. The cytochrome c cross-linking efficiency using DSSO was comparable to the efficiency using DSG or our previously developed Azide-DSG cross-linkers (see Vellucci, D., et al.), indicating that DSSO is as effective for protein cross-linking reactions. The DSSO cross-linked cytochrome c was then digested with trypsin and analyzed by LC MS$^n$. Three types of cross-linked peptides of cytochrome c (i.e. inter-link, intra-link and dead-end) have been observed. FIG. 4A displays the MS/MS spectrum of a tryptic peptide of cytochrome c with m/z 419.9716$^{4+}$, in which only four abundant fragment ions (m/z 336.42$^{2+}$, 352.40$^{2+}$, 478.99$^{2+}$, 494.96$^{2+}$) were detected, suggesting this peptide as a potential heterodimeric inter-linked peptide (α-β). Two possible fragment pairs, $\alpha_A/\beta_{S/T}$ and $\alpha_{S/T}/\beta_A$ are thus expected, in which S/T means either S (sulfenic) or T (unsaturated thiol) containing fragment ions will be observed.

Using the mass relationship between the pairs and the parent ion of inter-linked peptides (Eqs. 1, 2, 5 in FIG. 2F), the inventors identified two fragment pairs as $\alpha_A/\beta_T$ (478.99$^{2+}$/352.40$^{2+}$) and $\alpha_T/\beta_A$ (494.96$^{2+}$+1336.42$^{2+}$), confirming that this peptide is a heterodimeric inter-linked peptide (α-β). Mass mapping of the parent ion (m/z 419.9716$^{4+}$) by MS-Bridge revealed that it matches to an inter-linked peptide [Ac-GDVEKGKK inter-linked to KKGER] with an error of 0.48 ppm. The fragment ions $\alpha_A$ (m/z 478.99$^{2+}$) and $\beta_T$ (m/z 352.40$^{2+}$) were further subjected to MS$^3$ sequencing and their MS$^3$ spectra are illustrated in FIGS. 4B-C. Based on the series of y (i.e. y$_{1-7}$) and b (i.e. b$_{2-7}$) ions, the sequence of the MS/MS fragment ion $\alpha_A$ (m/z 478.99$^{2+}$) was unambiguously identified as Ac-GDVEK$_A$GKK, in which K (Lys) at 5th position from N-terminus was determined to be modified with the alkene moiety. MS$^3$ analysis of the corresponding fragment pair ion $\beta_T$ (m/z 352.40$^{2+}$) determined its sequence as K$_T$KGER. Although there are two lysine residues in the sequence, occurrence of y$_4$ and a$_1$ ions indicates that the first N-terminal K is modified with an unsaturated thiol moiety. Taken together, the identity and cross-linking site of the inter-link peptide [Ac-GDVEKGKK inter-linked to KKGER] was determined unambiguously.

Figure 5:
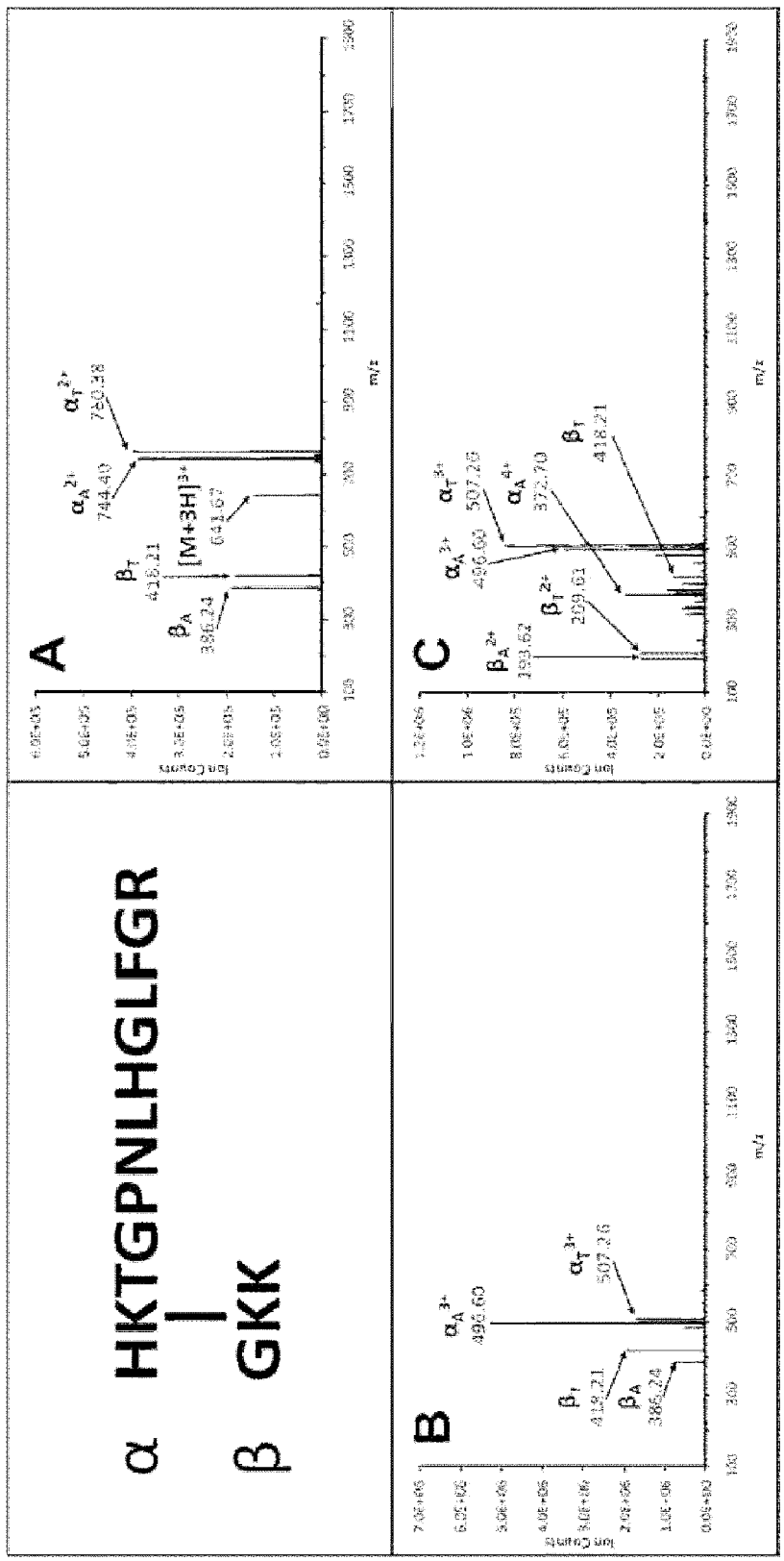
FIG. 5 is an exemplary $MS^n$ analysis of DSSO heterodimeric interlinked peptide of cytochrome c (α-β: HKT-GPNLHGLFGR interlinked to GKK). This peptide was detected in MS as triply charged $[α-β]^{3+}$ (m/z $641.6730^{3+}$), quadruply charged $[α-β]^{4+}$ (m/z $481.5069^{4+}$), and quintuply charged $[α-β]^{5+}$ (m/z $385.4070^{5+}$) ions. A, MS/MS spectrum of $[α-β]^{3+}$ (m/z $641.6730^{3+}$) in which two fragment pairs were observed: $α_A$ (m/z $744.40^{2+}$)/$β_T$ (m/z 418.21) and $α_T$ (m/z $760.38^{2+}$)/$β_A$ (m/z 386.24). B, MS/MS spectrum of $[α-β]^{4+}$ (m/z $481.5069^{4+}$) in which two fragment pairs were observed: $α_A$ (m/z $496.60^{3+}$)/$β_T$ (m/z 418.21) and $α_T$ (m/z $507.26^{3+}$)/$β_A$ (m/z 386.24). C, MS/MS spectrum of $[α-β]^{5+}$ (m/z $385.4070^{5+}$) in which two fragment pairs were observed: $α_A/β_T$ (m/z $496.60^{3+}/209.61^{2+}$ and $372.70^{4+}/$ 418.21) and $α_T$ (m/z $507.26^{3+}$)/$β_A$ (m/z $193.62^{2+}$). D, $MS^3$ spectrum of $α_A$ fragment (m/z $496.60^{3+}$) in which detection of a series of y and b ions determined its sequence unambiguously as HK$_A$TGPNLHGLFGR. K$_A$ is modified with the alkene moiety.
Figure 5:
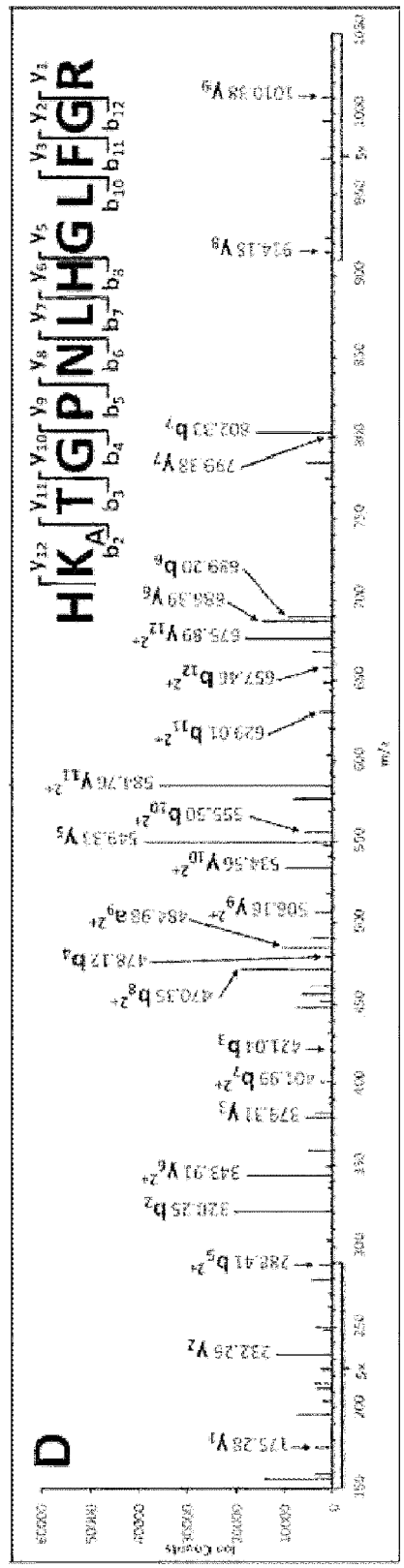

FIGS. 5A-C display MS/MS spectra of triply (m/z 641.6730$^{3+}$), quadruply (m/z 481.5069$^{4+}$), and quintuply (m/z 385.4070$^{5+}$) charged ions of a cytochrome c cross-linked peptide. The MS/MS spectrum of the triply charged ion (m/z 641.6730$^{3+}$) resulted in four dominant fragment ions (m/z 386.24, 418.21, 744.40$^{2+}$, 760.38$^{2+}$), which have been determined as the two fragment pairs $\alpha_A/\beta_T$ (744.40$^{2+}$/418.21) and $\alpha_T/\beta_A$ (760.38$^{2+}$/386.24), indicating this peptide is a heterodimeric inter-linked peptide. The same characteristic fragment pairs, i.e. $\alpha_A/\beta_T$ and $\alpha_T/\beta_A$ have also been identified but with different charges in the MS/MS spectra of the quadruply (m/z 481.5069$^{4+}$) and quintuply (m/z 385.4070$^{5+}$) charged parent ions respectively (FIGS. 5B-C). It is noted that some charge distribution of fragment ions was observed in the pairs (FIG. 5C) due to the high charge state of the parent ion. Nevertheless, the dominant ions are the characteristic fragment ions of the inter-linked peptide. MS$^3$ analysis of the $\alpha_A$ (m/z 496.60$^{3+}$) fragment has revealed its sequence identity unambiguously as HK$_A$TGPNLHGLFGR, in which the K (Lys) at position 2 from N-terminus was modified with the alkene moiety (FIG. 5D). In combination with the MS-Bridge result, the inter-linked peptide is identified as [HKTGPNLHGLFGR inter-linked to GKK]. These results demonstrate that preferred fragmentation of the C—S bonds in DSSO inter-linked peptides of cytochrome c occurs as expected and is independent of peptide charge states and sequences.

Figure 6:
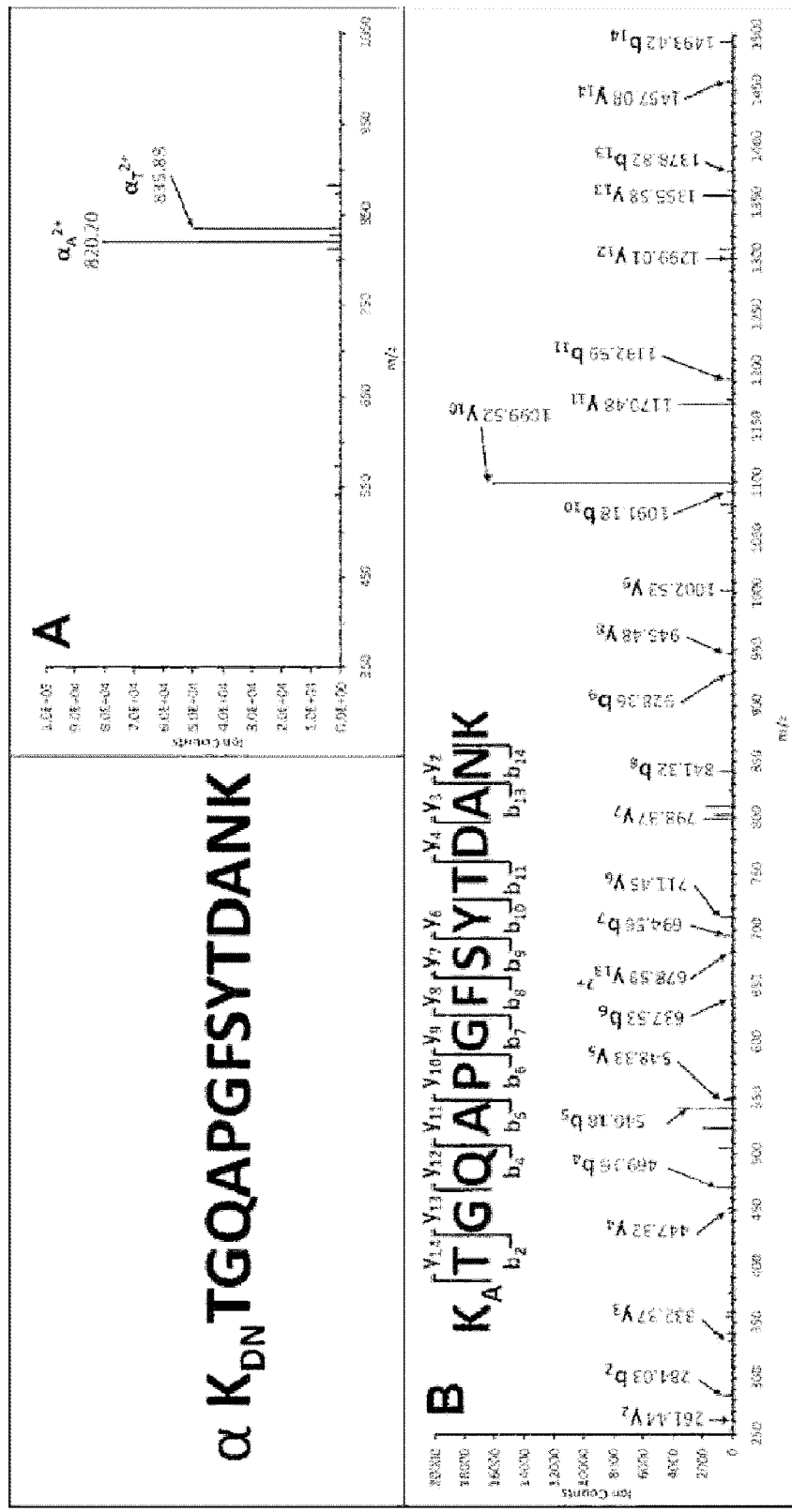
FIG. 6 is an exemplary $MS^n$ analysis of DSSO dead end-modified peptide (A and B) and intralinked peptide of cytochrome c (C and D). A, MS/MS spectrum of a dead end-modified peptide ($α_{DN}$; m/z $880.8975^{2+}$, K$_{DN}$TGQAPGFSYTDANK) in which two fragment ions were determined as $α_A$ (m/z $820.20^{2+}$) and $α_T$ (m/z $835.88^{2+}$). B, $MS^3$ spectrum of $α_A$ (m/z $820.20^{2+}$) in which detection of a series of y and b ions determined its sequence unambiguously as K$_A$TGQAPGFSYTDANK. C, MS/MS spectrum of an intralinked peptide ($α_{intra}$; m/z $611.9802^{3+}$, GGK*HK*TGPNLHGLFGR) in which one fragment ion was observed and determined as $α_{A+T}$ (m/z $606.24^3$). D, $MS^3$ spectrum of $α_{A+T}$ (m/z $606.24^{3+}$) in which detection of a series of y and b ions determined the presence of a mixture of GGK$_A$HK$_T$TGPNLHGLFGR and GGK$_T$HK$_A$TGPNLH-GLFGR. K$_A$ is modified with the alkene moiety, and K$_T$ is modified with the unsaturated thiol moiety.
Figure 6:
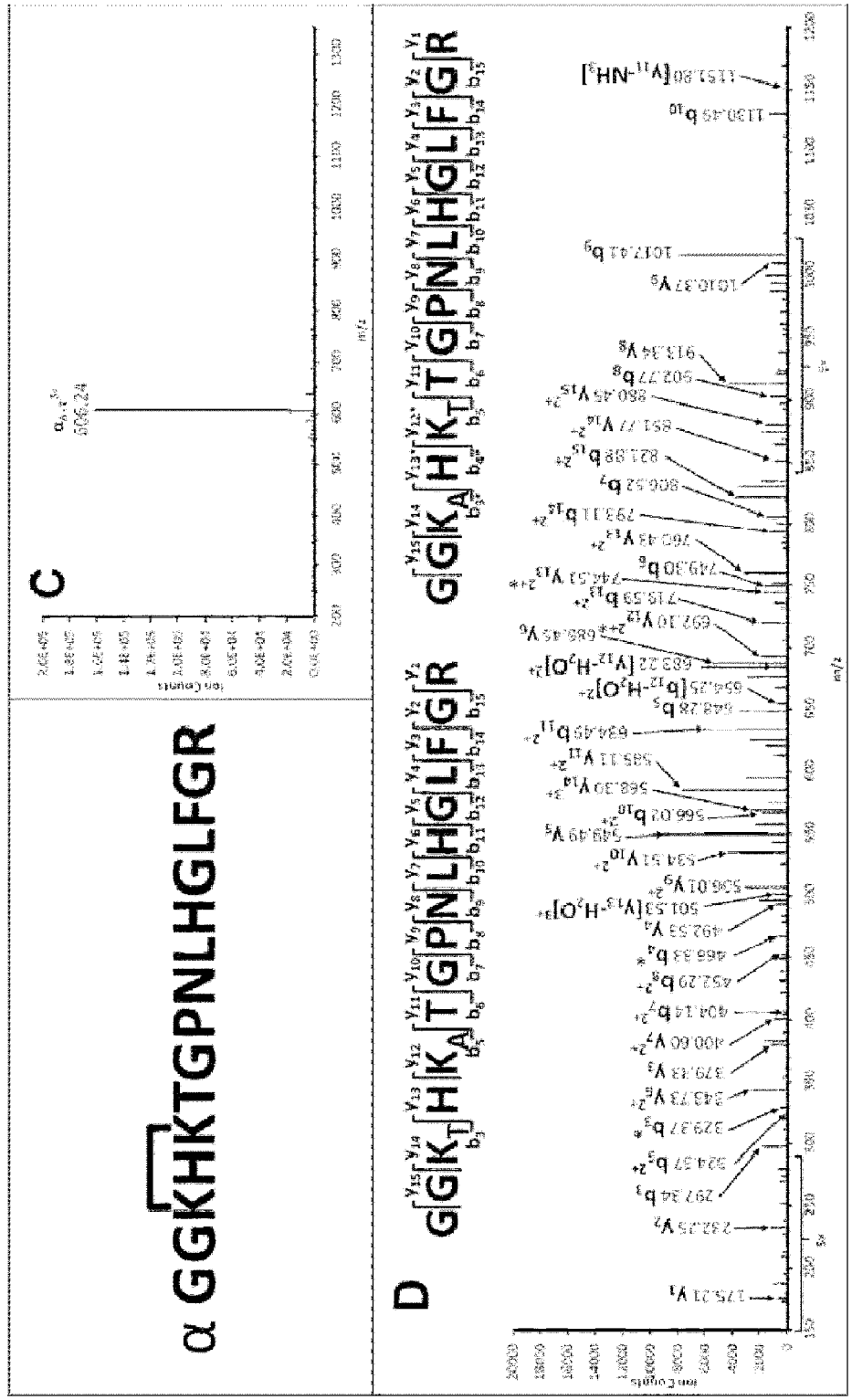

To understand how dead-end modified peptides of cytochrome c behave in MS$^n$ analysis, FIG. 6A illustrates the MS/MS spectrum of a selected dead-end modified peptide (m/z 880.8975$^{2+}$). As shown, two major fragment ions (m/z 820.20$^{2+}$ and 835.88$^{2+}$) were detected and they are 122 and 90 Da less than the parent ion respectively. Such mass differences between the parent ion and its fragment ions fit well with those predicted for DSSO dead-end modified peptides (eq. 3 in FIG. 2F), identifying the ion m/z 820.20$^{2+}$ as $\alpha_A$ and 835.88$^{2+}$ as $\alpha_T$ fragment. MS$^3$ analysis of the $\alpha_A$ fragment (m/z 820.20$^{2+}$) (FIG. 6B) as well as the MS-Bridge result of the parent ion (m/z 880.8975$^{2+}$) identified its sequence as K$_{DN}$TGQAPGFSYTDANK.

As discussed above (FIG. 2D), the inventors predict that MS/MS analysis of the intra-linked peptide ($\alpha_{intra}$) will lead to either a fragment ion ($\alpha_{A+S}$) containing one K$_A$ (Lys$_A$) and one K$_S$ (Lys$_S$) with the same mass as the parent ion or a fragment ion ($\alpha_{A+T}$) containing one $K_A$ ($Lys_A$) and one $K_S$ ($Lys_T$) with a mass 18 Da less than the original parent ion. FIG. 6C displays the MS/MS spectrum of a cytochrome c tryptic peptide with m/z 611.9802$^{3+}$ in which only one major fragment ion (m/z 606.24$^{2+}$) was detected with a mass 18 Da less than the parent ion. This suggests that the peptide is potentially an intra-linked peptide of cytochrome c and its MS/MS fragment ion (m/z 606.24$^{2+}$) can be labeled as $\alpha_{A+T}$. Mass mapping of the parent ion m/z 611.9802$^{3+}$ using MS-Bridge matched to an intra-linked peptide, GGK*HK*TGPNLHGLFGR, where the two N-terminal K* (Lys*) are linked. Since the CID-induced C—S bond breakage can occur at either side of the sulfoxide, a mixture of two fragments with identical masses but with alkene (A) or thiol (T) moieties at either K can be generated. FIG. 6D illustrates the MS$^3$ spectrum of the MS/MS fragment ion (m/z 606.24$^{3+}$), with a series of y and b ions confirming its identity as GGK$_T$HK$_A$TGPNLHGLFGR and/or GGK$_A$HK$_T$TGPNLHGLFGR. The detection of y$_{13}$ (760.43$^{2+}$), and b$_3$ (297.34) ions indicates the presence of the peptide fragments from the sequence of GGK$_T$HK$_A$TGPNLHGLFGR, and the detection of b$_3$*(329.37), b$_4$*(466.33), y$_{12}$*(692.10$^{2+}$), and y$_{13}$* (744.51$^{2+}$) identified the peptide fragments from the GGK$_A$HK$_T$TGPNLHGLFGR sequence.

Development of an Integrated Workflow for Fast and Accurate Identification of DSSO Cross-Linked Peptides by LC MS$^n$—

Figure 7:
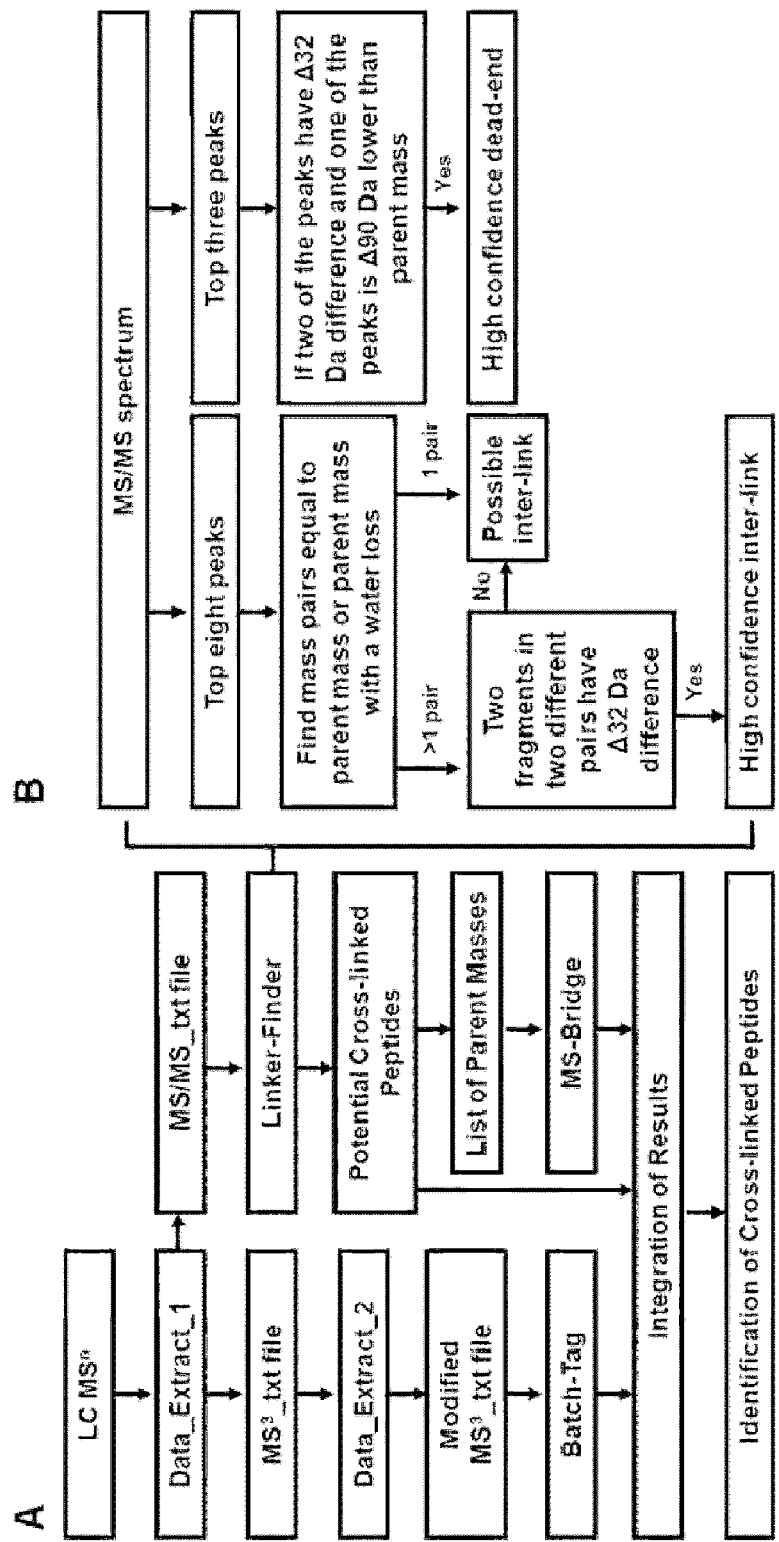
FIG. 7 shows A, the integrated data analysis work flow for identifying DSSO-crosslinked peptides by LC $MS^n$ and B, the work flow for the Link-Finder program.

In order to facilitate data analysis for the identification of DSSO cross-linked peptides from complex mixtures, the inventors have developed an integrated workflow for processing LC MS$^n$ data acquired by LTQ-Orbitrap XL MS (FIG. 7A). During LC MS$^n$ analysis, three types of data are collected, i.e. MS, MS/MS and MS$^3$ spectra, in which MS and MS/MS are acquired in FT mode to allow accurate mass measurement and charge determination of both parent ions in MS and their fragment ions in MS/MS spectra. MS$^3$ is obtained in LTQ to achieve the highest sensitivity. As shown, the first data extraction step is to generate the text files containing peak lists of MS/MS and MS$^3$ data respectively. Based on the unique MS/MS fragmentation profiles of DSSO cross-linked peptides and the defined mass relationships between parent ions and their fragment ions (FIG. 2), Link-Finder program was developed to automatically search MS/MS data to identify putative DSSO cross-linked peptides (FIG. 7B). As discussed above, the inter-linked products produce distinct MS/MS spectra with two pairs of dominant peptide fragments ($\alpha_A/\beta_{S/T}$ and $\alpha_{T/S}/\beta_A$). For each MS/MS scan, among the top eight most abundant peaks, if there is a fragment pair with a mass sum equal to their parent mass with or without a water loss (−18 Da), the parent ion will be categorized as a possible inter-linked peptide. If two of those pairs can be found, and the mass difference between any two fragments from the two distinct pairs is 32 Da, i.e., the mass difference between the thiol and alkene moieties, then it is almost certain that the parent ion is a true inter-linked product. The dead-end product typically has two major fragment ions representing the parent peptide attached with either a thiol or an alkene moiety. Among the top three peaks, if there are two peaks with mass difference of 32 Da, and one of them is 90 Da less than the parent mass, then it is categorized as a possible dead-end peptide. Using the Link-Finder program, a list of parent ions are identified as putative inter-linked or dead-end modified peptides. The generated list of parent ion masses is then subjected to MS-Bridge to identify putative cross-linked peptides of all types by mass matching with high mass accuracy (<10 ppm).

For MS$^3$ data, only the original parent ion observed in MS scan is listed as the precursor ion during database searching. In order to extract the MS$^3$ parent ion (fragment ions in MS/MS), for Batch-Tag search, the second data extraction step is carried out using in-house scripts to generate a modified MS$^3$-txt file. The Batch-Tag search result provides high confidence identification of single peptide fragments generated in MS/MS that are initially cross-linked. Finally, the results from three different types of searches, i.e. Batch-Tag (MS$^3$ data), Link-Finder (MS/MS data), and MS-Bridge (MS data) are integrated using in-house scripts within Link-Finder program to obtain accurate and reliable identification of cross-linked peptides. Among them, MS$^3$ sequencing with Batch-Tag searching is essential for unambiguous identification of cross-linking sites.

Identification of DSSO cross-linked peptides of model proteins by automated database searching—The newly developed integrated workflow was first employed to identify DSSO cross-linked peptides of cytochrome c. In total, 19 inter-linked peptides have been unambiguously identified and summarized in TABLE 1 (for details see TABLE 3 and FIG. 11). Each peptide has characteristic fragment pairs in MS/MS spectra and was identified by Link-Finder program. In addition, one or two MS/MS fragment pair ions have been sequenced by MS$^3$ to provide unambiguous identification. Moreover, all of the parent masses fit well with identified cross-linked peptides by MS-Bridge program with high mass accuracy. In comparison to reported cross-linking studies of cytochrome c (Schilling, B., et al.; Kasper, P.T. et al.; Nessen, M.A. et al.; Vellucci, D. et al.; Lee, Y.J., et al.; Pearson, K.M., et al.; Dihazi, G.H.; and Guo, X., et al.), three novel inter-links have been identified in this work. Besides the inter-linked peptides, 7 intra-linked and 8 dead-end peptides have also been identified (See TABLE 3). For the dead-end modified peptides, each has a dead-end fragment pair and at least one of the fragment ions has been sequenced, which correlates very well with MS-Bridge and Batch-Tag results. The intra-linked peptides were mainly identified by Batch-Tag and MS-Bridge results.

In addition to products with one cross-link (i.e. type 0, 1 and 2), peptides containing two cross-links have also been identified using this integrated workflow. In this work, 11 non-redundant DSSO cross-linked peptides with two links (e.g. one inter-link with one dead-end, one inter-link with one intra-link, or one intra-link with one dead-end) have been identified and summarized in TABLE 3. This type of information is not commonly reported since peptide sequencing of multi-linked peptides is highly complicated. This demonstrates the ability of our new cross-linking strategy for identifying such complex products.

Based on the crystal structure of bovine heart cytochrome c (PDB ID; 2B4Z) (44), the inventors have calculated the distances between alpha carbons of the identified cross-linked lysine residues (TABLE 1 and TABLE 3). Among the 26 non-redundant inter-linked lysines in cytochrome c identified in this work (excluding linkages between two adjacent lysines), all of the linkages have the distances between their alpha carbons within the range of 5.3 Å to 19.3 Å. This is consistent not only with the length of a fully expanded DSSO (10.1 spacer length) and two lysine side chains, but also with the previous results using similar lengths of NHS ester cross-linkers (see Vellucci, D., et al.; Lee, Y.J., et al.; Guo, X., et al.; and Kruppa, G.H., Schoeniger, J., and Young, M.M. (2003) A Top Down Approach to Protein Structural Studies Using Chemical Cross-Linking and Fourier Transform Mass Spectrometry. *Rapid Commun Mass Spectrom* 17, 155-162). The results suggest that our cross-linking conditions did not induce significant disturbance to cytochrome c structural conformations.

In addition to cytochrome c, the same strategy has been successfully applied to identify DSSO cross-linked peptides of ubiquitin. Using the same analysis strategy, 3 inter-linked, 1 intra-linked, and 5 dead-end peptides have been identified as summarized in TABLE 4 and FIG. 11. Based on the crystal structure of bovine ubiquitin (PDB ID; 1AAR), all of the identified inter-/intra-linked lysines in ubiquitin have the distances between their alpha carbons within the range of 6 to 18 Å. The identified cross-linked lysines are consistent with the known structure of ubiquitin and previous reports (Chowdhury, S. M., et al.; and Gardner, M. W., et al.) It is interesting to note that one of the identified inter-linked peptides is [LIFAGK$^{48}$QLEDGR inter-linked to LIFAGK$^{48}$QLEDGR], which is a cross-link formed between the ubiquitin dimer. Residue K$^{48}$ is located at a hydrophobic patch important for protein interactions and K$^{48}$ is also an in vivo chain linkage site for polyubiquitination required for ubiquitin/ATP dependent proteasomal degradation (Pickart, C. M., and Cohen, R. E. (2004) Proteasomes and Their Kin: Proteases in the Machine Age. *Nat Rev Mol Cell Biol.* 5, 177-187). The same K$^{48}$-K$^{48}$ (Lys$^{48}$-Lys$^{48}$) cross-link was identified previously using an alkyne-tagged NHS ester, but only after selective enrichment coupled with CID and ETD analyses (Chowdhury, S. M., et al.). In comparison, the inventors were able to identify the K$^{48}$ inter-linked peptide without any enrichment, thus further demonstrating the effectiveness of our approach to identify DSSO cross-linked peptides from complex mixtures.

Figure 8:
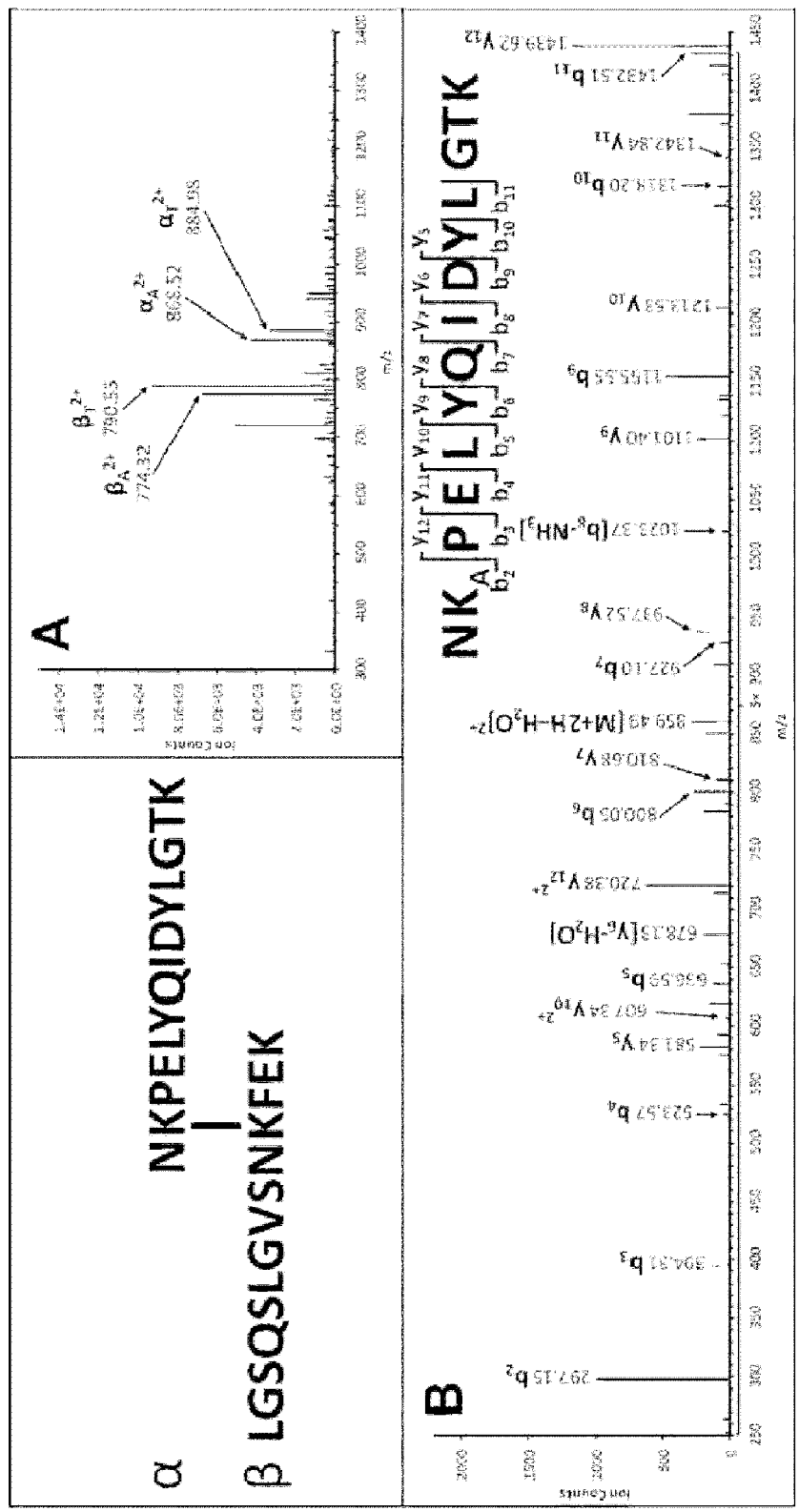
FIG. 8 is an exemplary $MS^n$ analysis of DSSO heterodimeric interlinked peptide of the yeast 20 S proteasome complex (α-β: NKPELYQIDYLGTK interlinked to LGSQS-LGVSNKFEK) with intersubunit link between 20 S subunit β4 and β3. A, MS/MS spectrum of $[α-β]^{4+}$ (m/z $833.9231^{4+}$) in which two fragment pairs were detected and determined as $α_A$ (m/z $868.52^{2+}$)/$β_T$ (m/z $790.55^{2+}$) and $α_T$ (m/z $884.98^2$)/ $β_A$ (m/z $774.32^{2+}$). B, $MS^3$ spectrum of $α_A$ (m/z $868.52^{2+}$) in which detection of a series of y and b ions determined its sequence unambiguously as NK$_A$PELYQIDYLGTK. C, $MS^3$ spectrum of $β_T$ (m/z $790.55^{2+}$) in which detection of a series of y and b ions determined its sequence unambiguously as LGSQSLGVSNK$_T$FEK. K$_A$ is modified with the alkene moiety, and K$_T$ is modified with the unsaturated thiol moiety.
Figure 8:
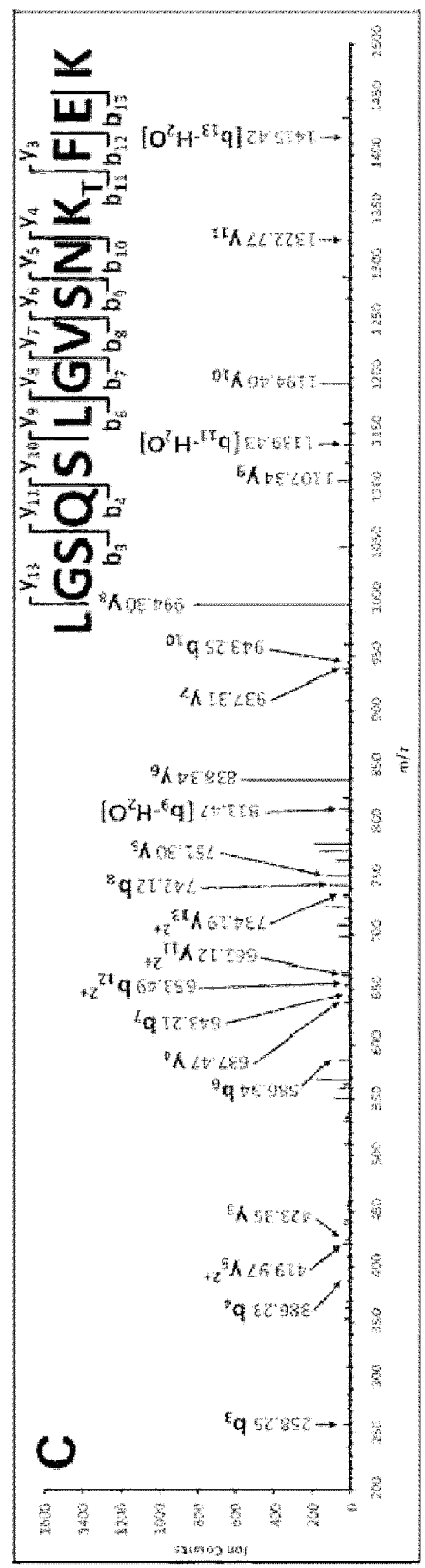
Figure 12:
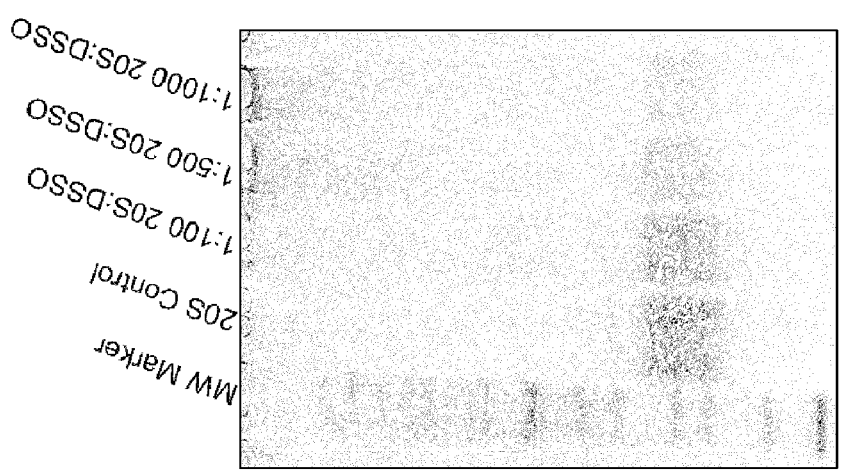
FIG. 12 is an exemplary SDS-PAGE gel picture of the 20S proteasome cross-linked with various molar ratios of cross-linker DSSO, i.e. 1:100, 1:500 and 1:1000. The 20S proteasome without cross-linking served as a control. The cross-linked proteasome complex was separated using 4-20% gradient gel.
Figure 13:
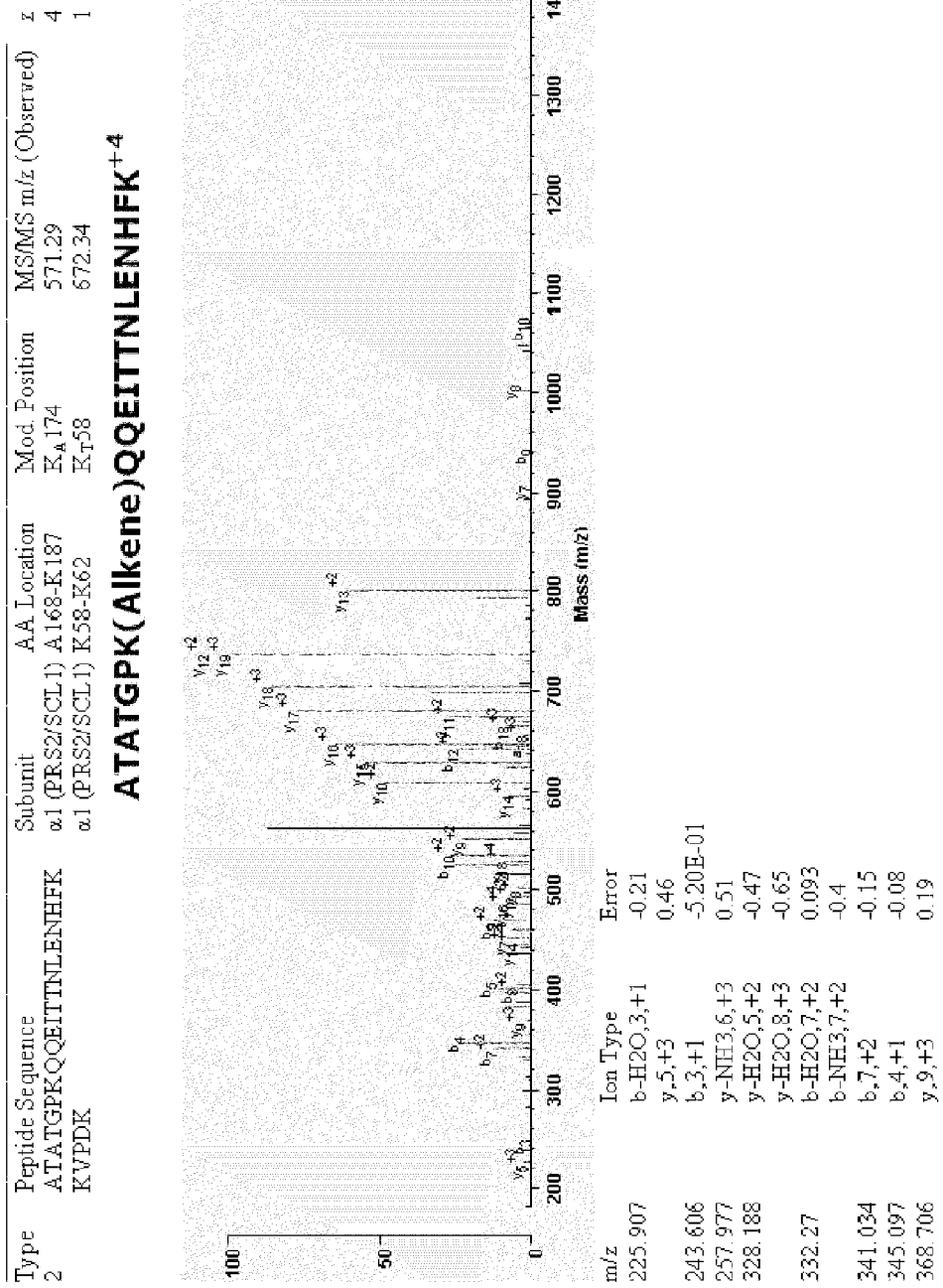
FIG. 13 is an exemplary $MS^3$ analysis of DSSO interlinked peptides of the yeast 20S proteasome complex.
Figure 13:
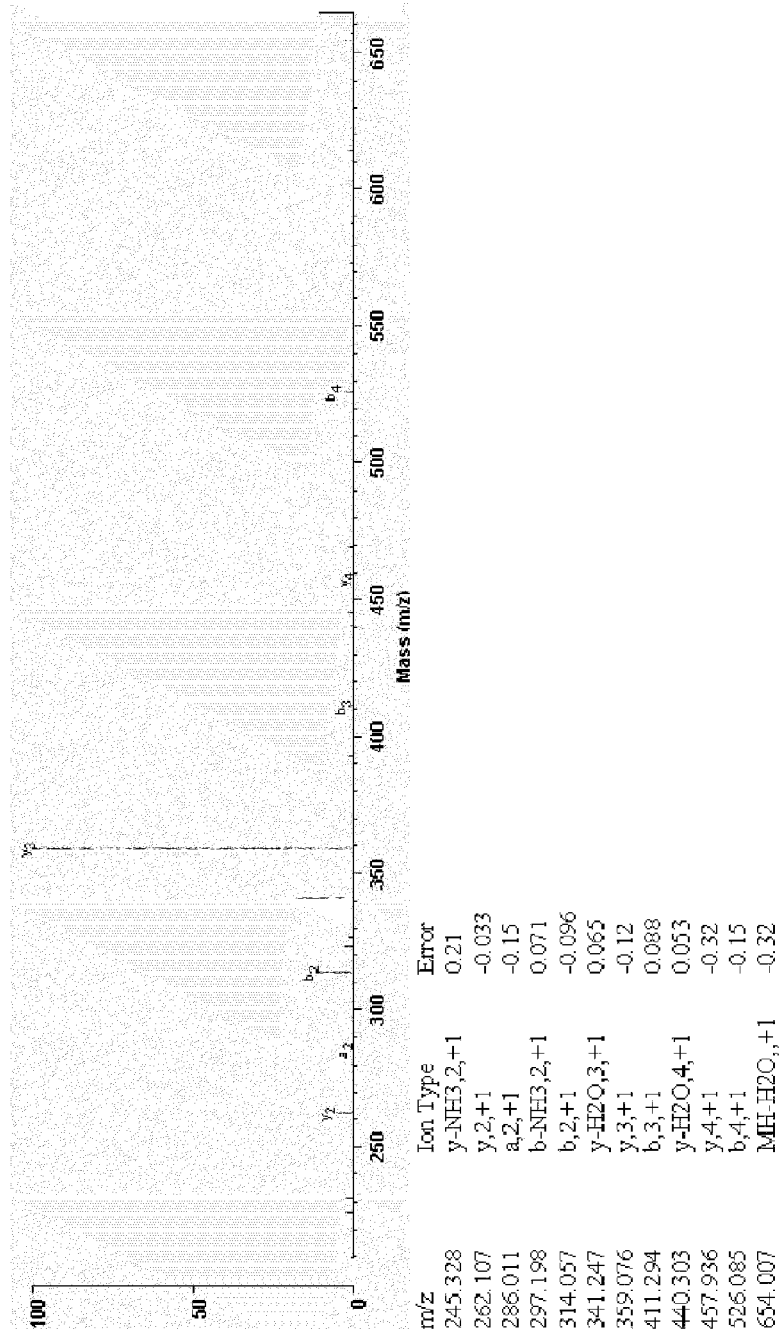
Figure 13:
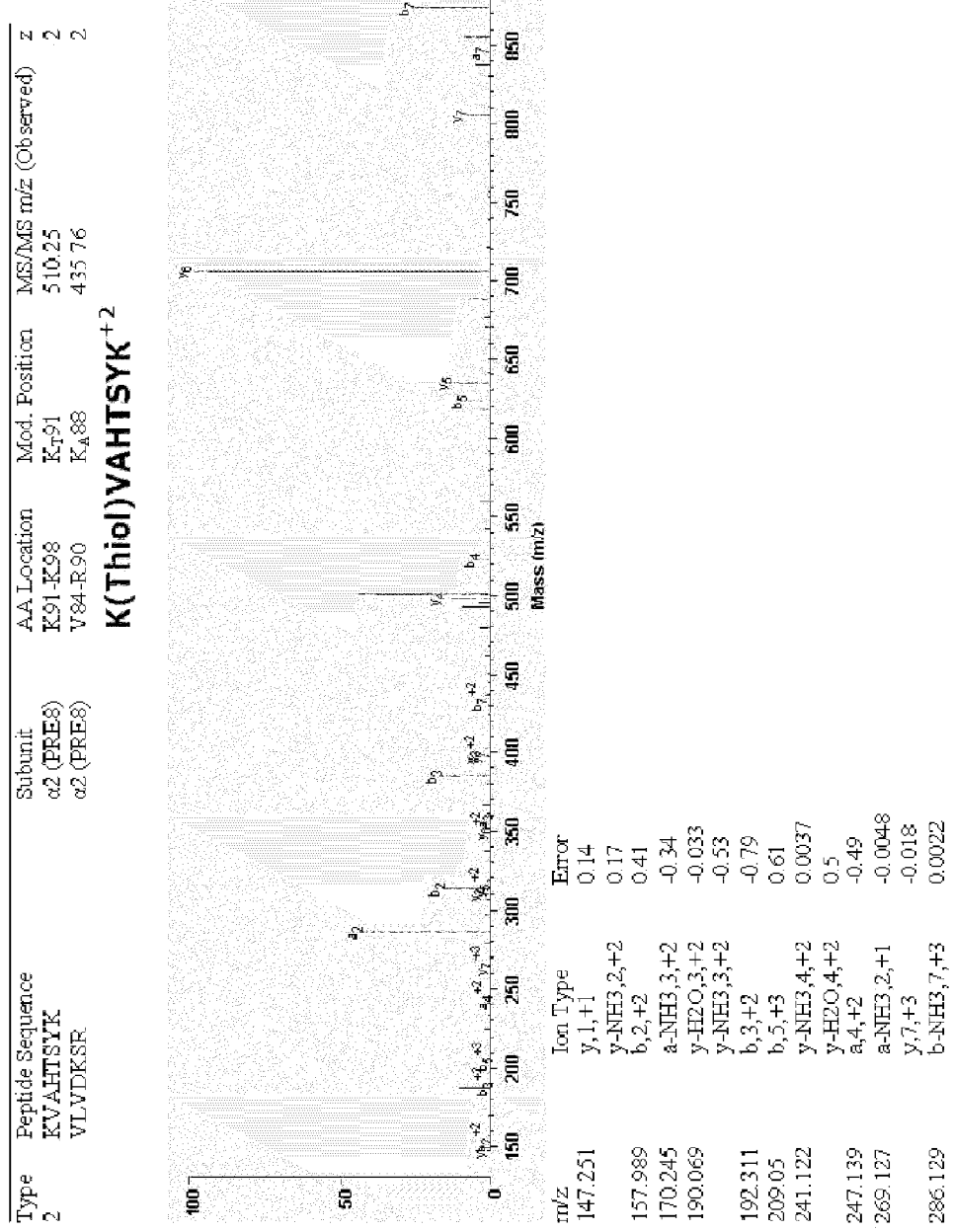
Figure 13:
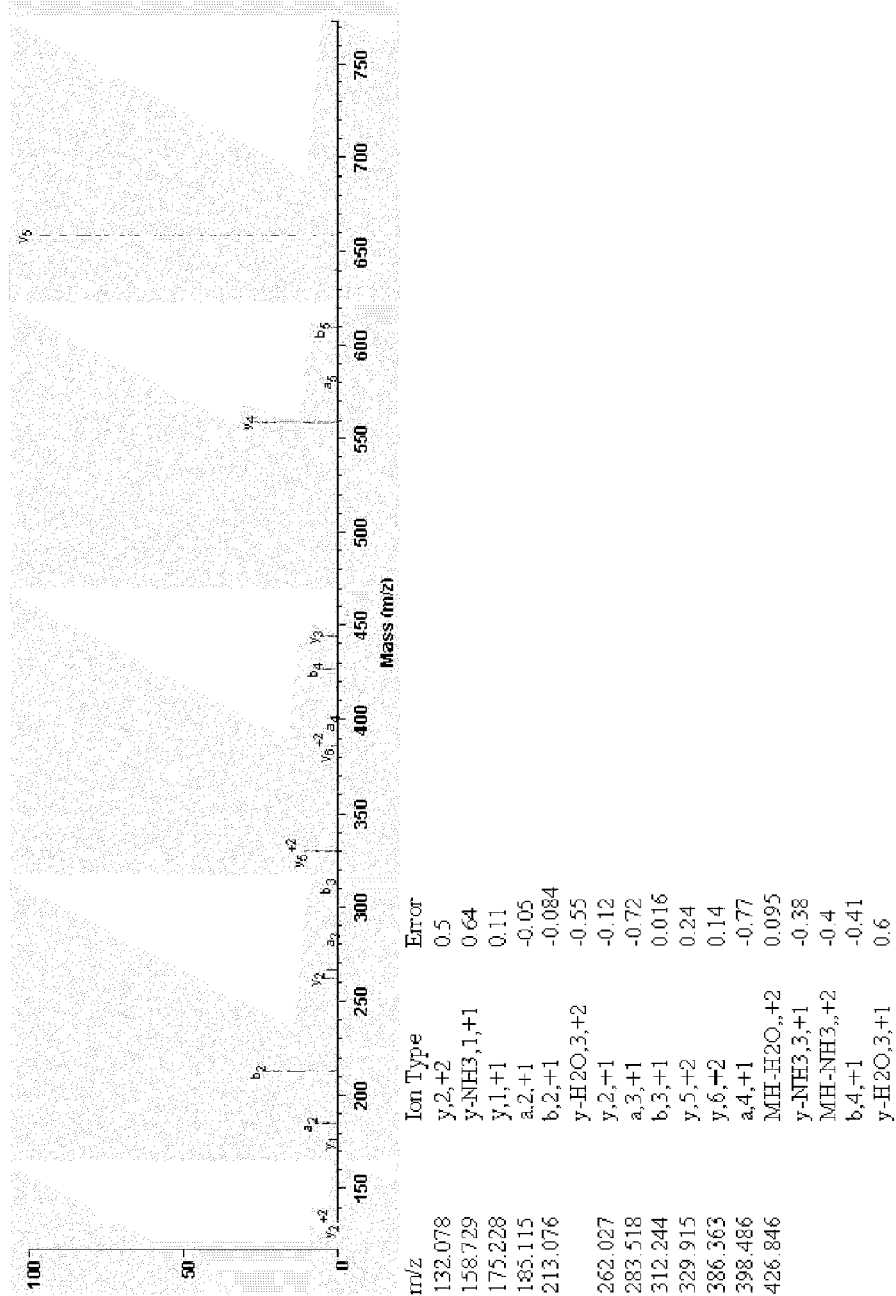
Figure 13:
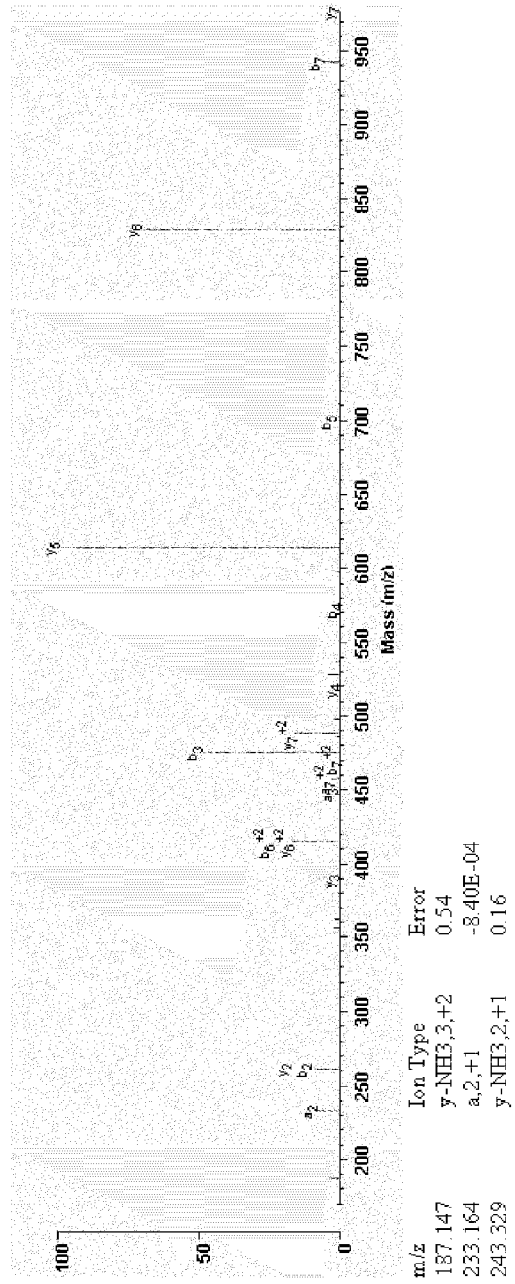
Figure 13:
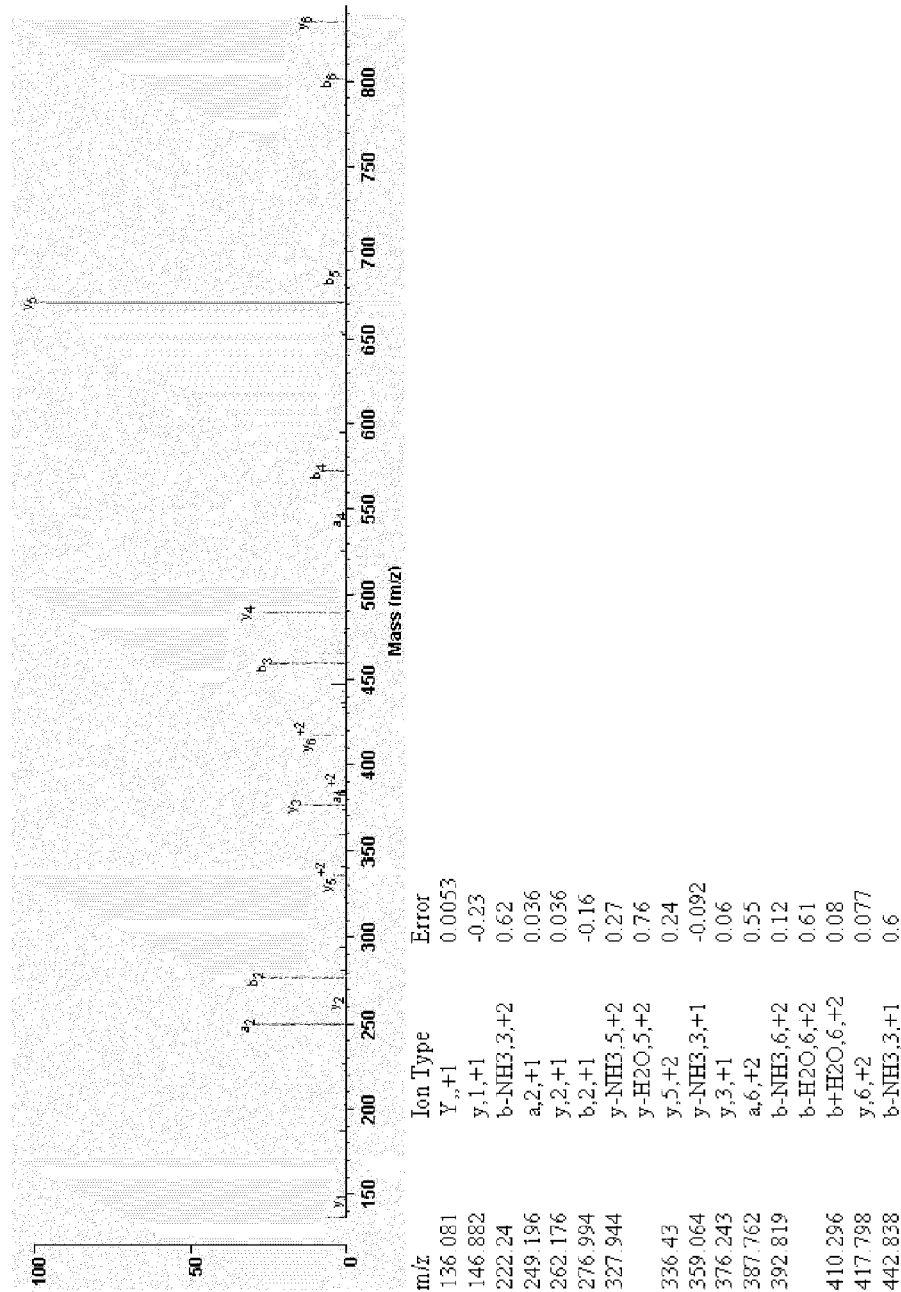
Figure 13:
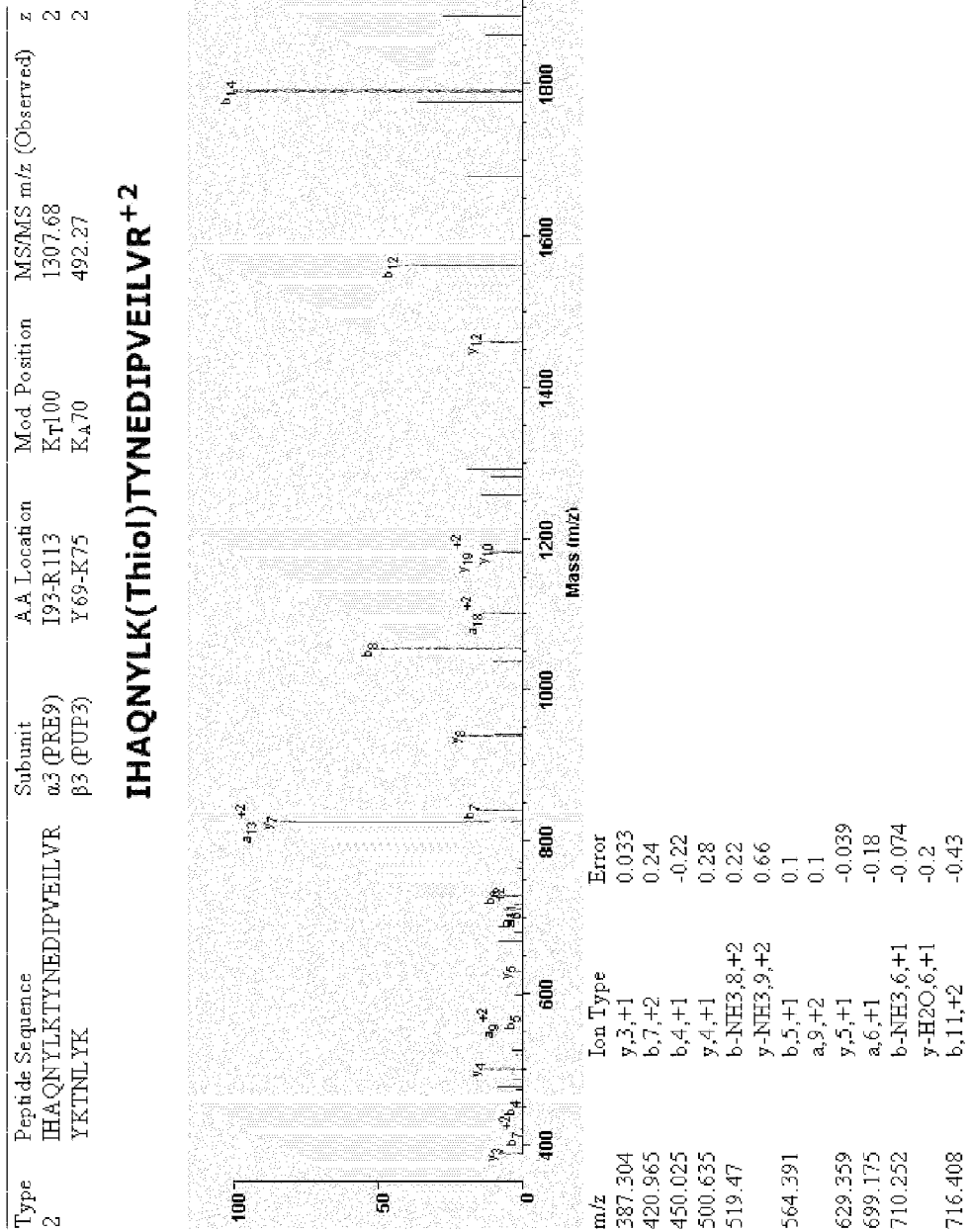
Figure 13:
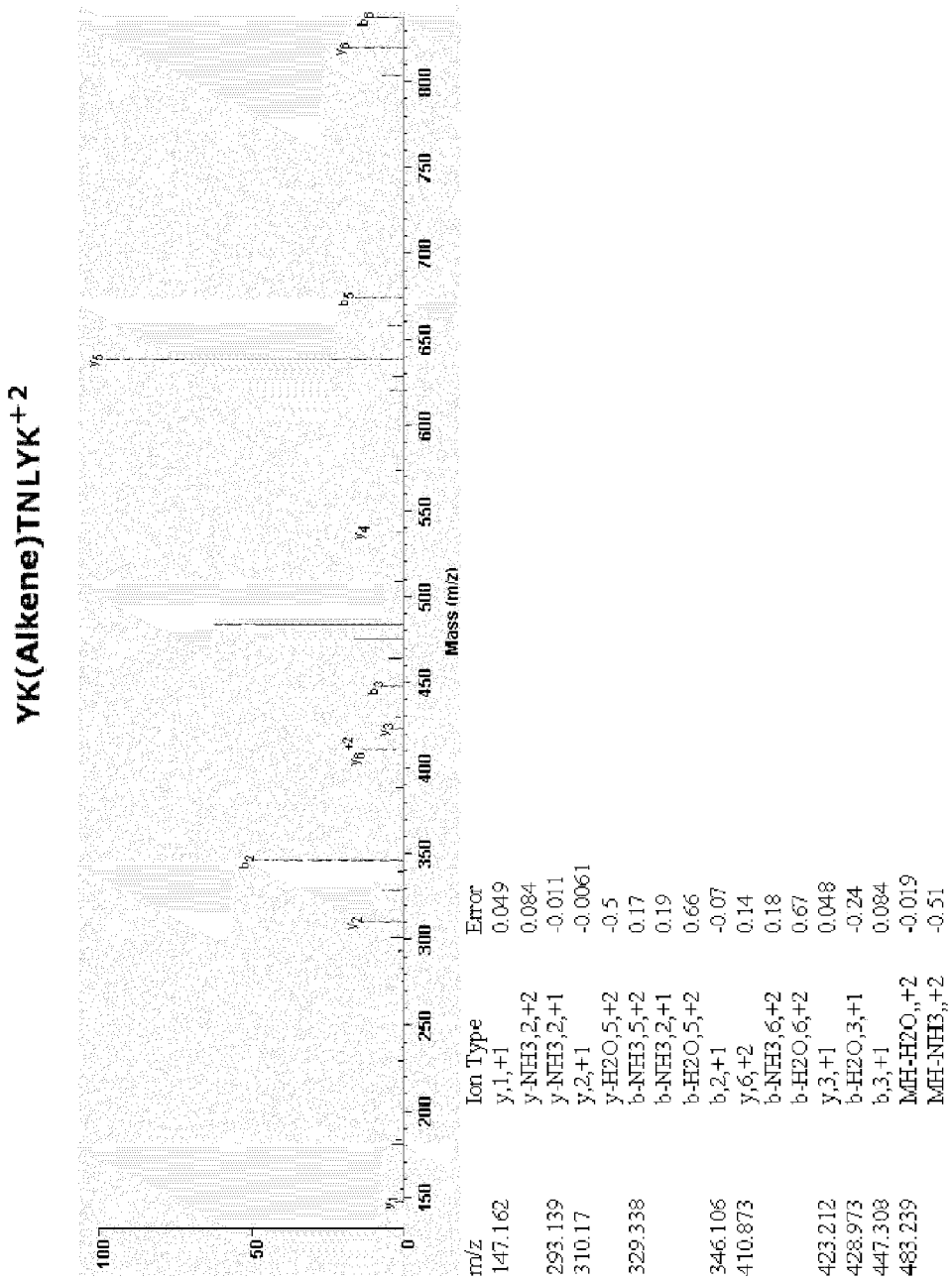
Figure 13:
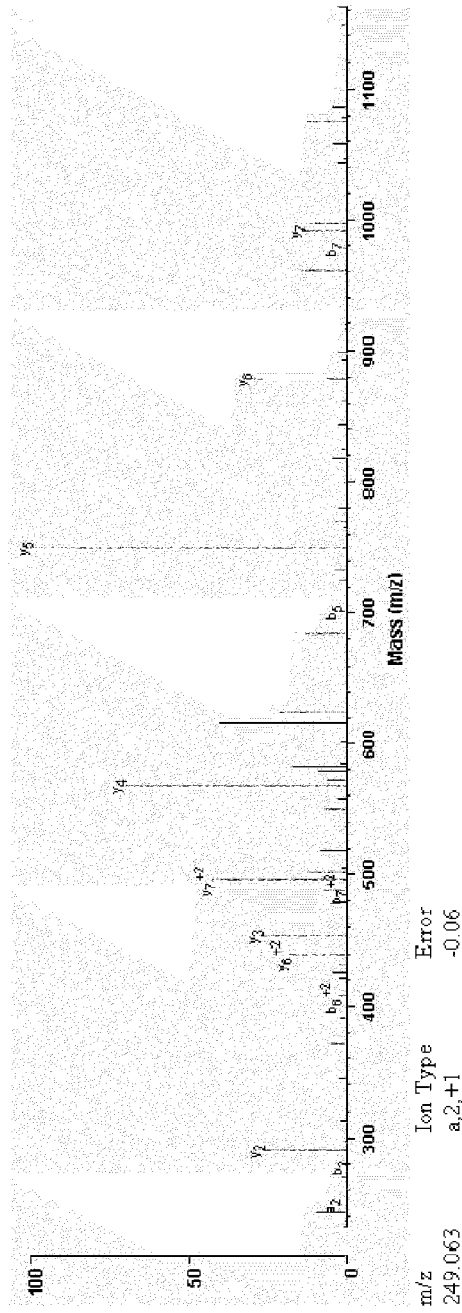
Figure 13:
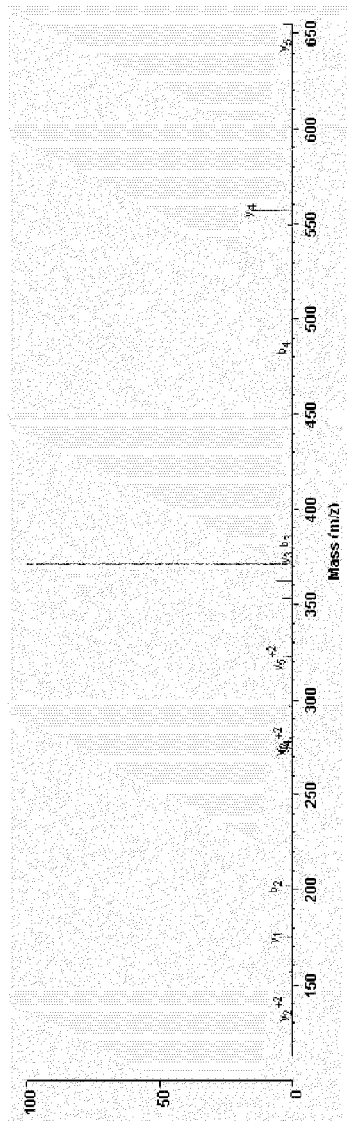
Figure 13:
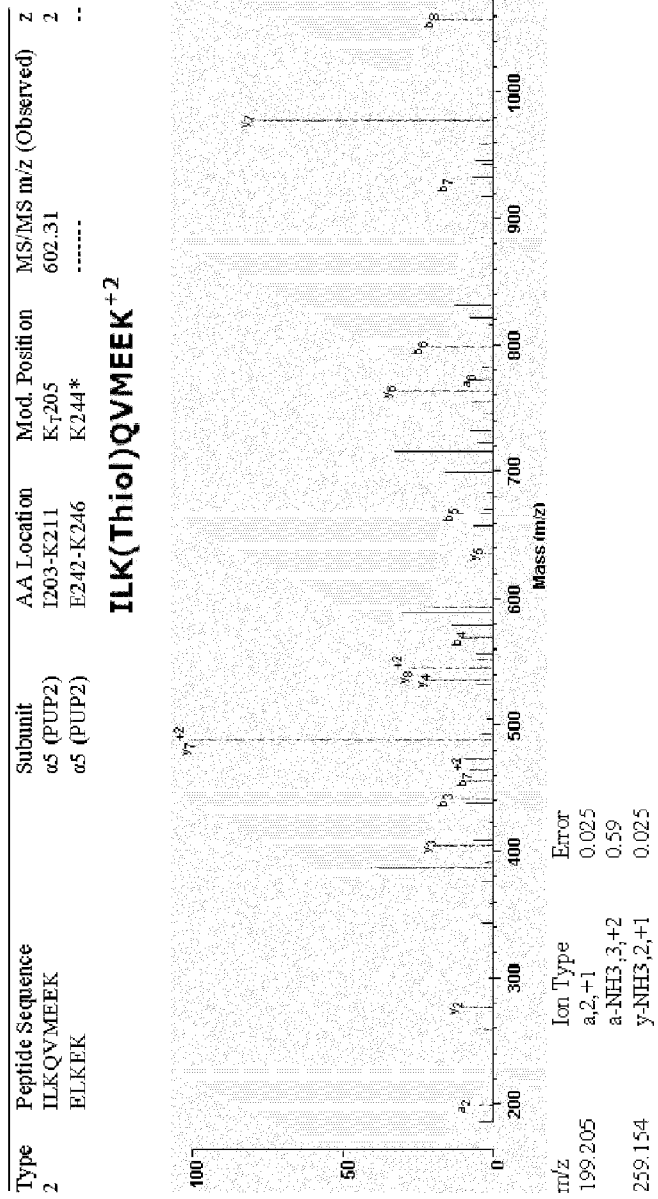
Figure 13:
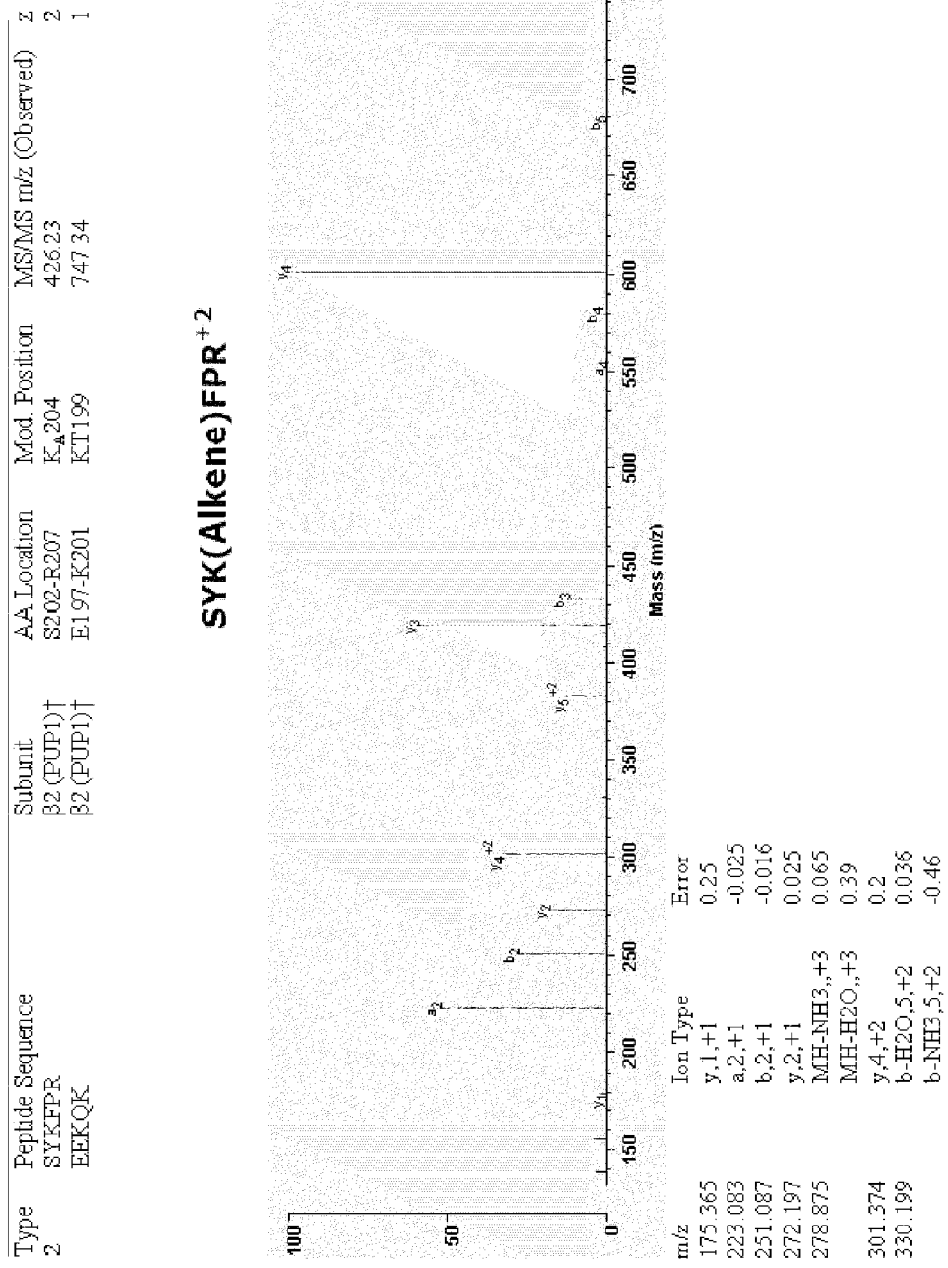
Figure 13:
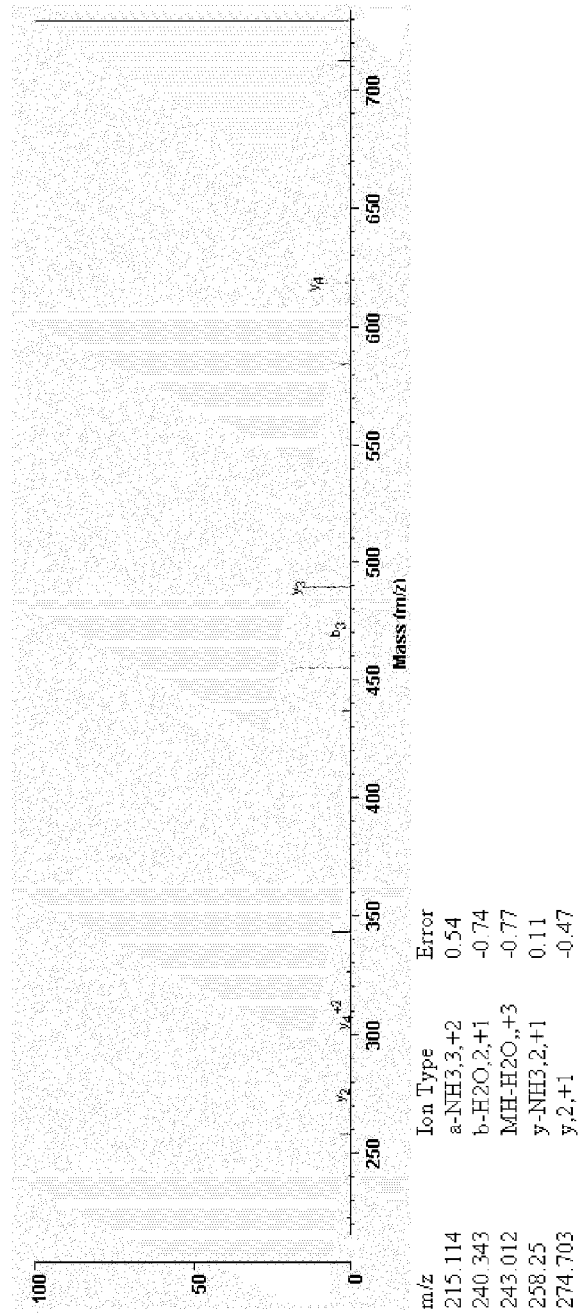
Figure 13:
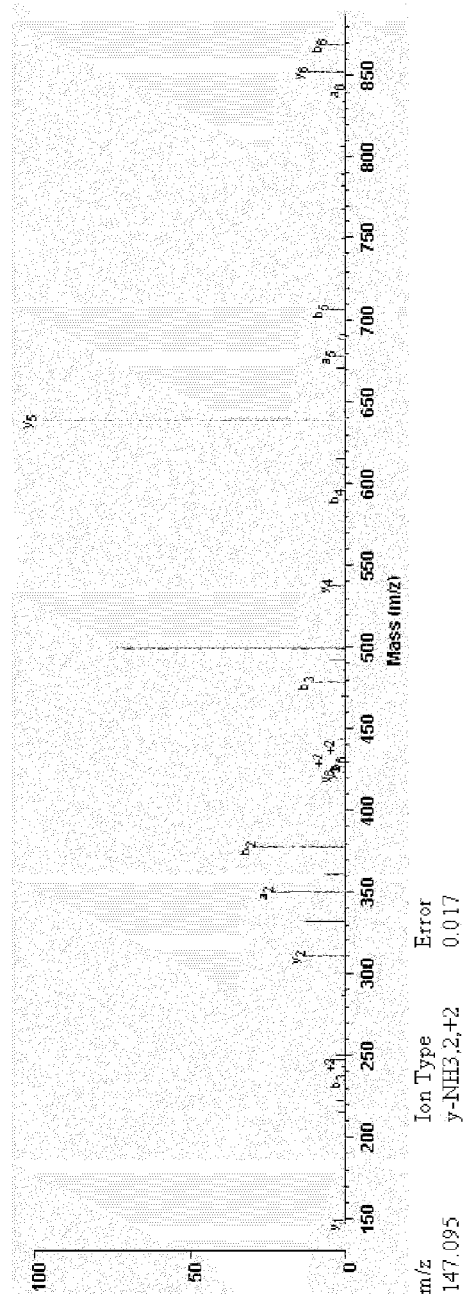
Figure 13:
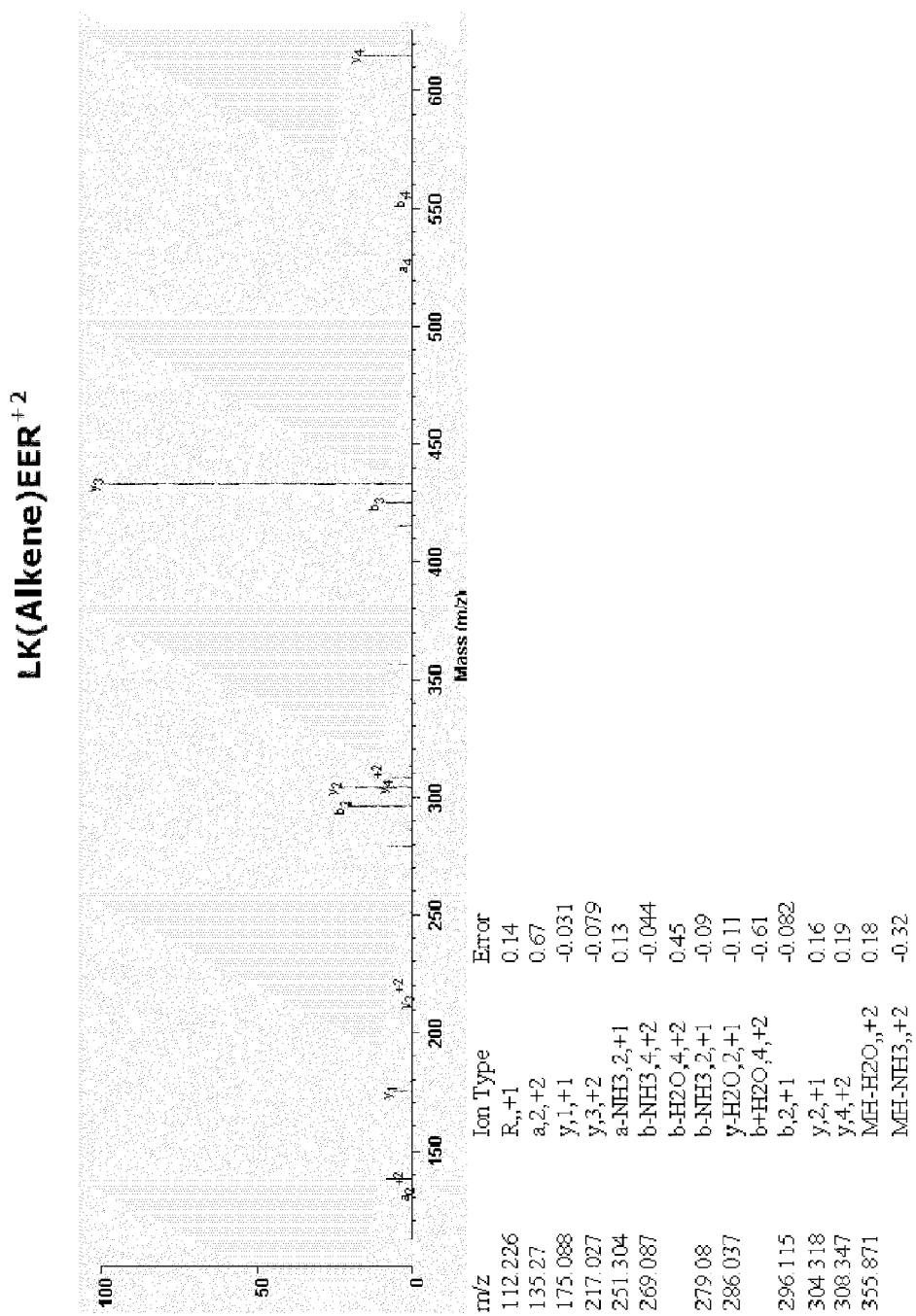
Figure 13:
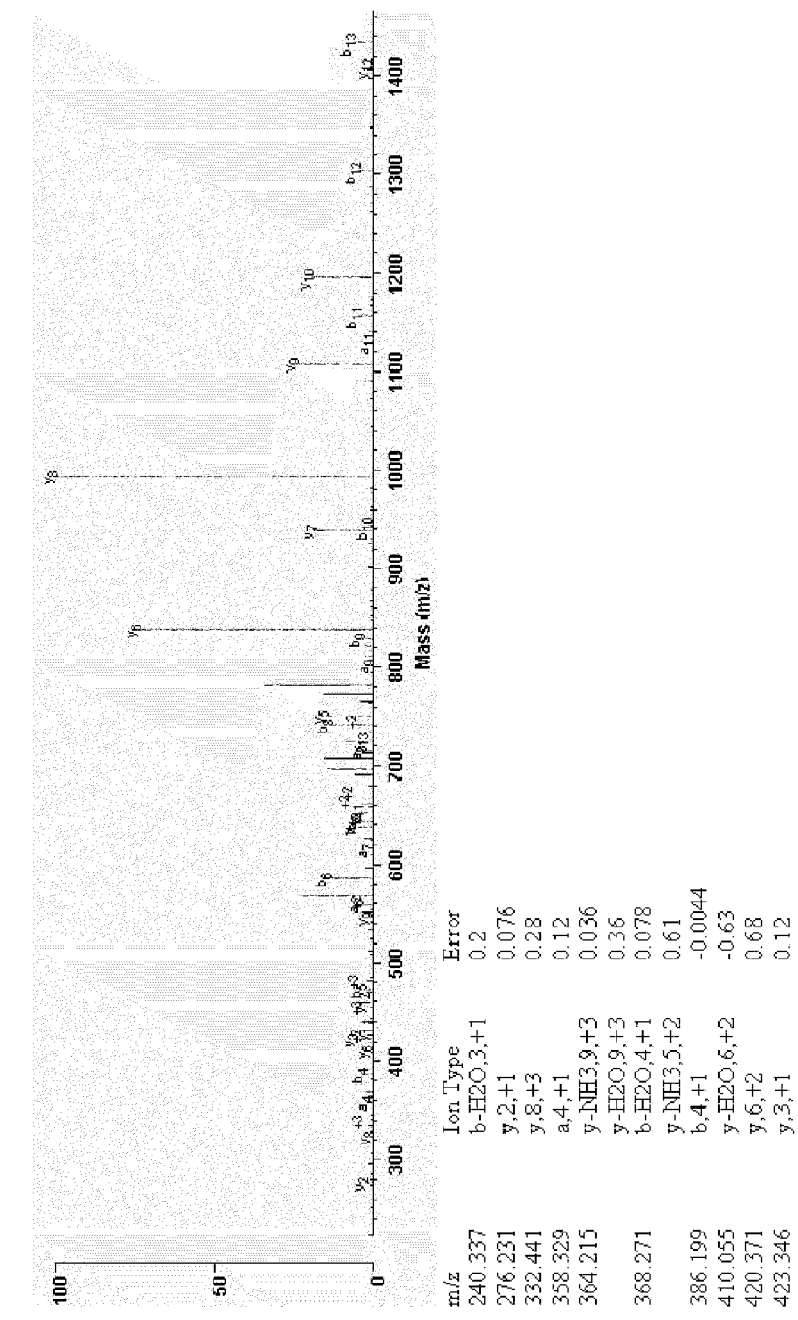
Figure 13:
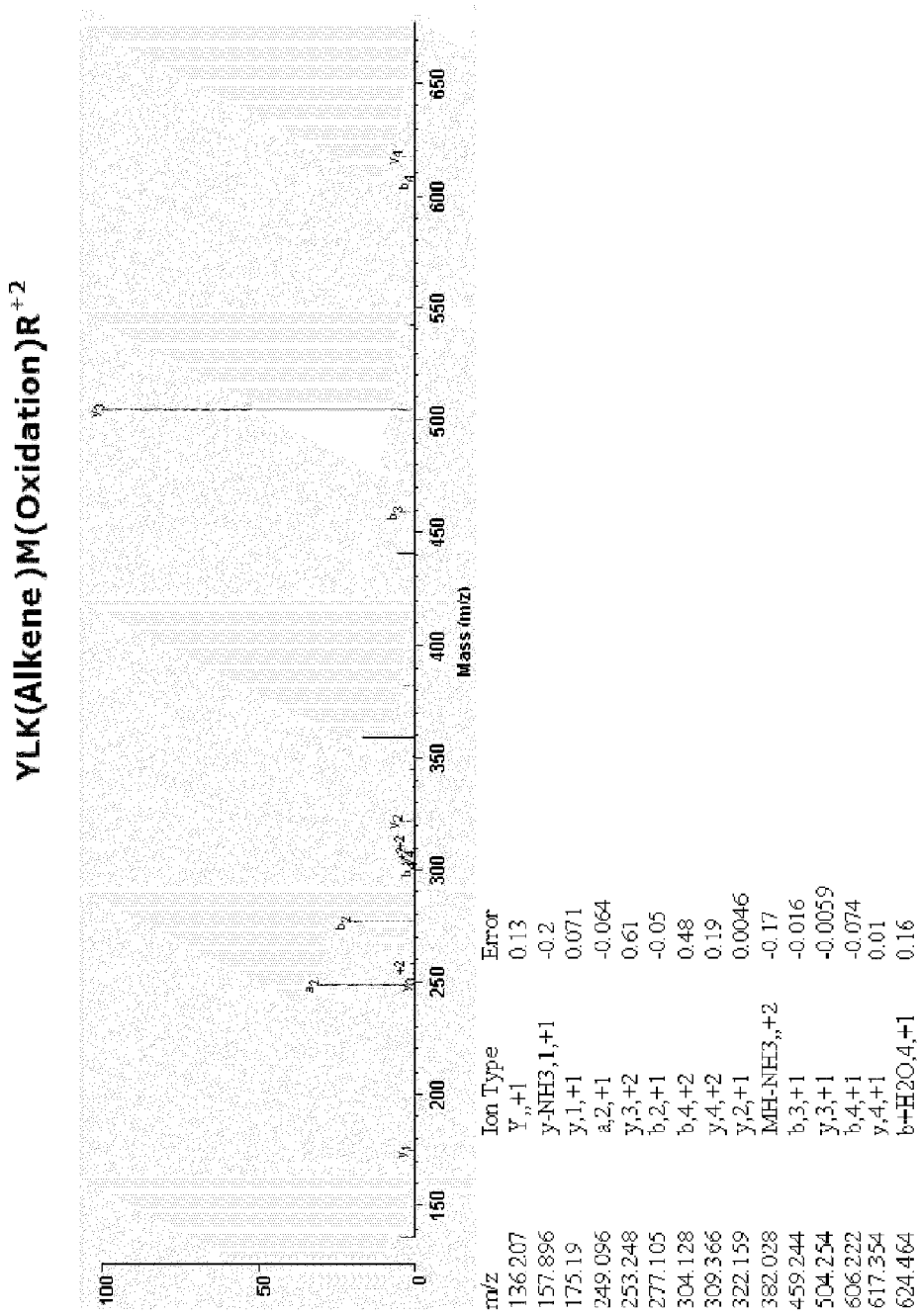
Figure 13:
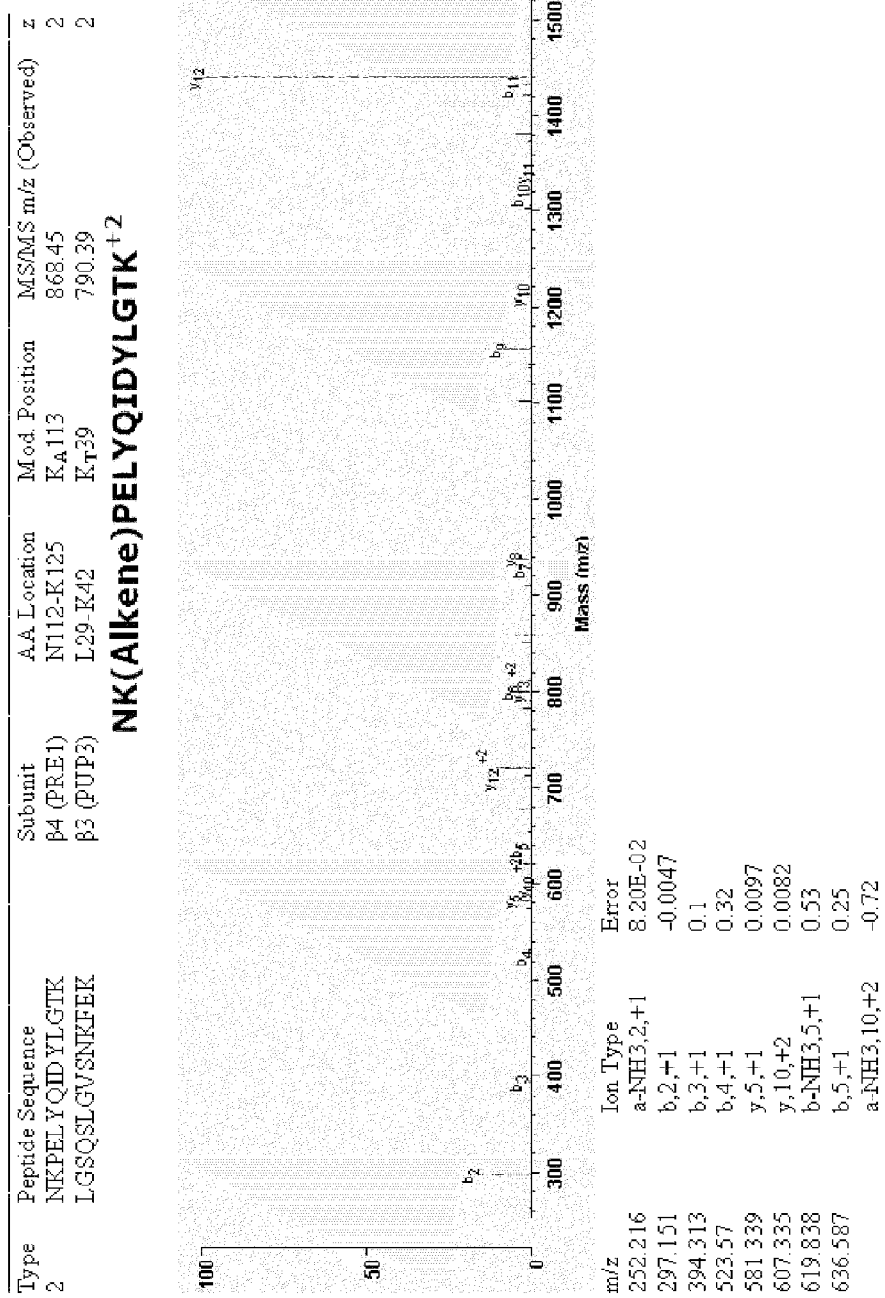
Figure 13:
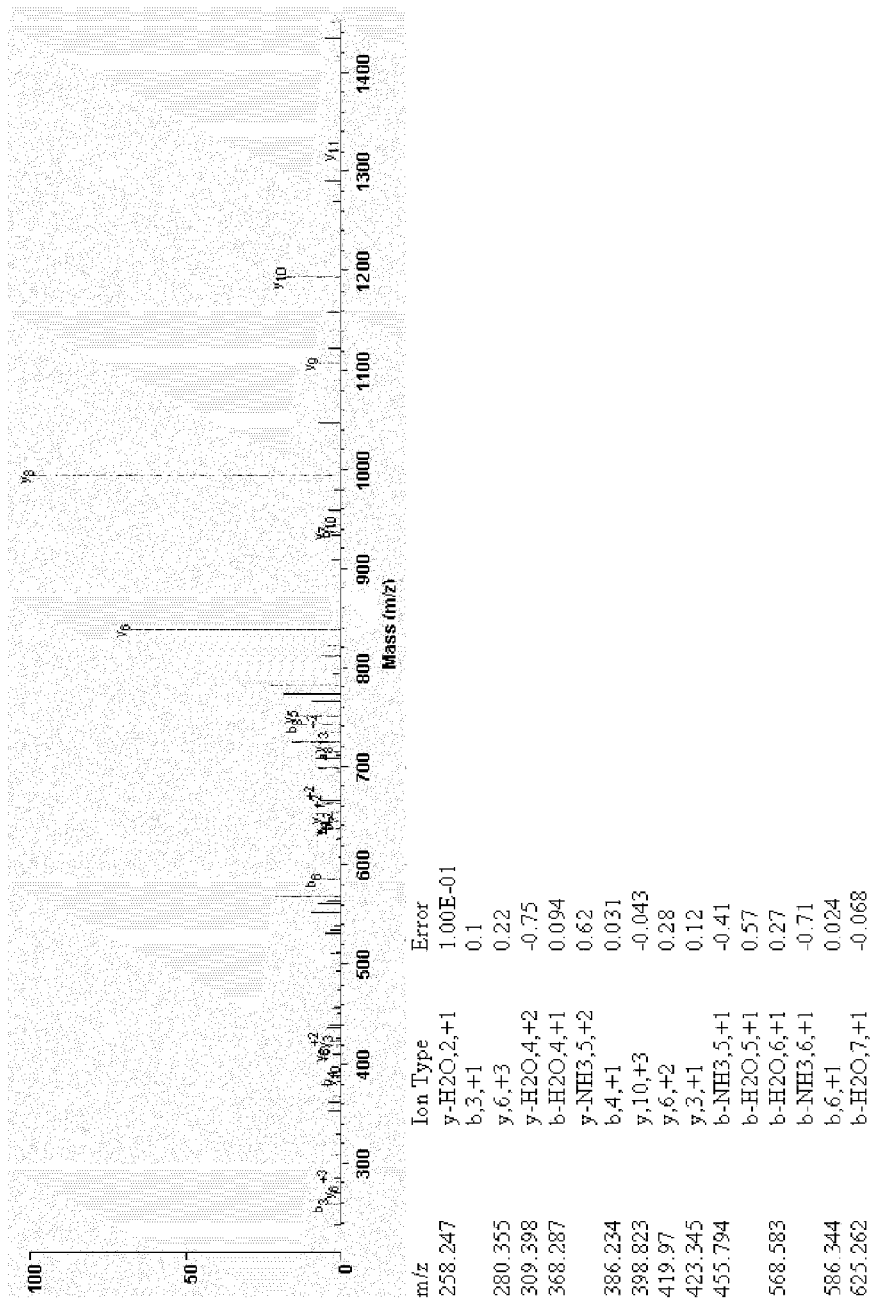
Figure 13:
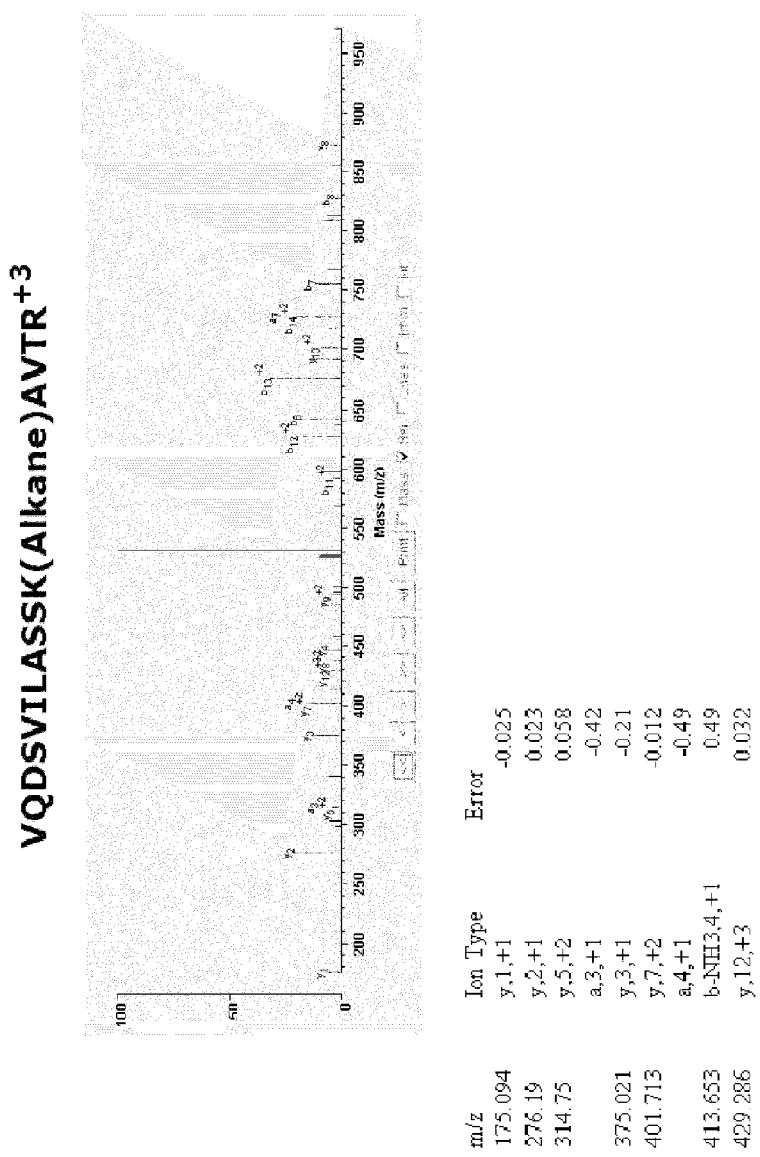
Figure 13:
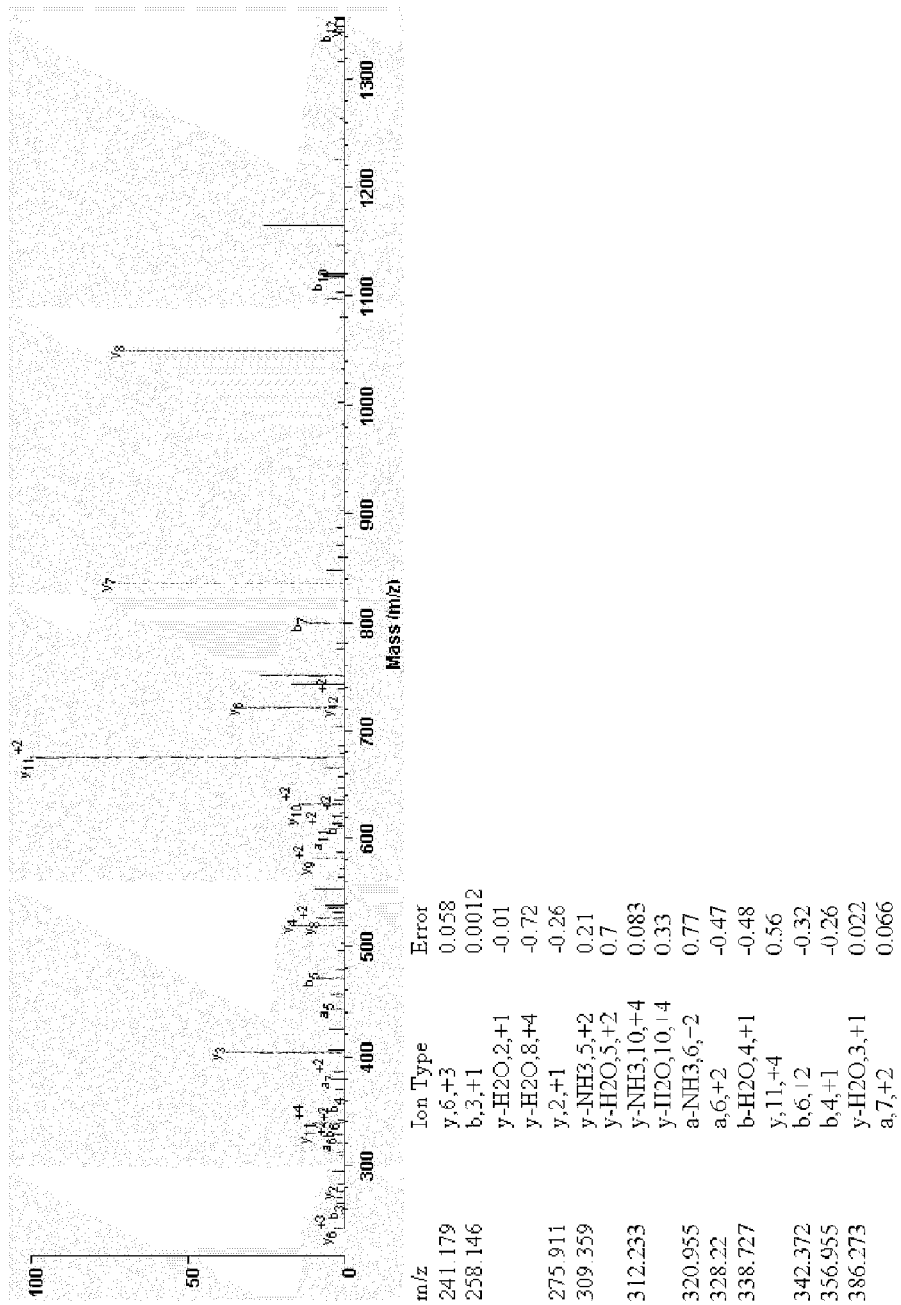
Figure 13:
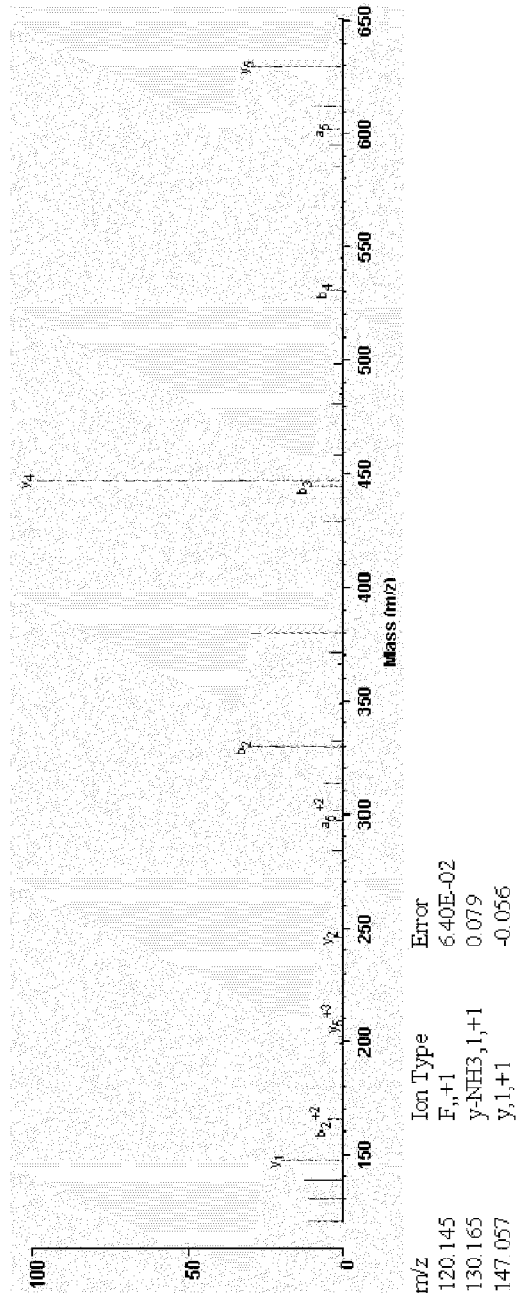
Figure 13:
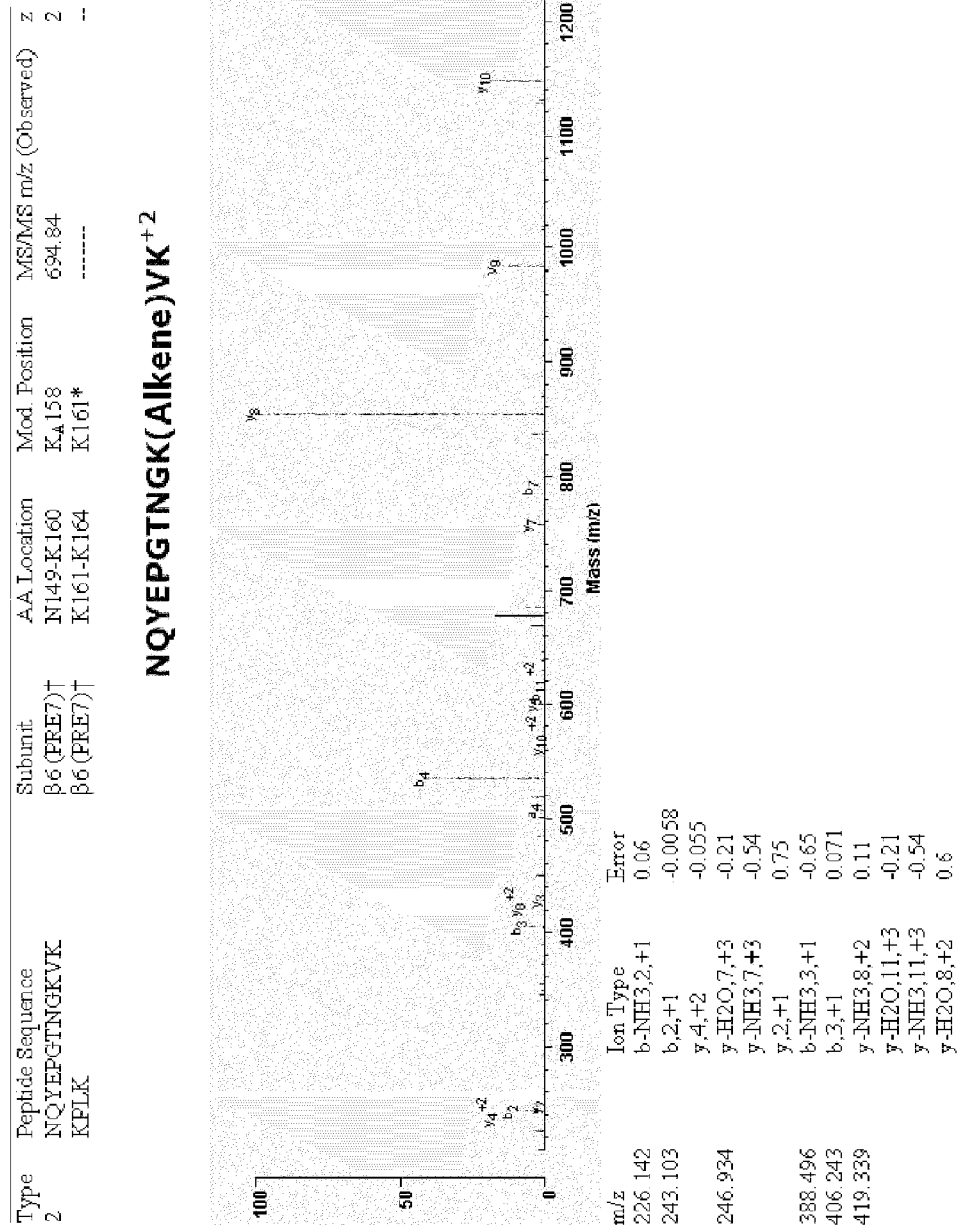

Structural elucidation of the yeast 20 S proteasome complex using DSSO cross-linking—The ubiquitin-proteasome degradation pathway plays an important role in regulating many biological processes (Pickart, C. M., et al.) The 26 S proteasome complex is the macromolecular machine responsible for ubiquitin/ATP dependent protein degradation, and it is composed of two subcomplexes: the 20S core particle and the 19 S regulatory complex. To date, only the crystal structure of the 20 S proteasome complex has been resolved. However, structures of the 19 S and 26 S remain elusive, thus hindering the understanding of the structure and functional relationship of the 26 S proteasome complex. To develop an effective cross-linking strategy to elucidate structures of the 19 S and 26 S proteasome complexes, have therefore investigated the structure of the yeast 20 S proteasome complex using the DSSO cross-linking approach. The cross-linking of the 20 S proteasome complex was carried out in PBS buffer under conditions allowing efficient cross-linking of all subunits as based on 1-D SDS-PAGE (FIG. 12). The tryptic digest of the cross-linked proteasome complex was subjected to LC MS$^n$ analysis and the data were analyzed using the integrated work flow described above (FIG. 7). In total, 13 unique inter-linked peptides were identified including 10 intra-subunit and 3 inter-subunit heterodimeric inter-links as summarized in TABLE 2 (for details see TABLE 5), which were determined unambiguously by integration of Link-Finder, Batch-Tag (MS$^3$ sequencing, see FIG. 13), and MS-Bridge (mass mapping of the cross-linked peptides) results. As an example, FIG. 8A displays the MS/MS spectrum of a DSSO heterodimeric inter-linked peptide α-β (m/z 833.9231$^{4+}$) of the yeast 20 S proteasome complex, in which two fragment pairs were detected and determined as $α_A/β_T$ (868.45$^{2+}$/790.39$^2$) and $α_T/β_T$ (884.44$^{2+}$/774.41$^{2+}$). MS$^3$ analysis of the $α_A$ fragment (m/z 868.45$^{2+}$) identified the α chain unambiguously as NK$_A$PELYQIDYLGTK, which matched to 20 S subunit β4. In this sequence, K$_A$ is modified with the alkene moiety. In addition, MS$^3$ analysis of the $β_T$ fragment (m/z 790.39$^{2+}$) identified the β chain unambiguously as LGSQSLGVSNK$_T$FEK, which matched to 20 S subunit β3. Here, K$_T$ is modified with an unsaturated thiol moiety. Mass mapping by MS-Bridge further confirmed this inter-subunit (β4-β3) inter-linked peptide as [NKPELYQIDYLGTK inter-linked to LGSQSLGVSNKFEK].

Figure 14:
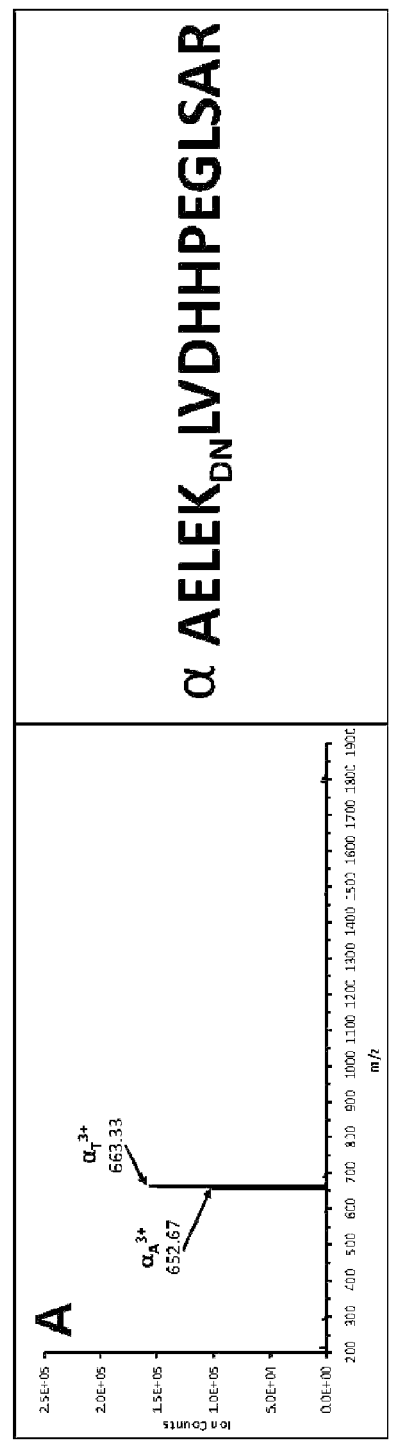
FIG. 14 is an exemplary $MS^n$ analysis of a DSSO dead-end peptide of the yeast 20S proteasome complex. A) MS/MS spectrum of a dead-end (DN) peptide ($α_{DN}$, m/z $693.0078^{3+}$, AELEK$_{DN}$LVDHHPEGLSAR), in which two fragment ions were determined as αA (m/z $652.67^{3+}$) and $α_T$ (m/z $663.33^{3+}$); B) $MS^3$ spectrum of $α_A$ (m/z $652.67^{3+}$), detection of a series of y and b ions determined its sequence unambiguously as AELEK$_A$LVDHHPEGLSAR, in which K$_A$ is modified with the alkene moiety. The sequence matched to subunit α7; C) MS3 spectrum of αT (m/z 663.33³), detection of a series of y and b ions determined its sequence unambiguously as AELEK$_T$LVDHHPEGLSAR, in which K$_T$ is modified with the unsaturated thiol moiety.
Figure 14:
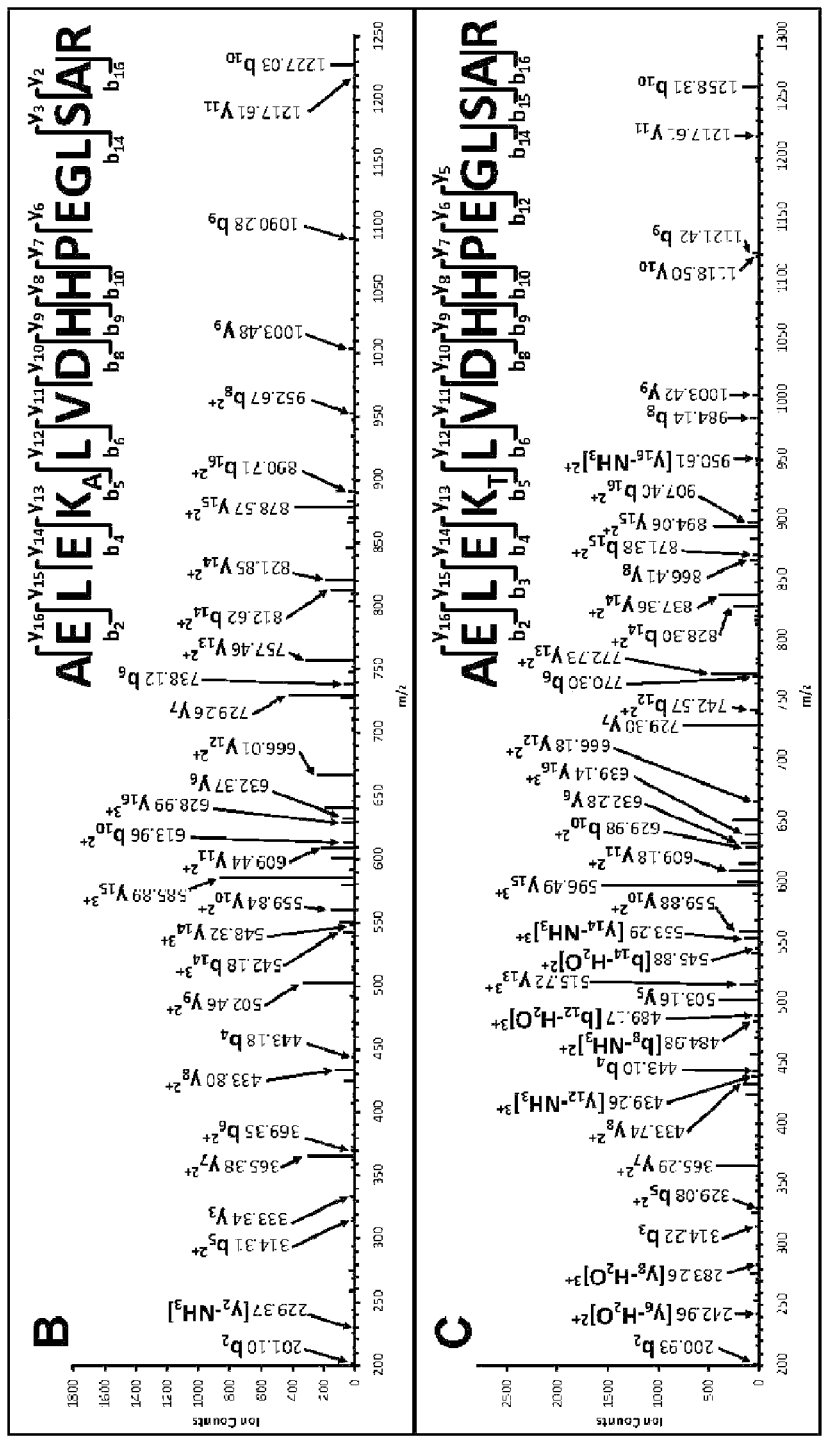

In addition, 21 dead-end modified peptides were identified by multiple lines of evidence as illustrated in TABLE 5. The fragmentation behavior for the dead-end modified peptides of the 20 S subunits is the same as that of cytochrome c showing two distinct dead-end pairs in MS/MS spectra. This is illustrated with an example shown in FIG. 14.

Figure 9:
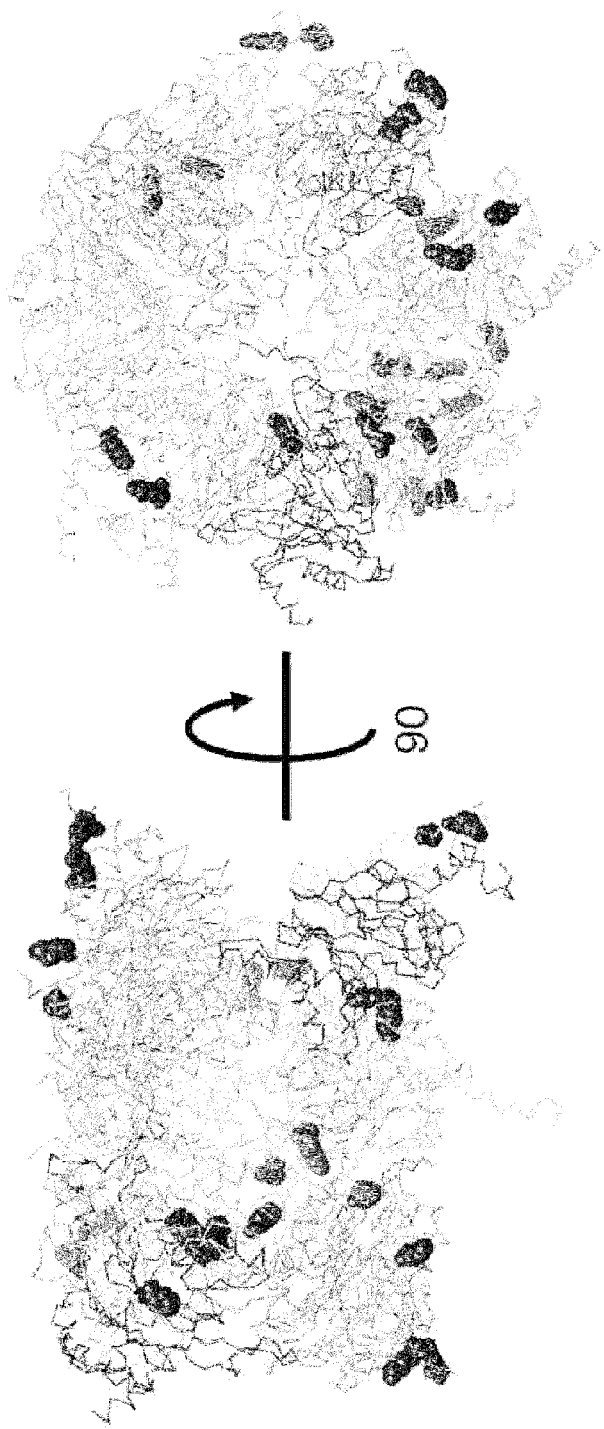
FIG. 9 shows a mapping identified DSSO-interlinked lysines onto crystal structure of yeast 20 S proteasome. The lysines forming intrasubunit cross-links appear space-filled in blue, and those forming intersubunit cross-links appear space-filled in red.
Figure 10:
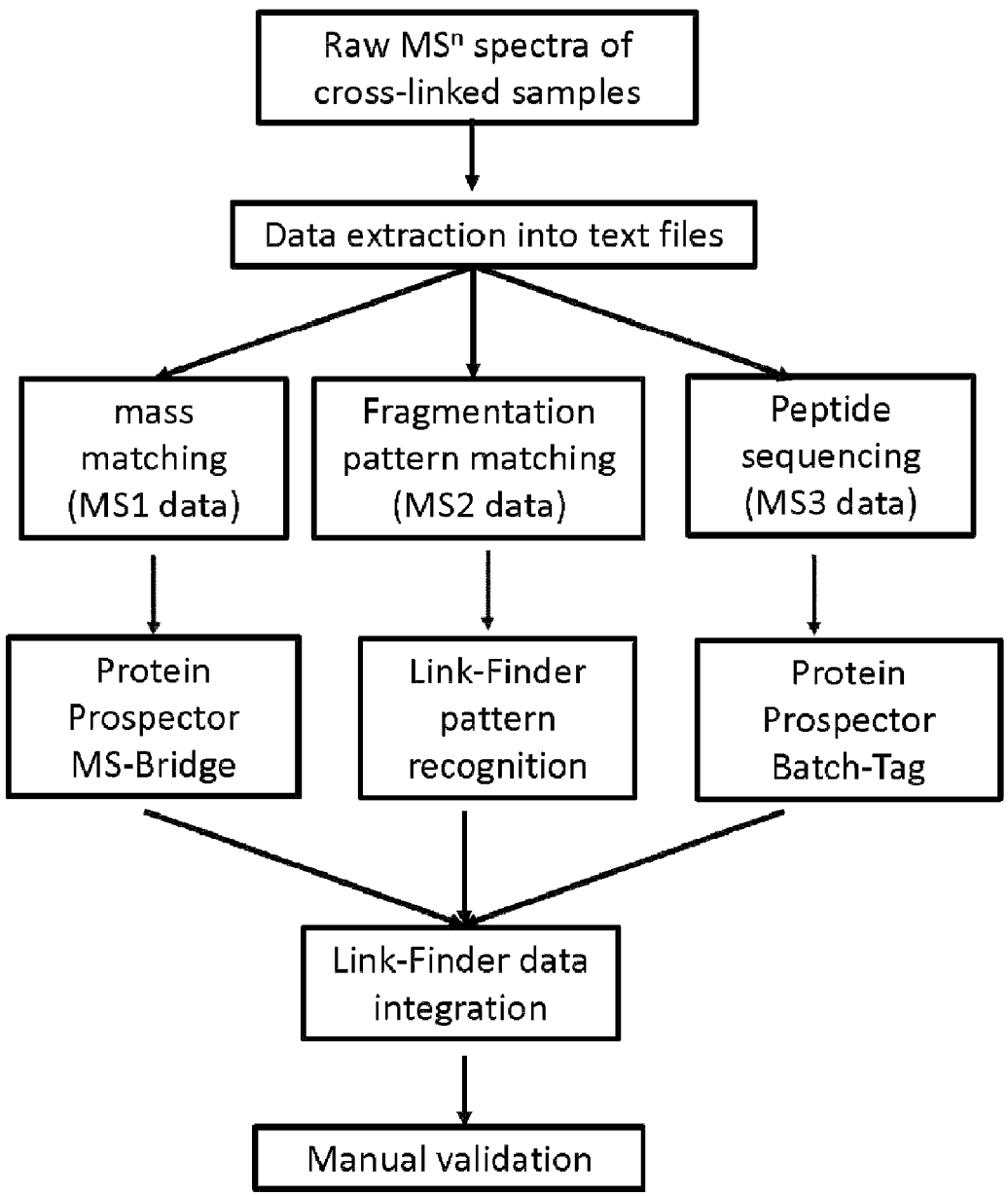
FIG. 10 is a flowchart showing a general technique for identifying crosslinked peptides according to one embodiment of the invention.
Figure 11A:
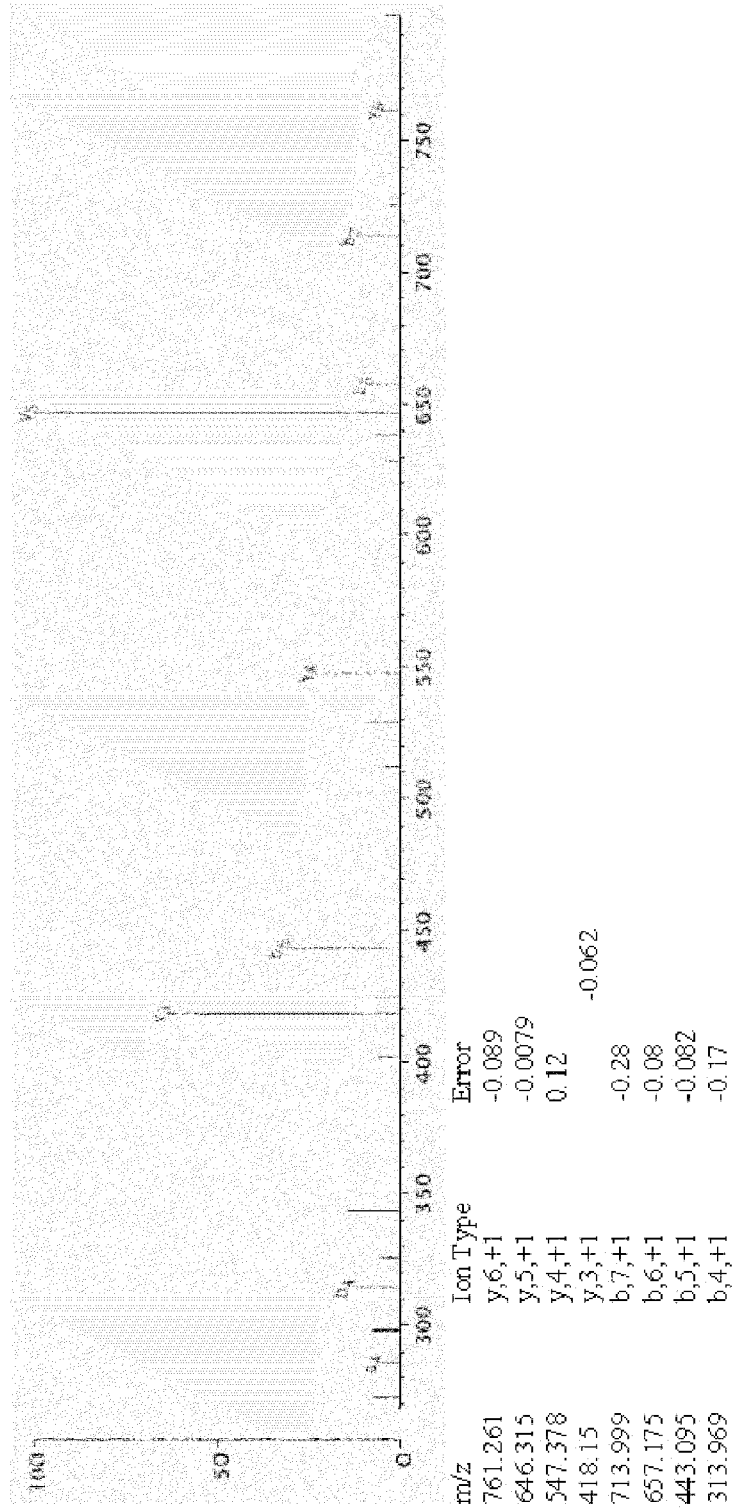
FIG. 11A is an exemplary $MS^3$ analysis of DSSO interlinked peptides of cytochrome c.
Figure 11A:
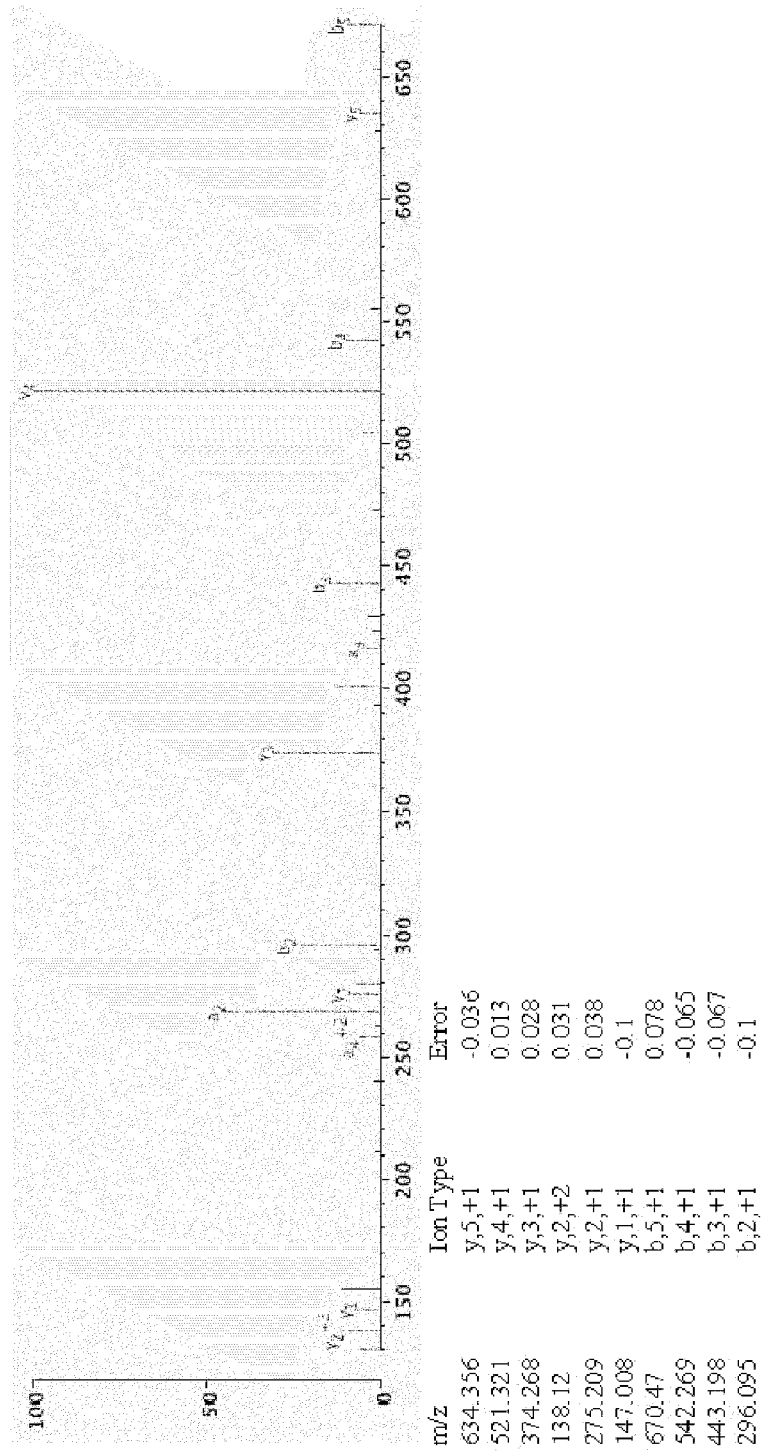
Figure 11A:
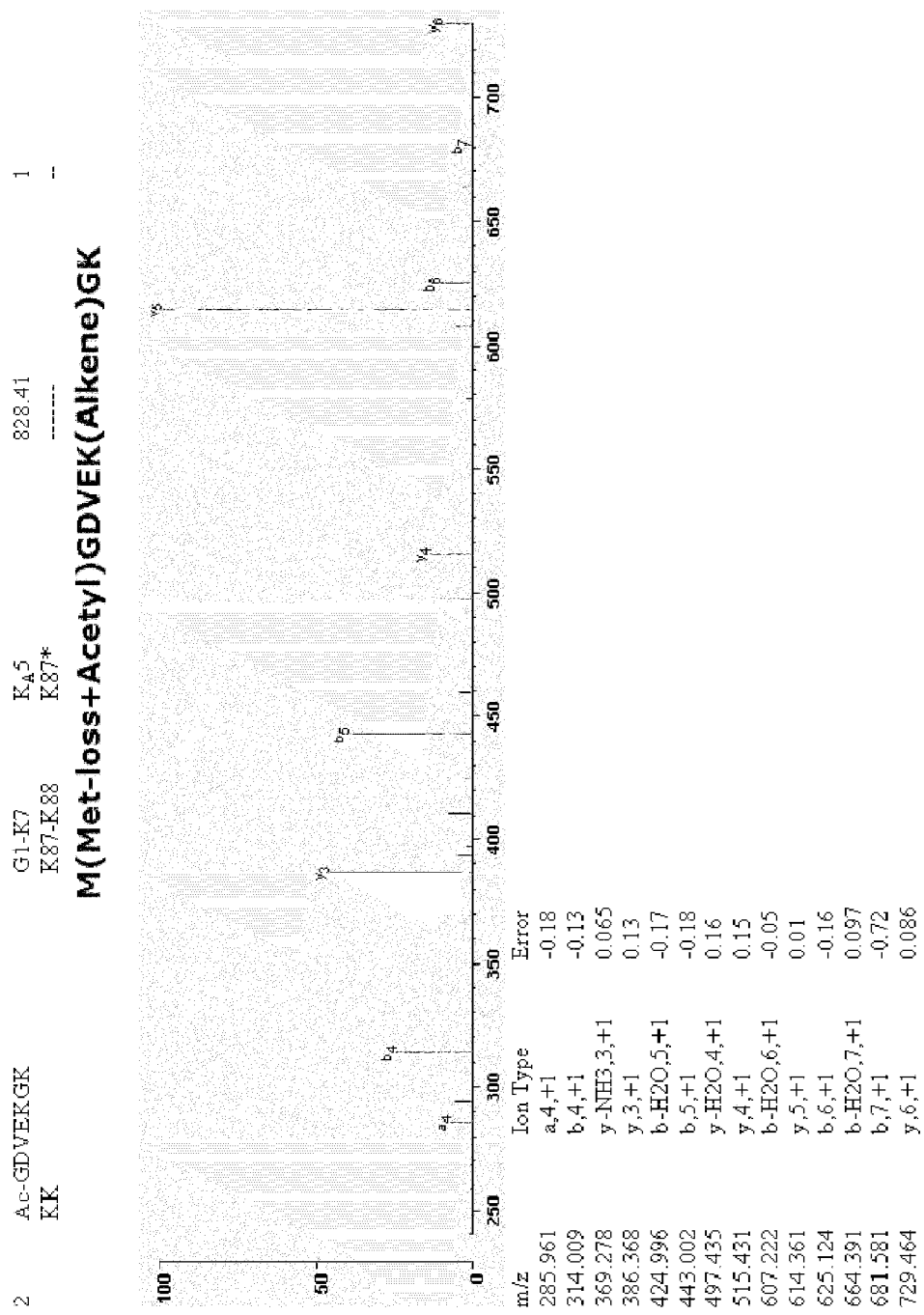
Figure 11A:
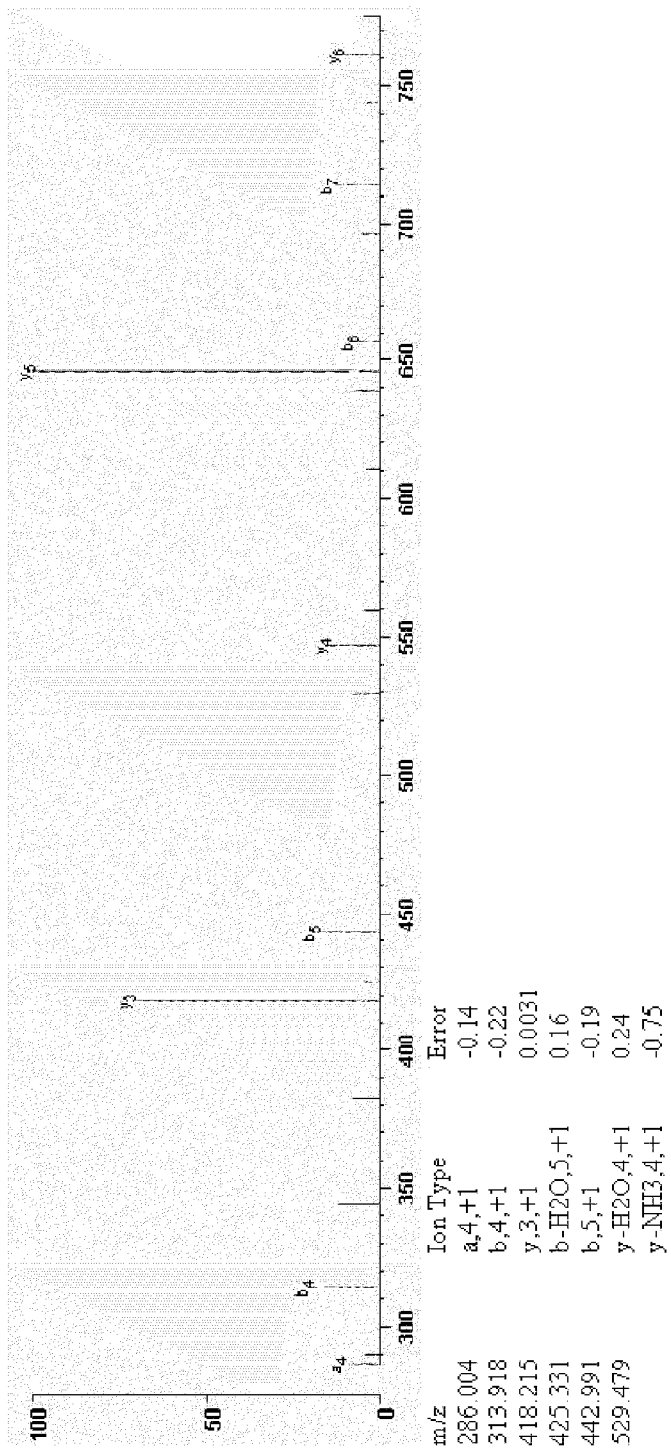
Figure 11A:
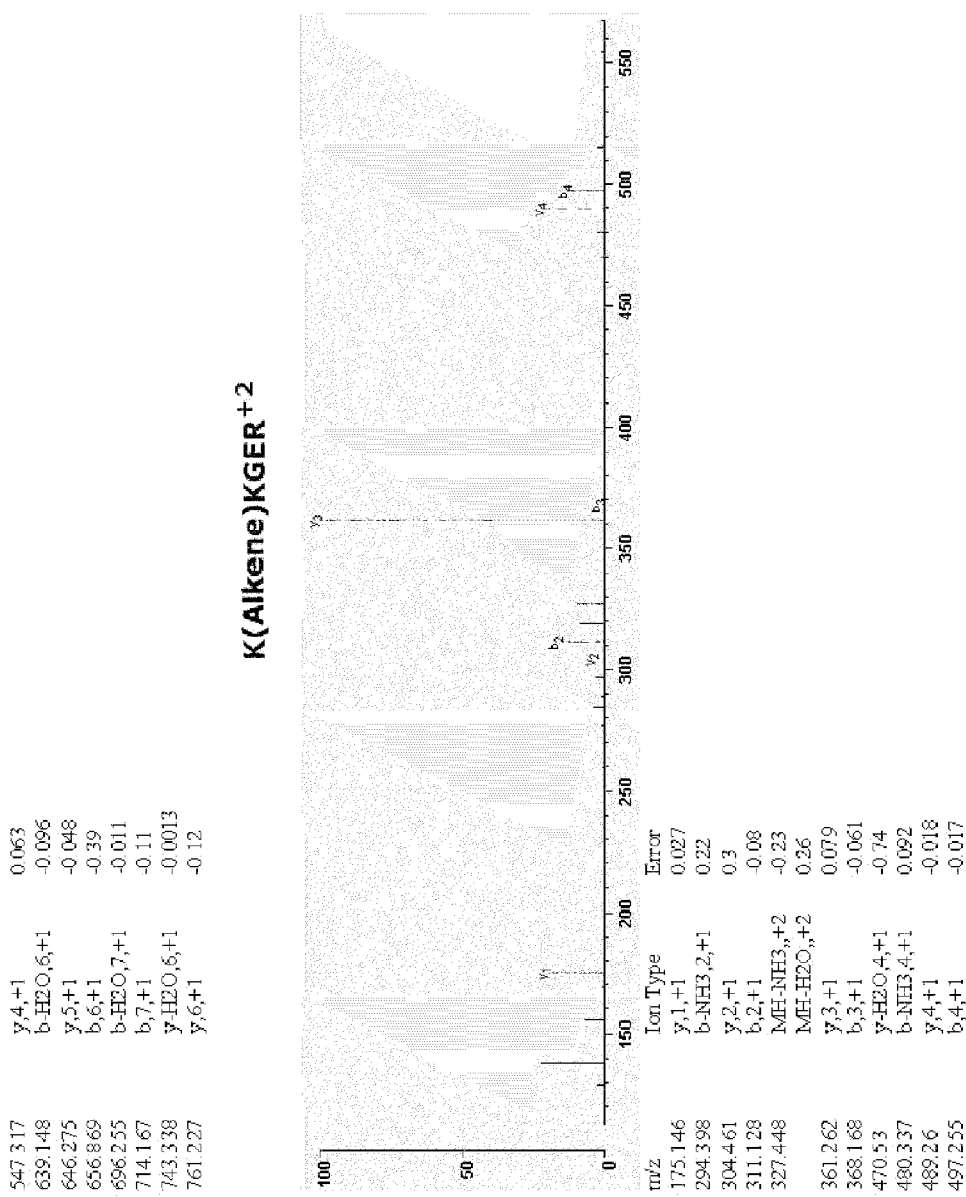
Figure 11A:
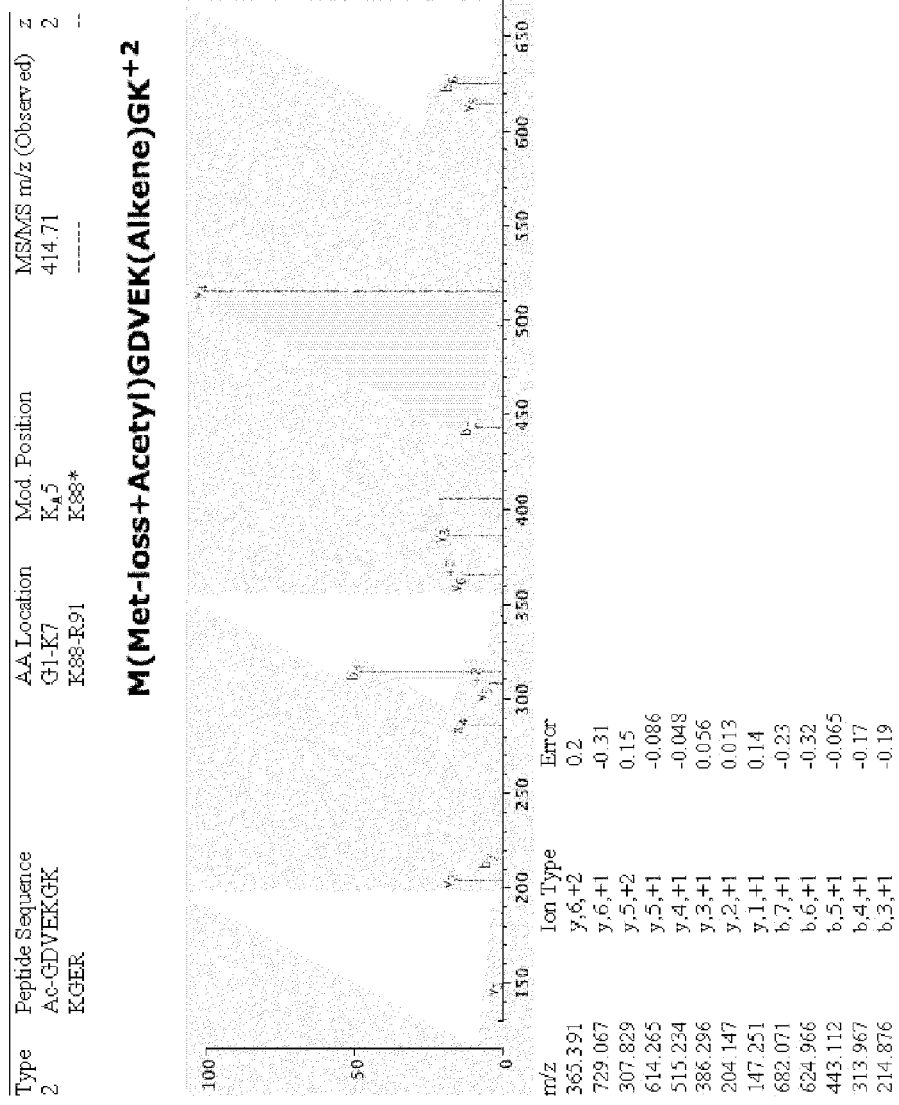
Figure 11A:
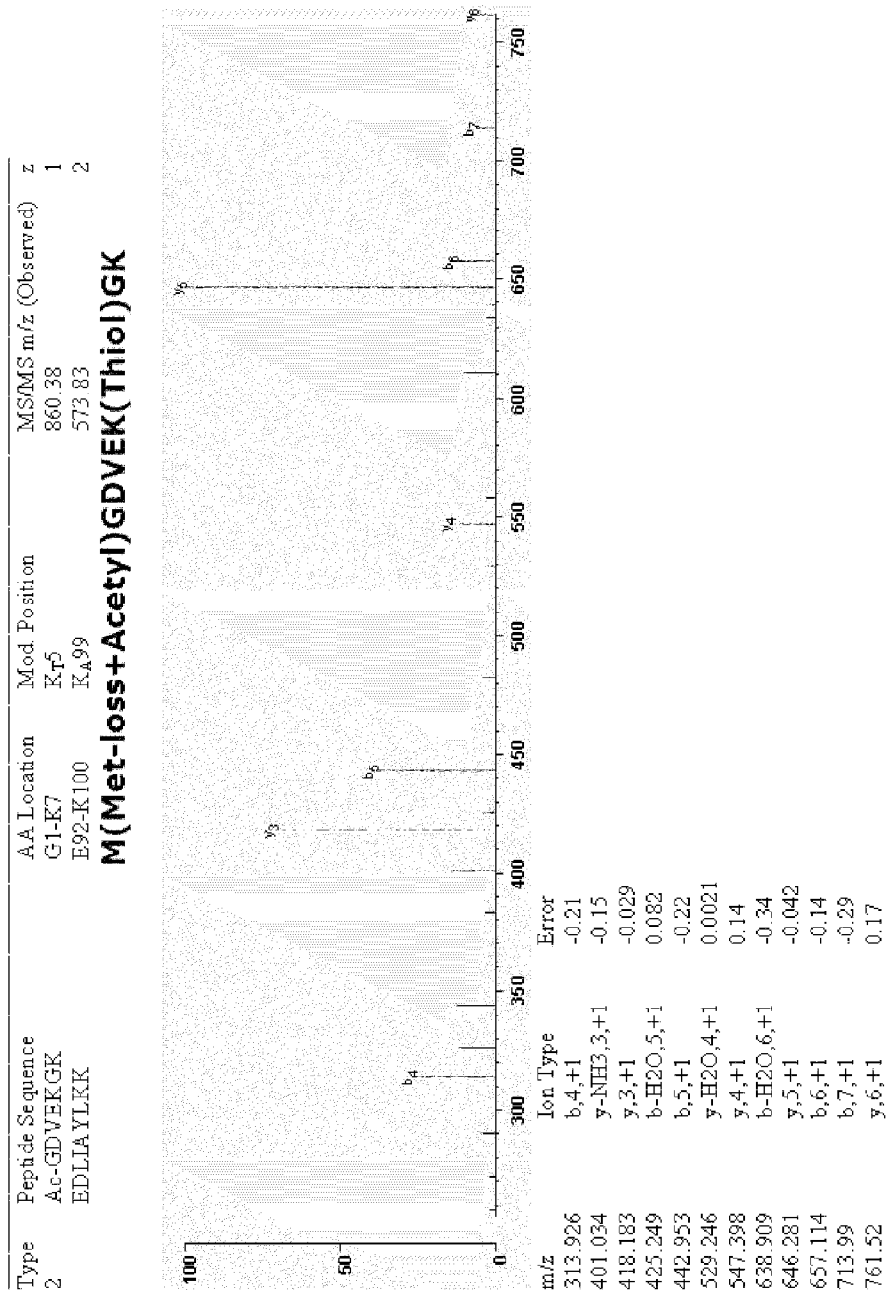
Figure 11A:
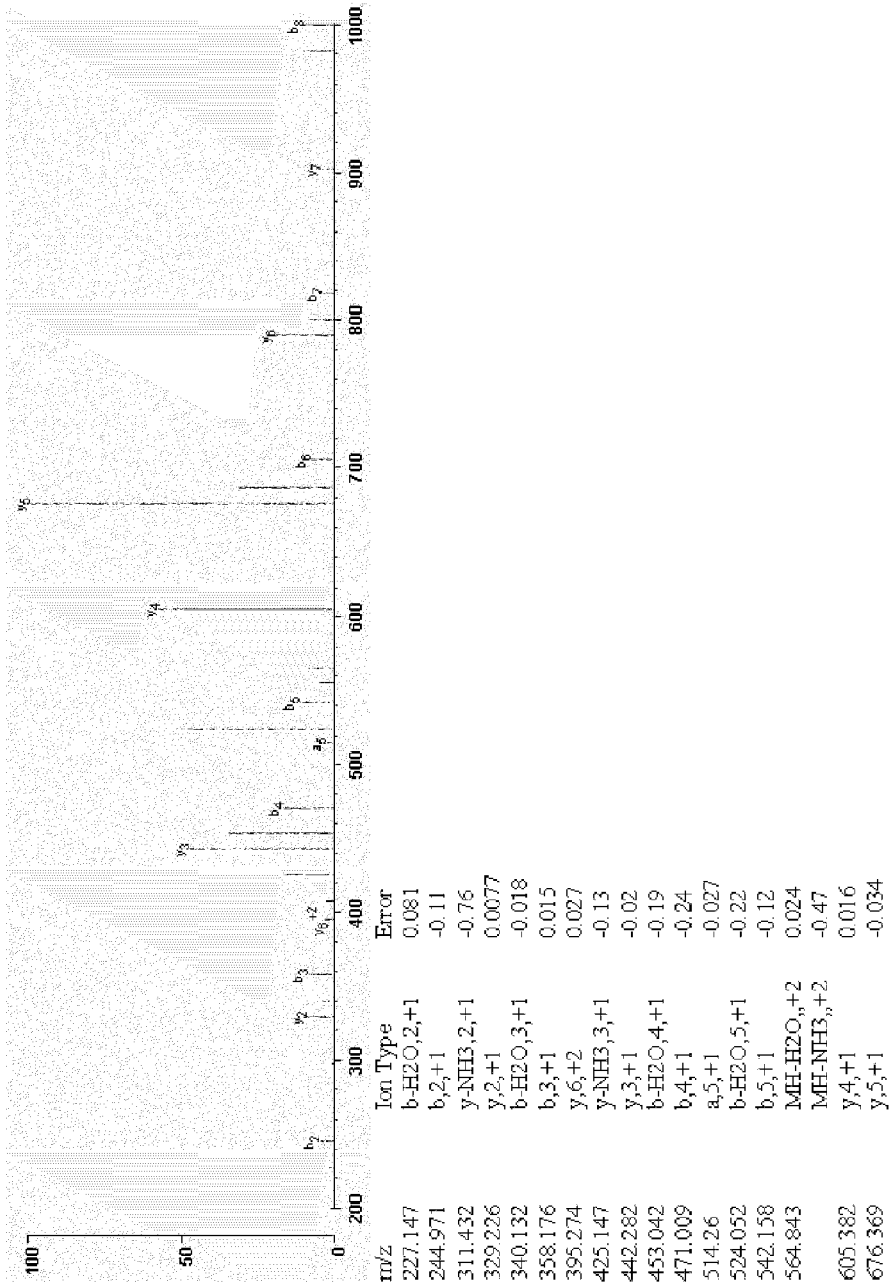
Figure 11A:
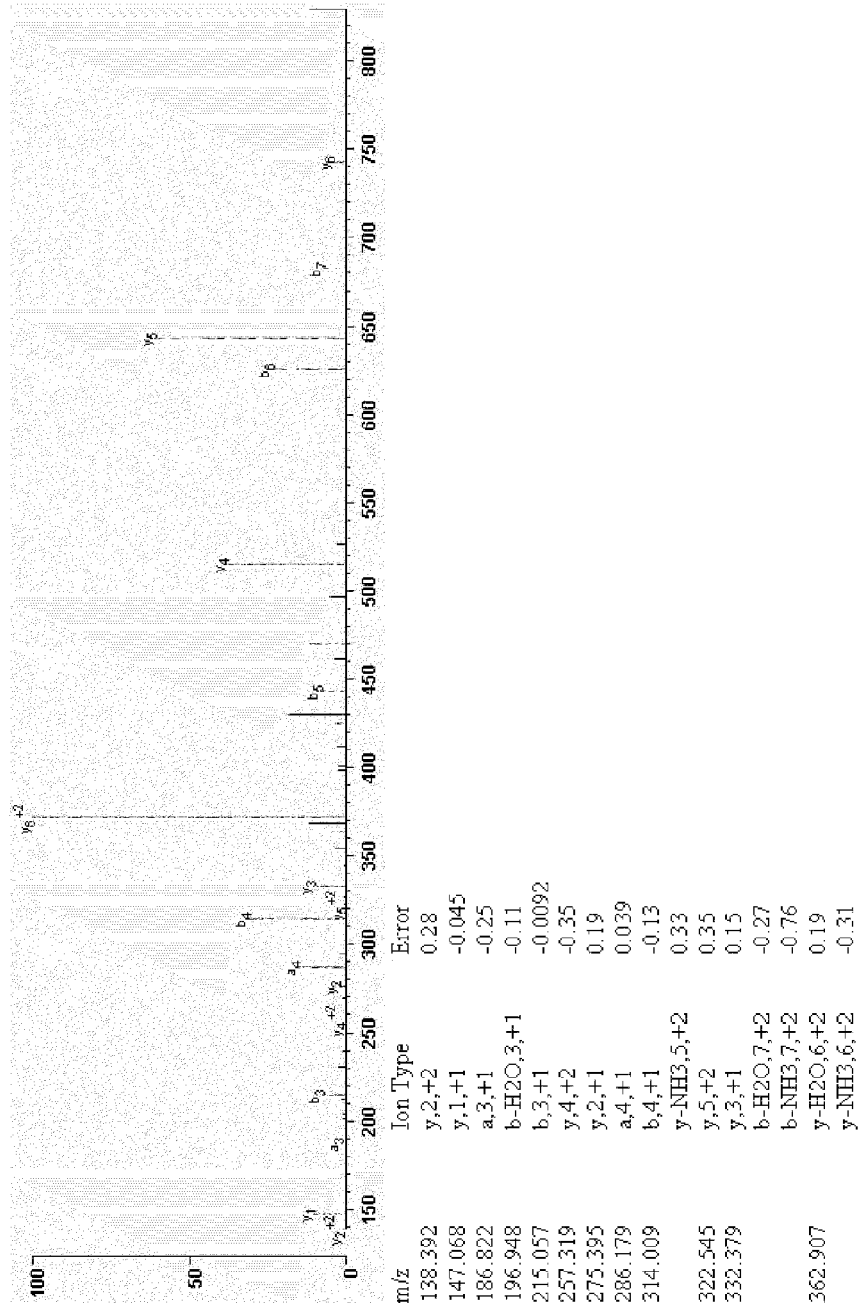
Figure 11A:
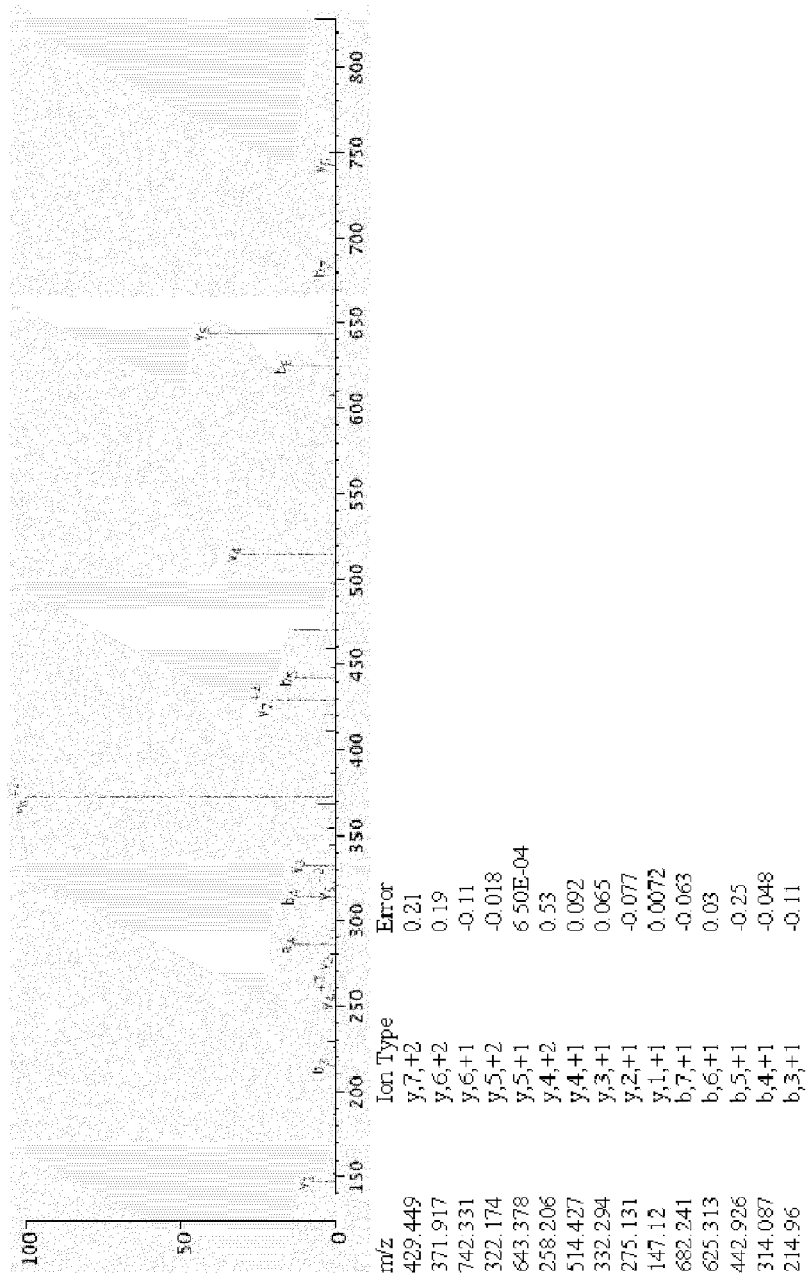
Figure 11A:
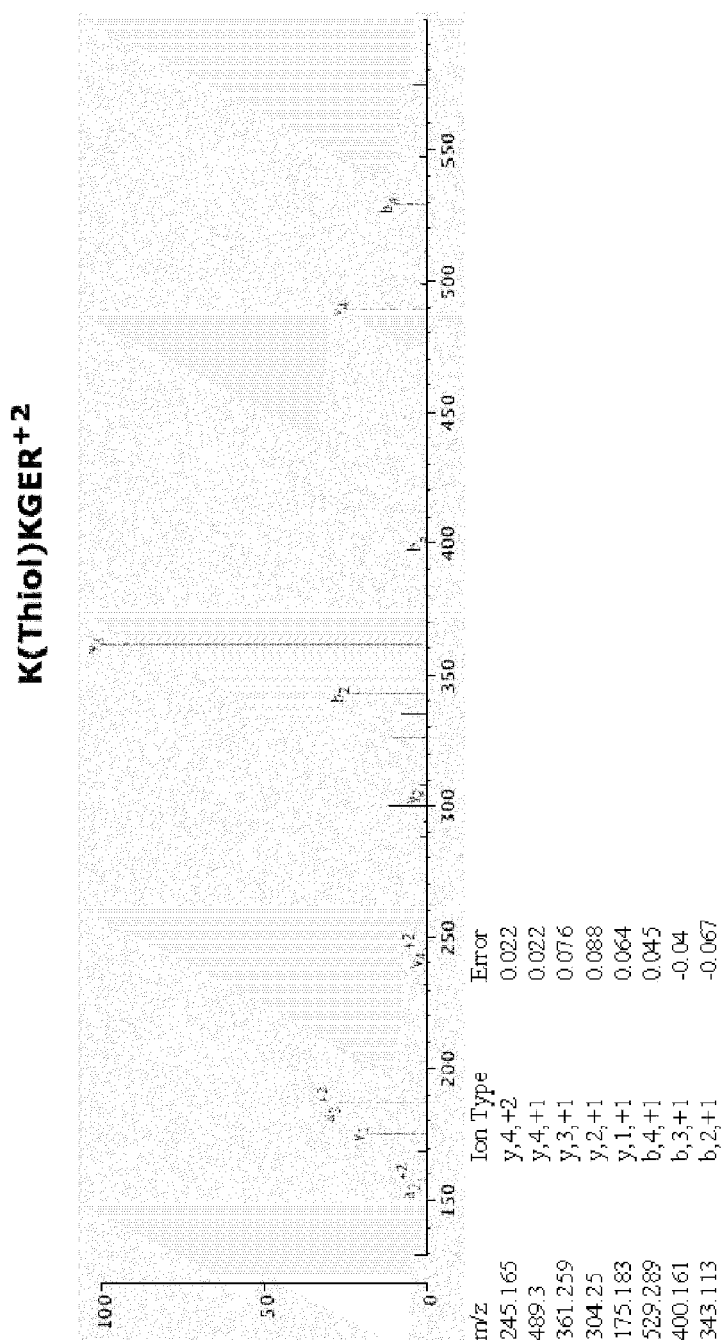
Figure 11A:
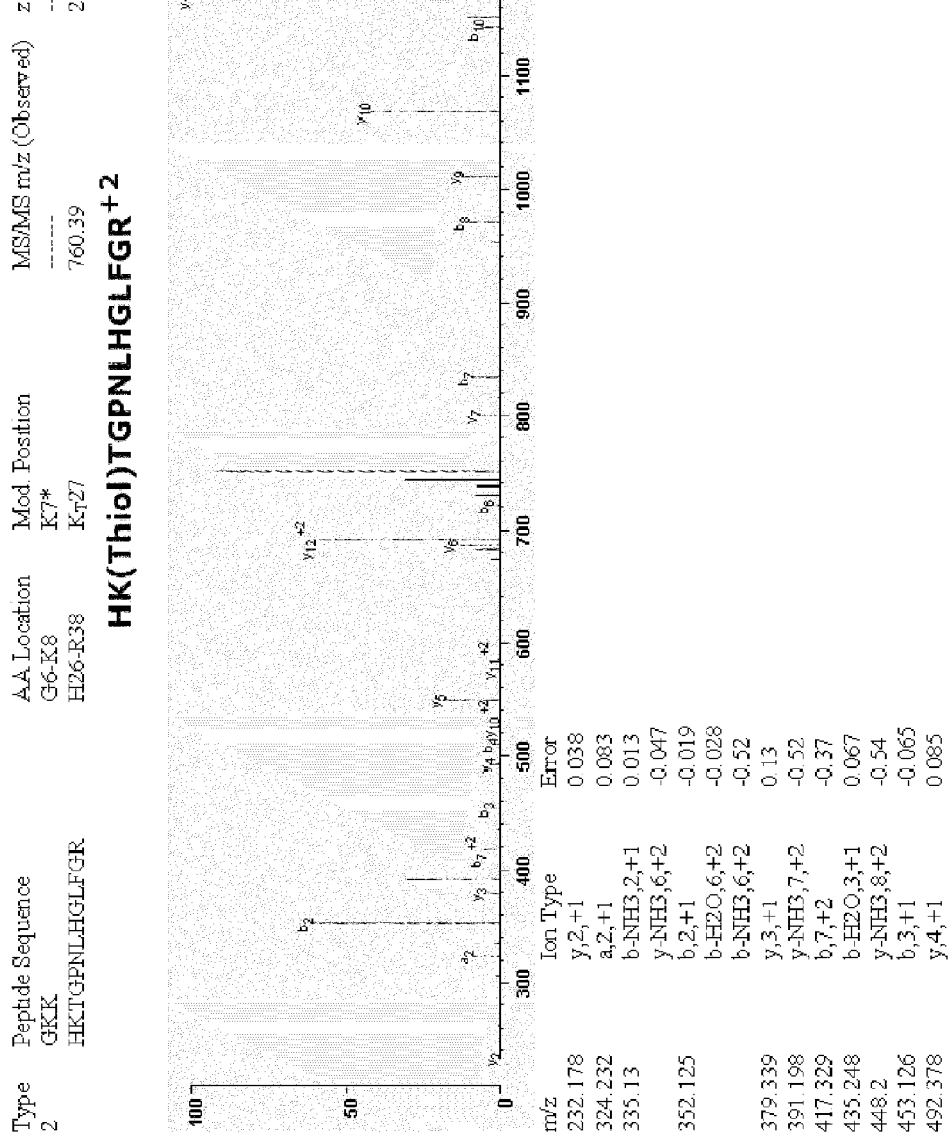
Figure 11A:
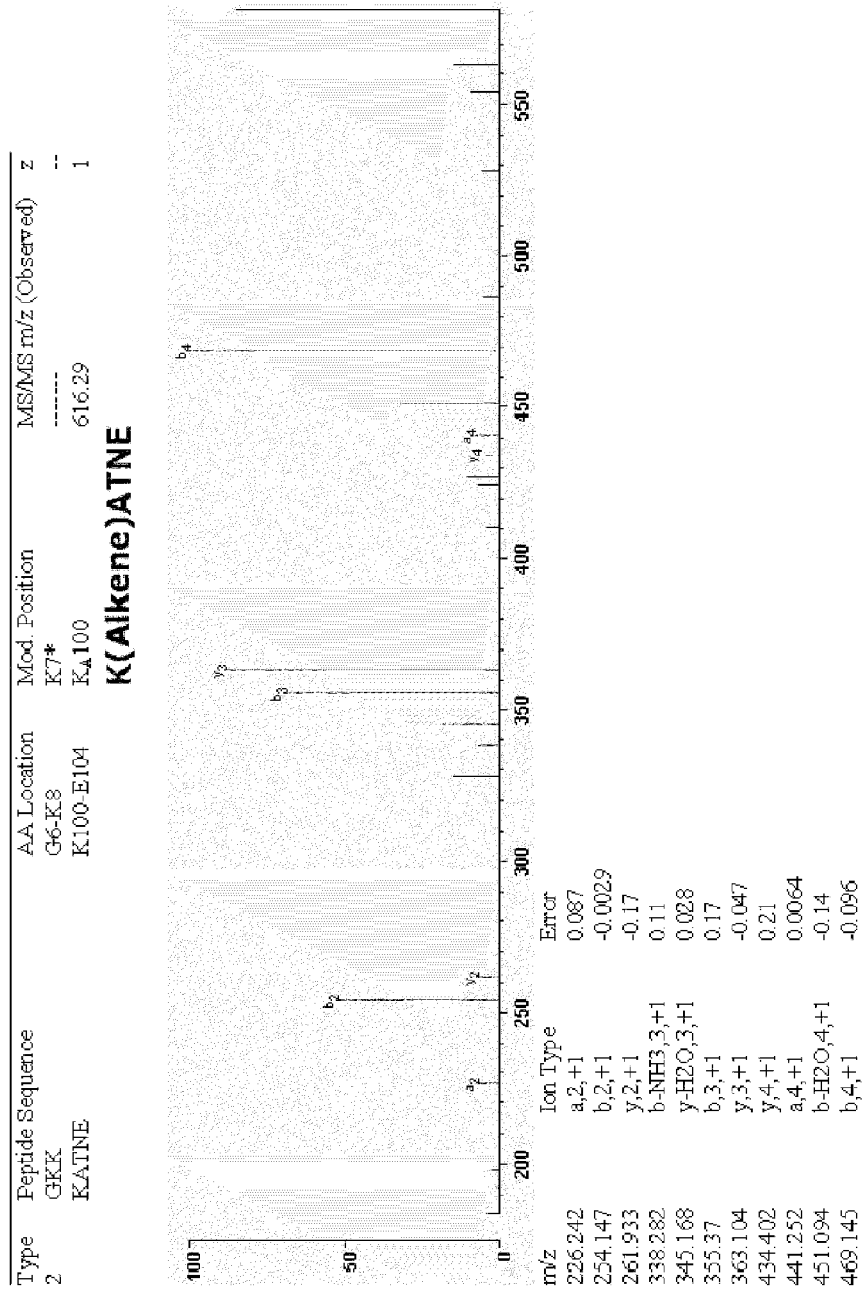
Figure 11A:
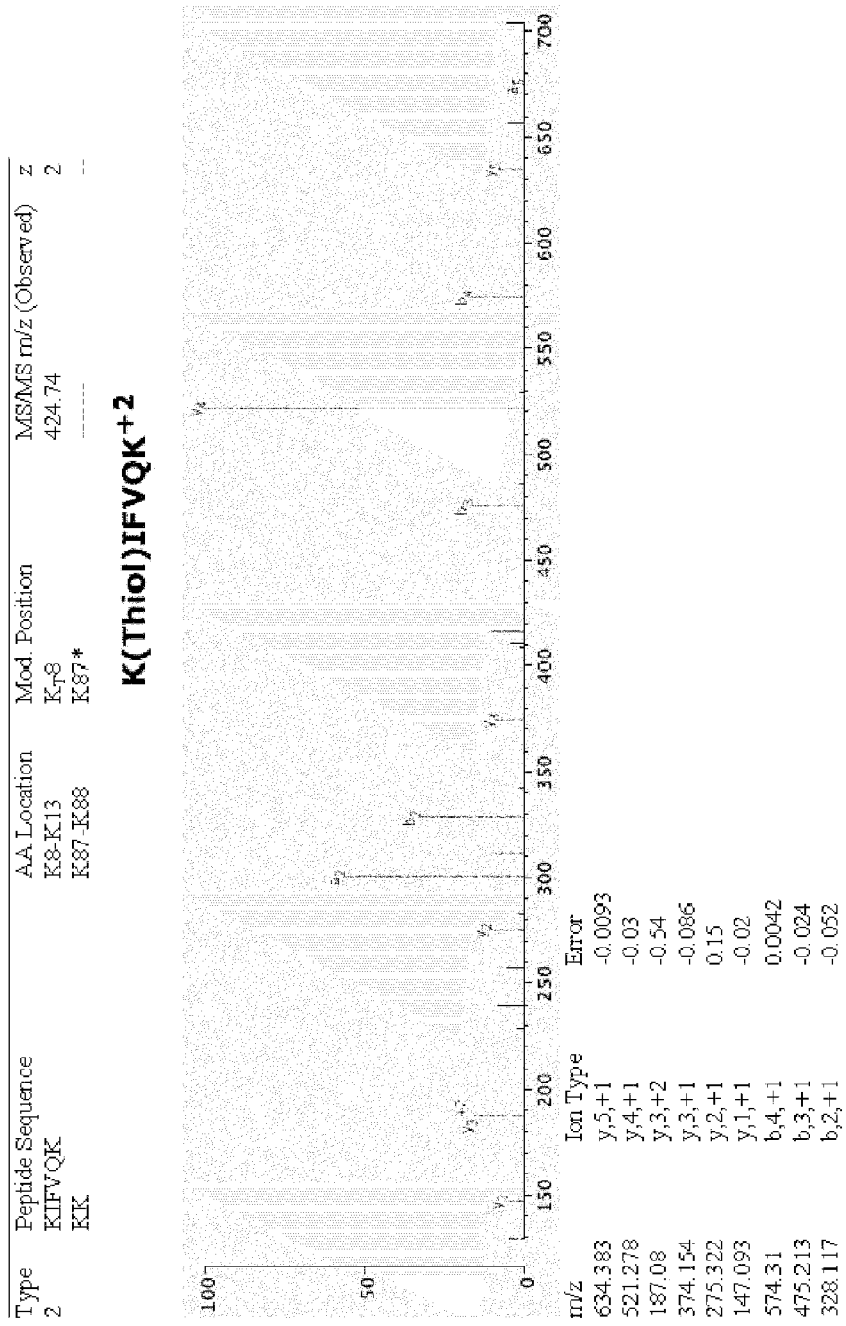
Figure 11A:
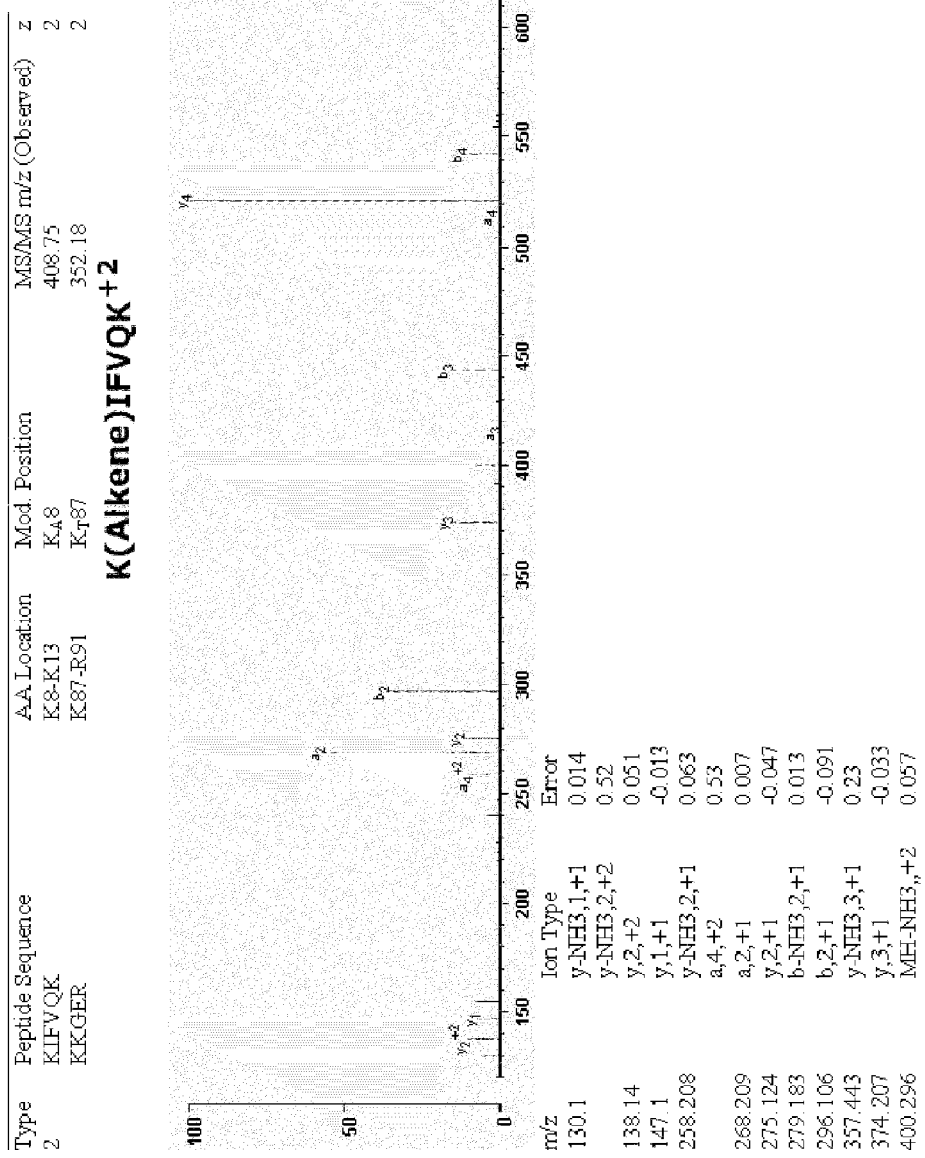
Figure 11A:
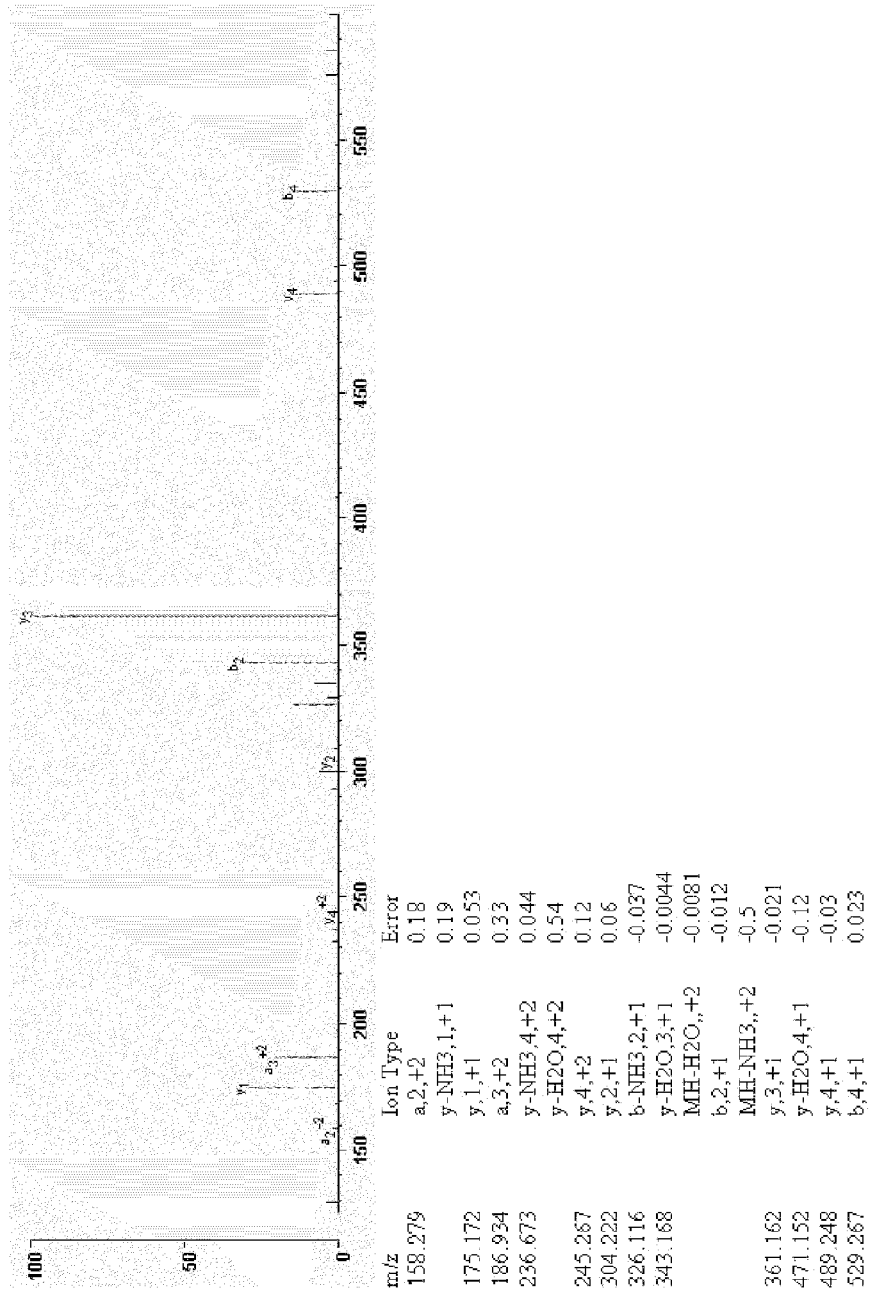
Figure 11A:
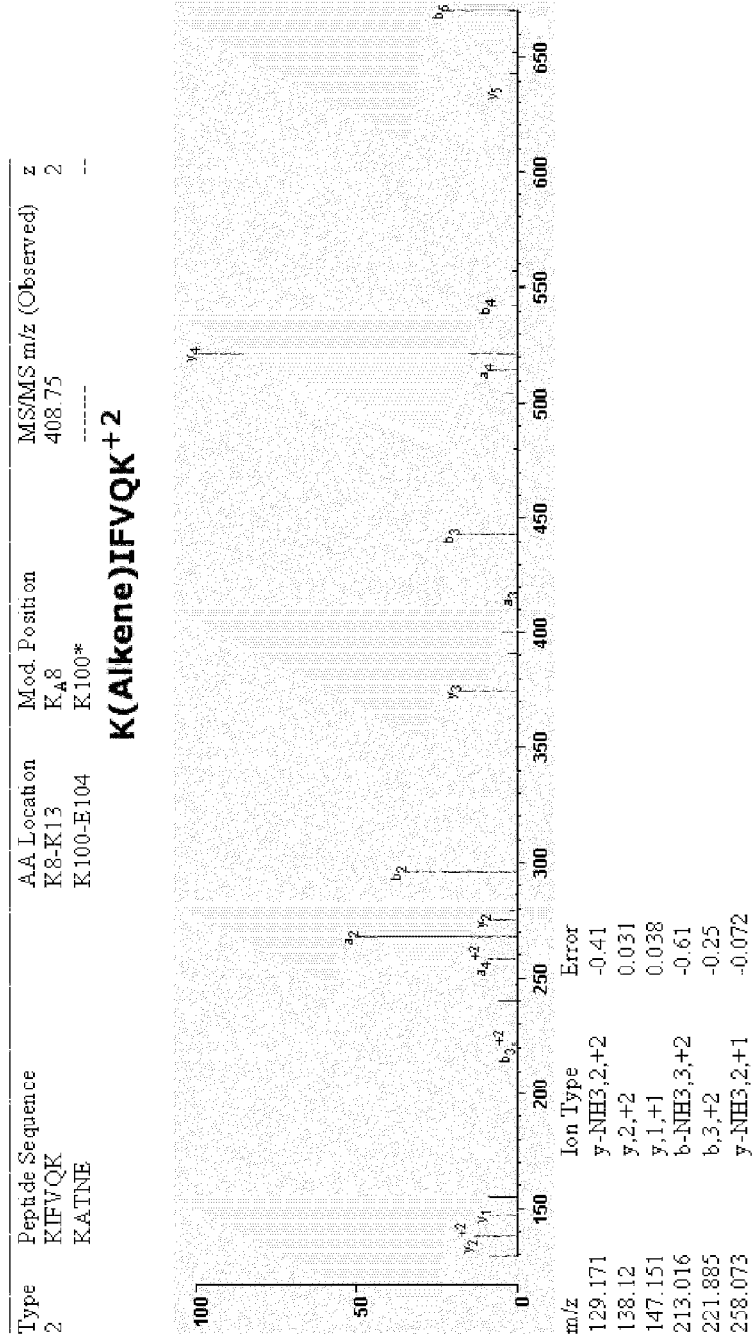
Figure 11A:
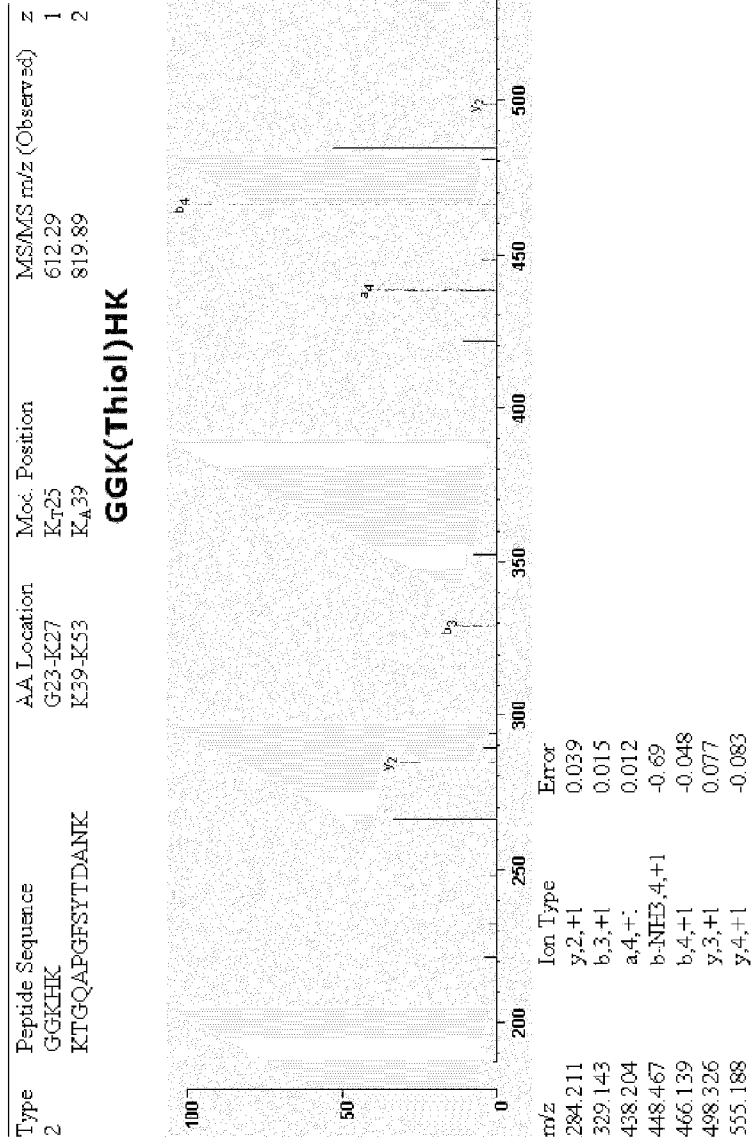
Figure 11A:
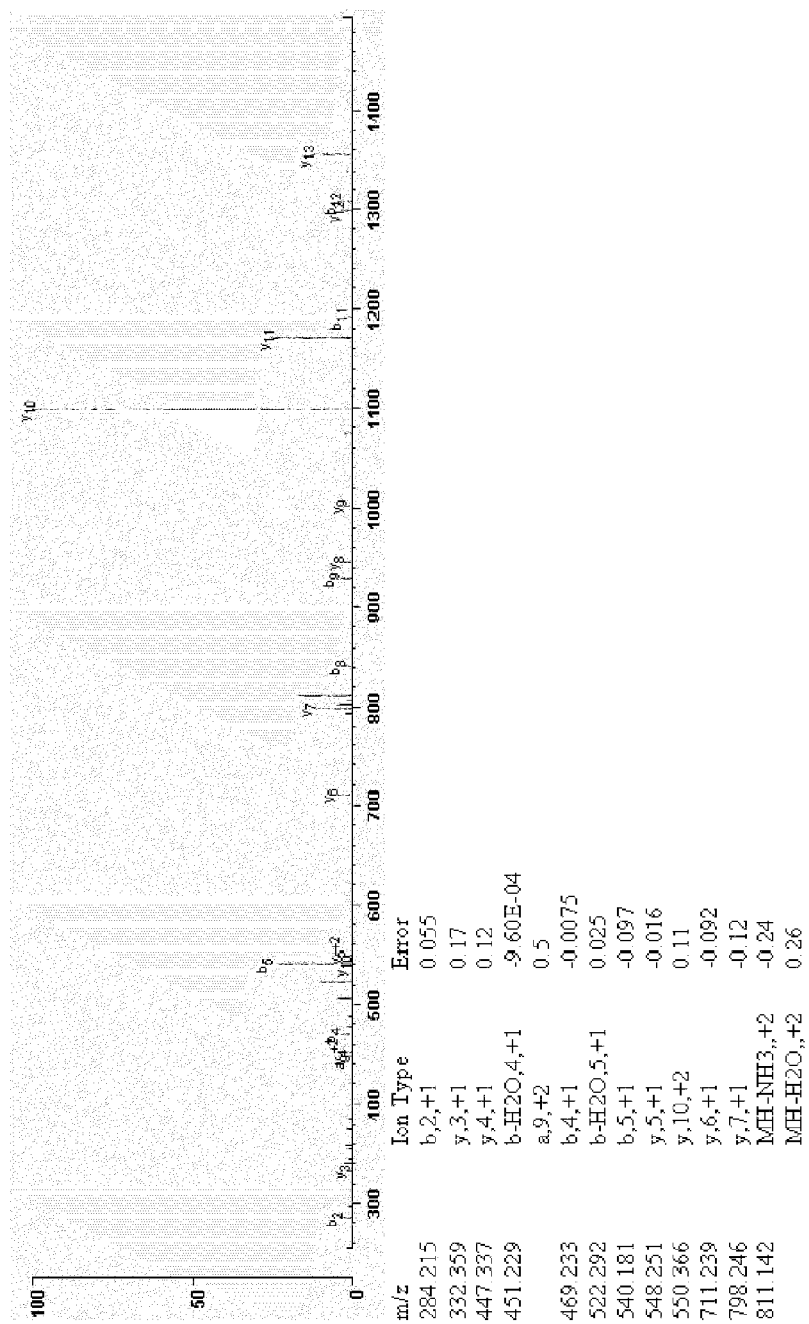
Figure 11A:
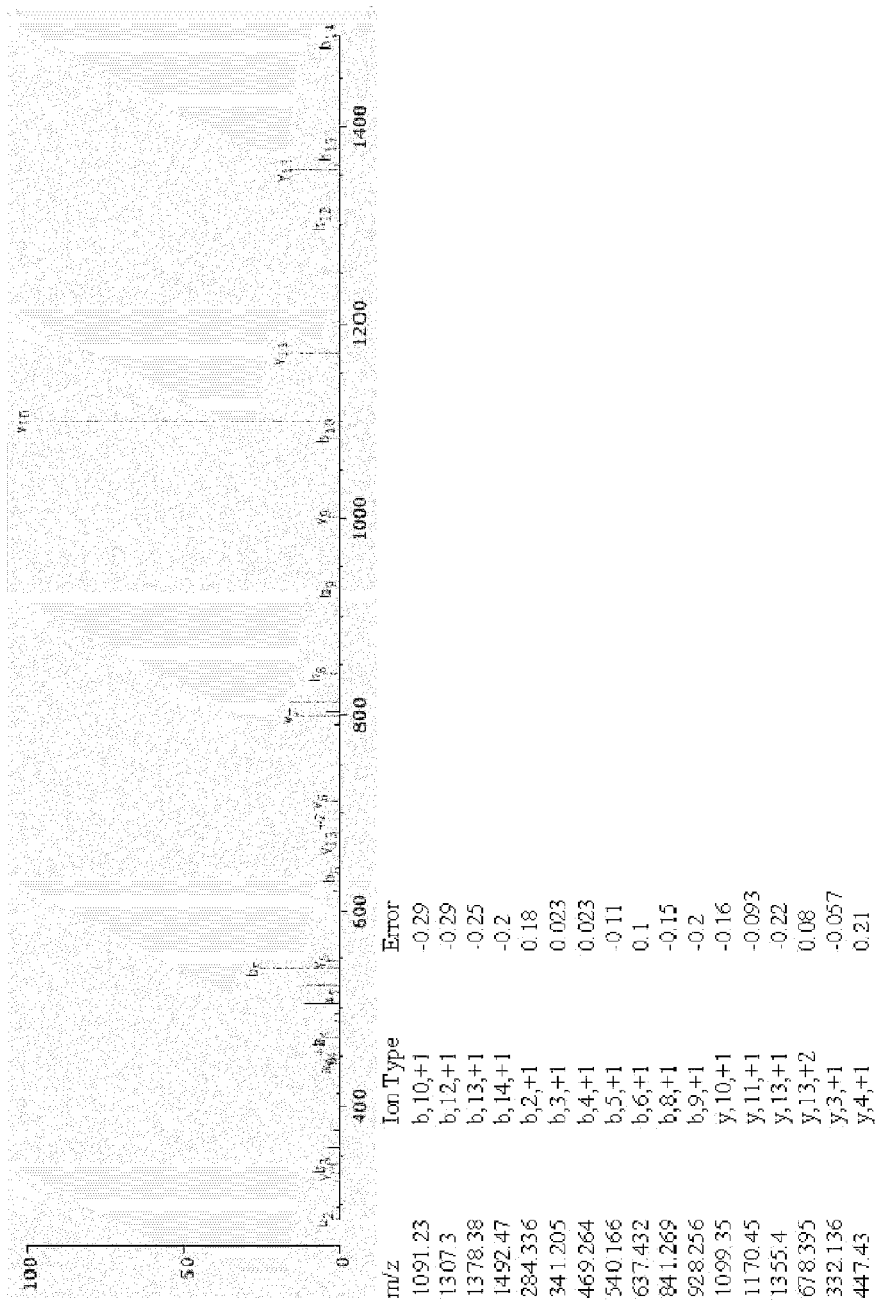
Figure 11A:
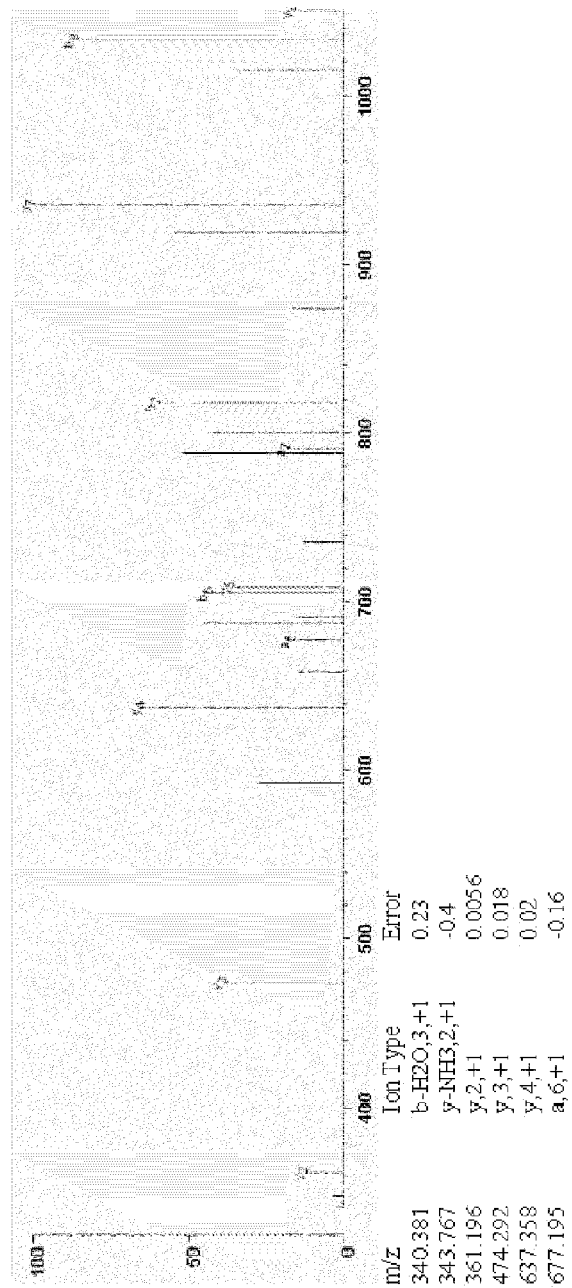
Figure 11A:
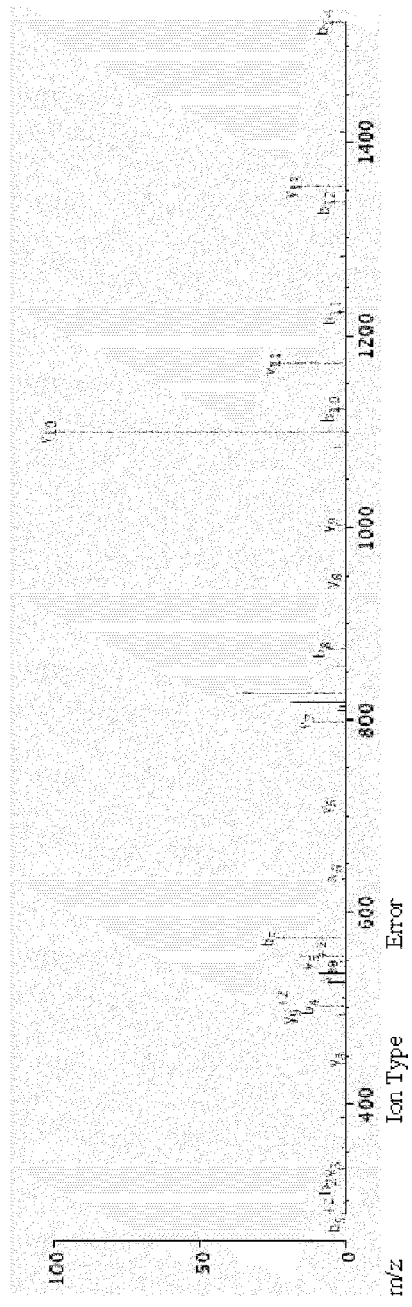
Figure 11A:
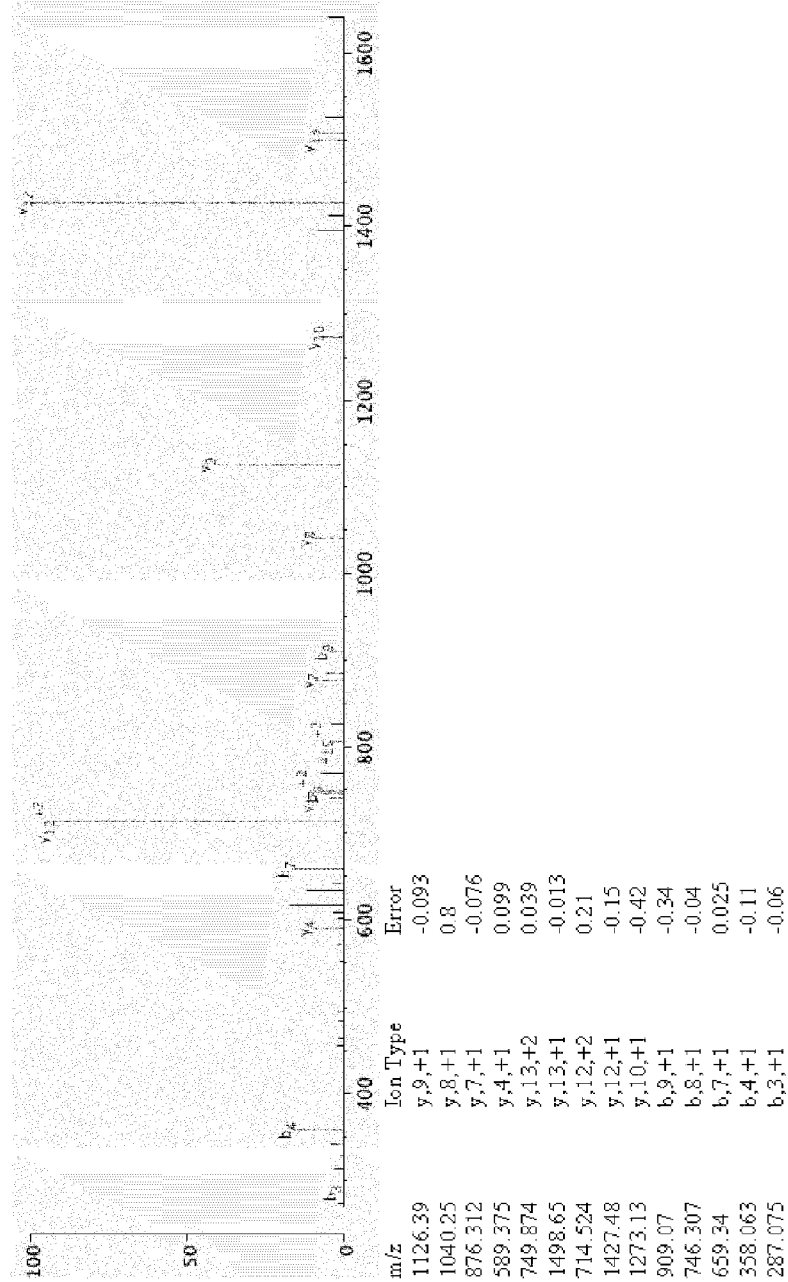
Figure 11A:
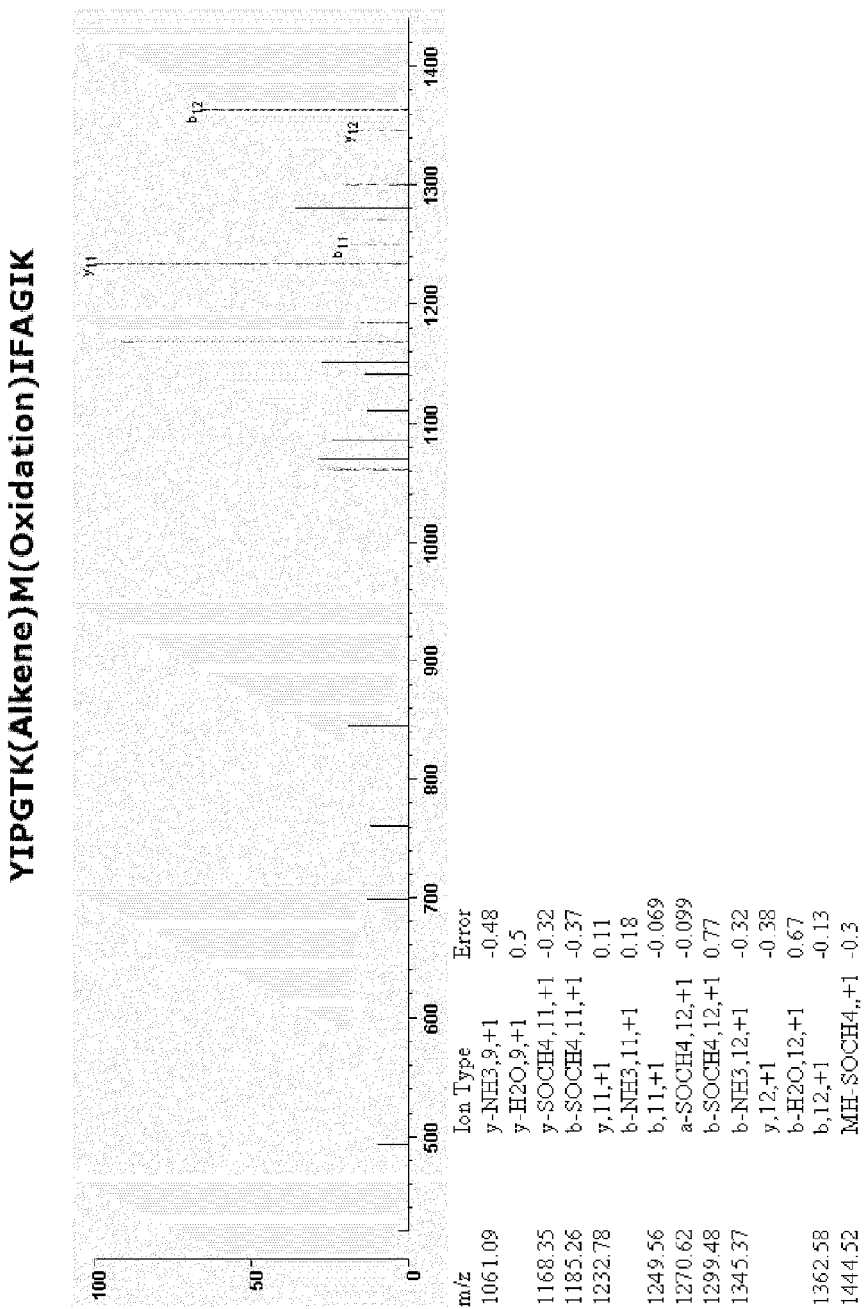
Figure 11A:
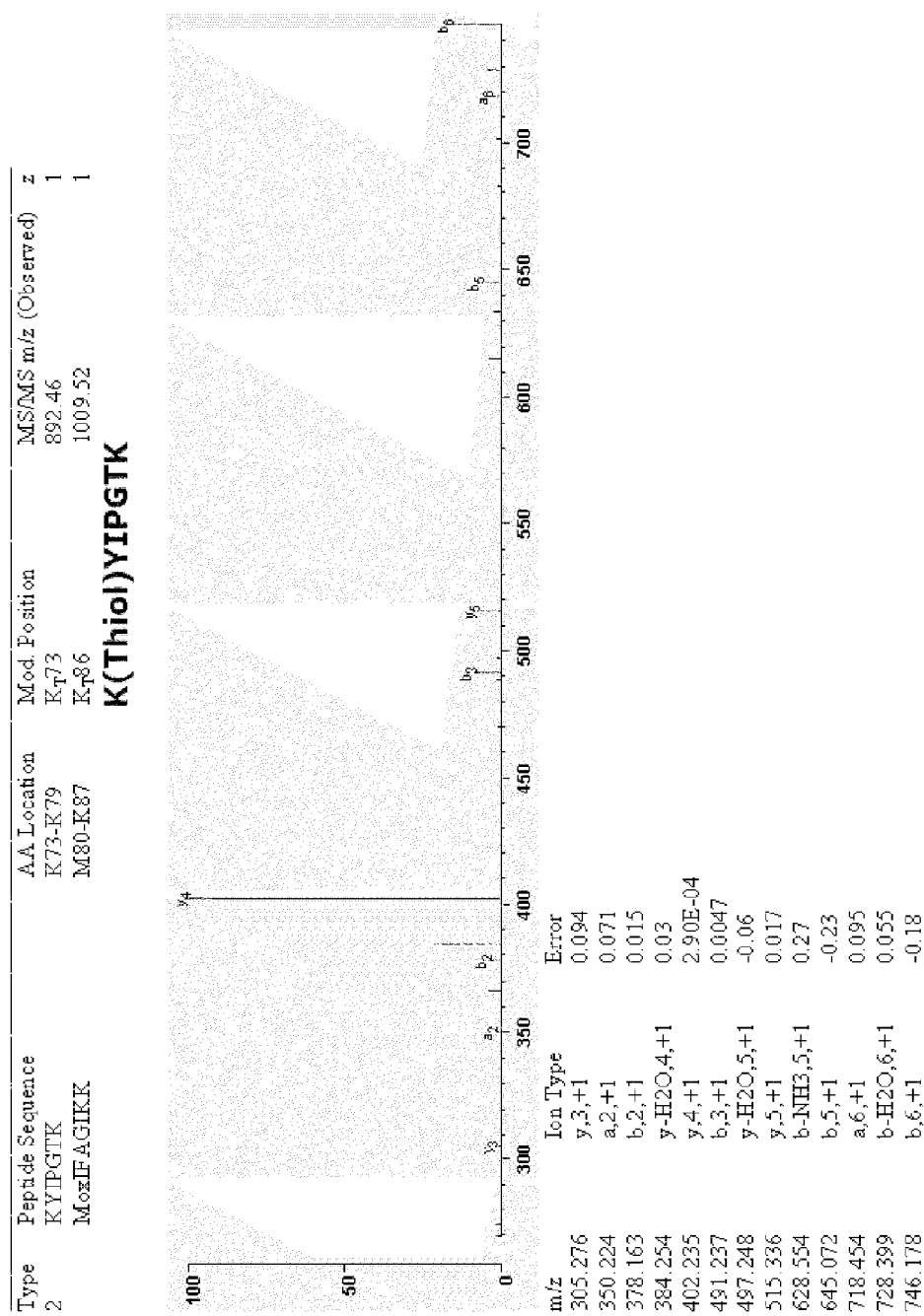
Figure 11A:
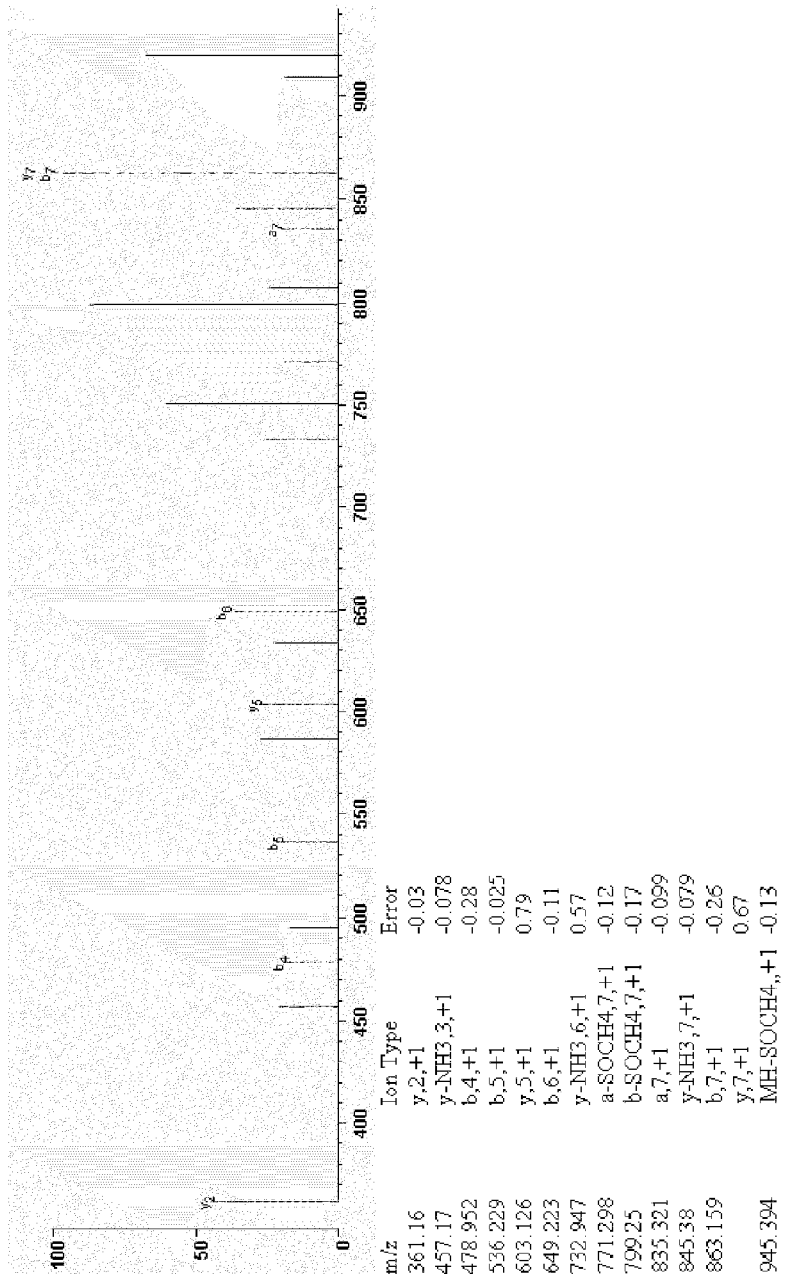
Figure 11A:
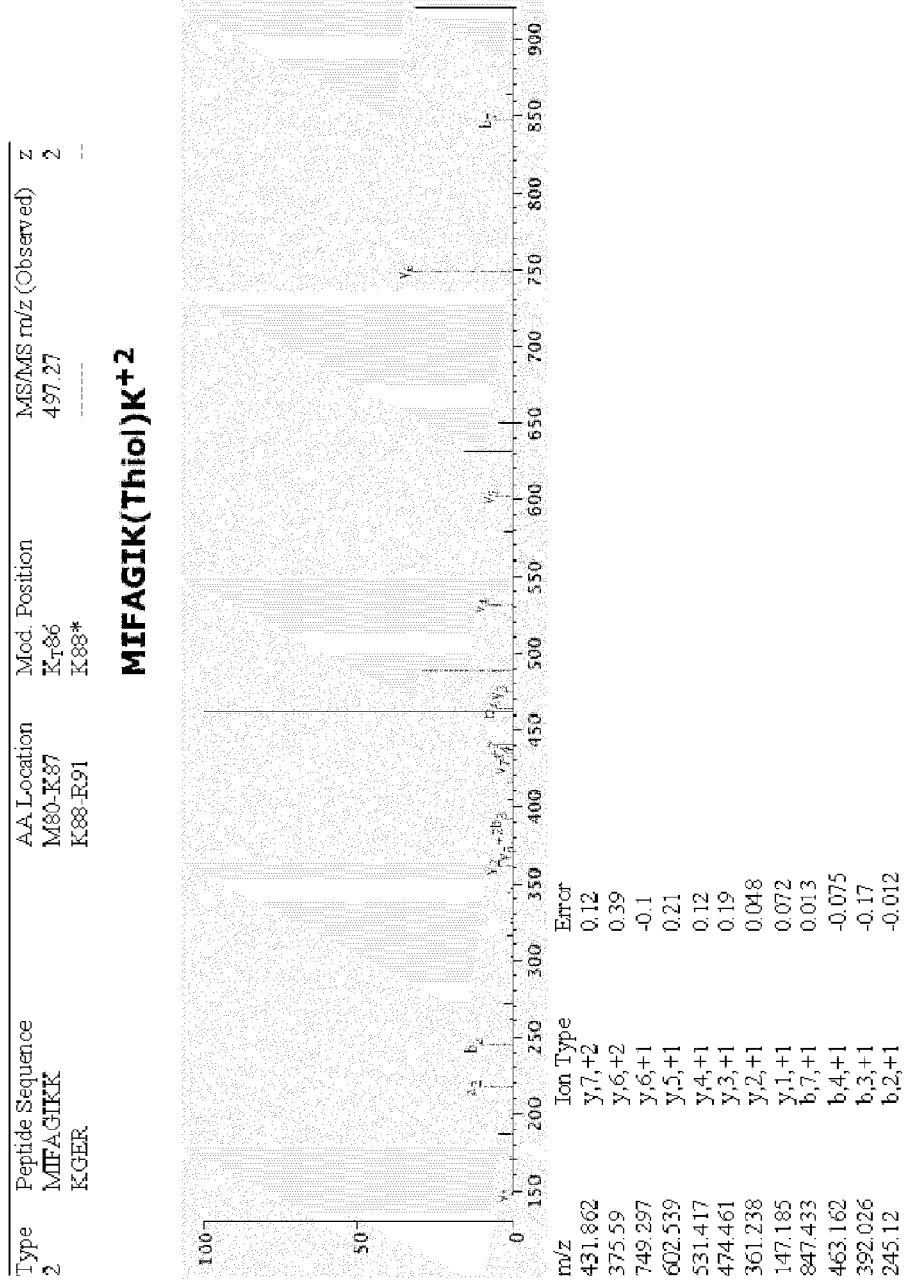
Figure 11A:
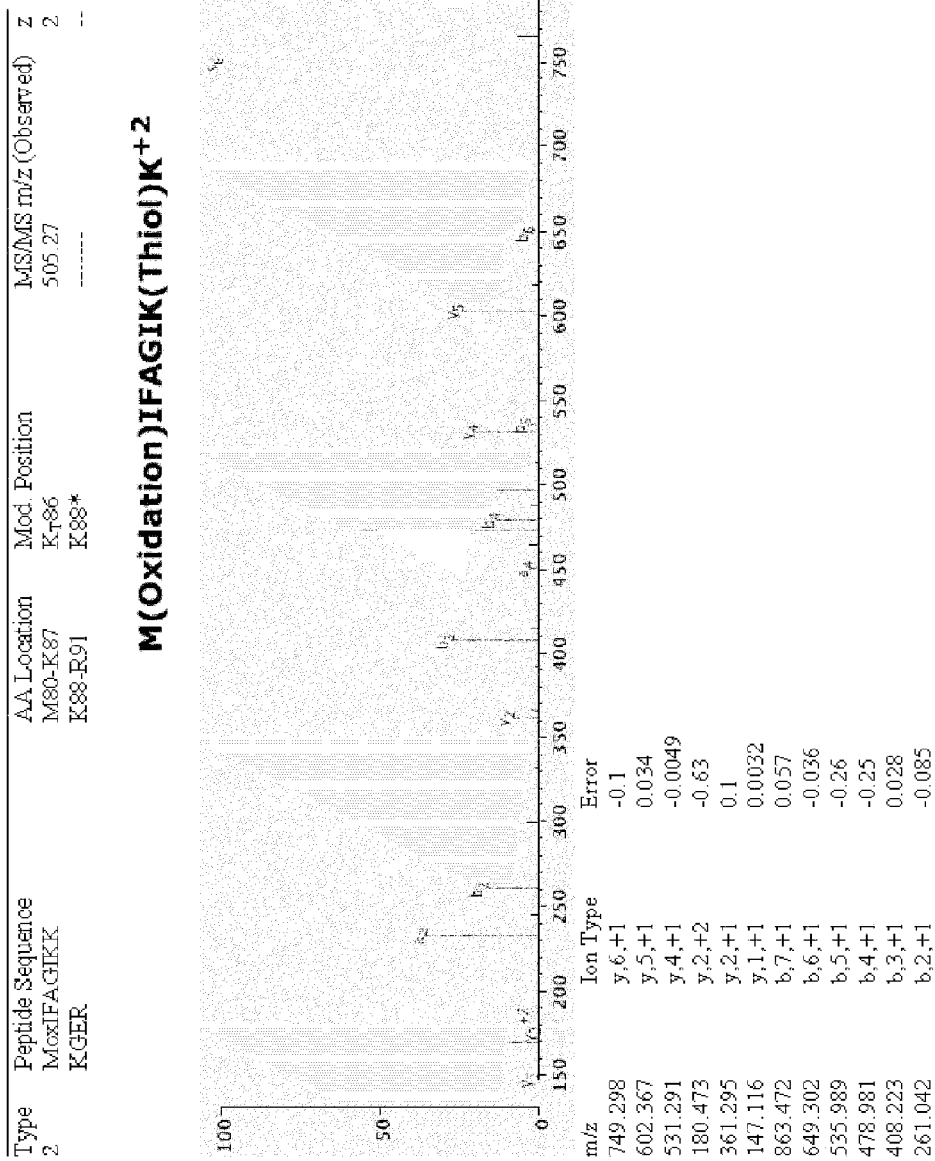
Figure 11B:
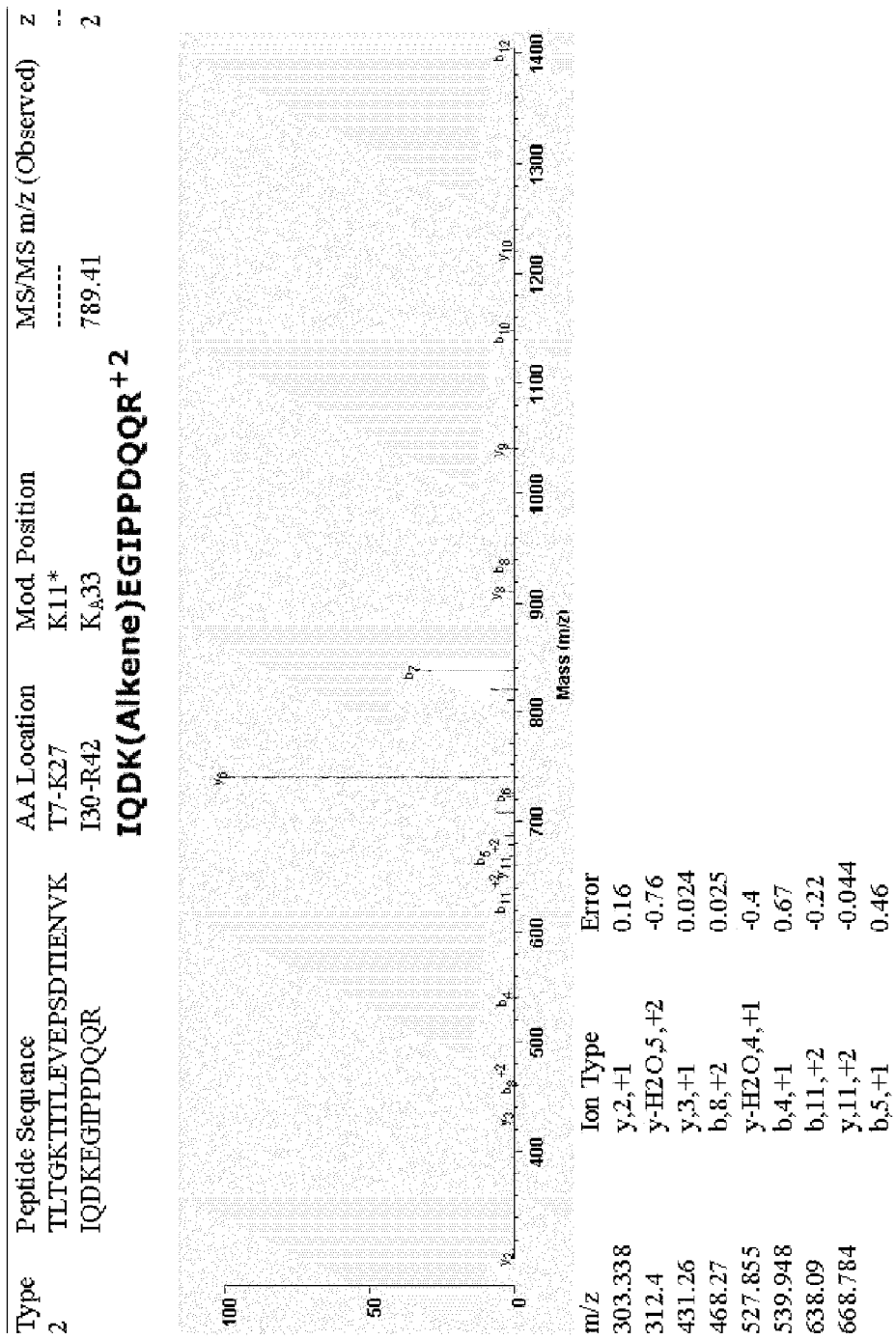
FIG. 11B is an exemplary $MS^3$ analysis of ubiquitin.
Figure 11B:
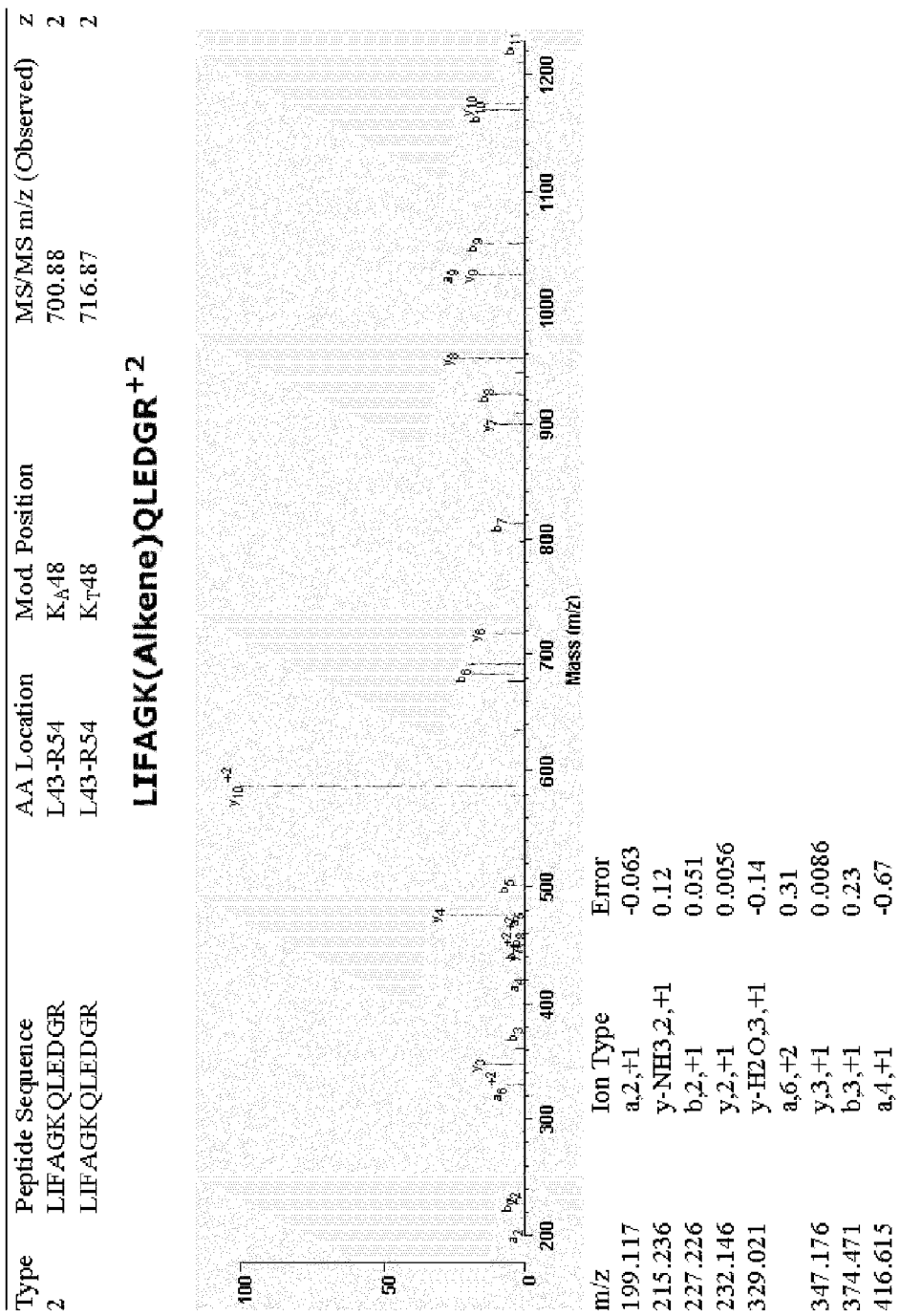
Figure 11B:
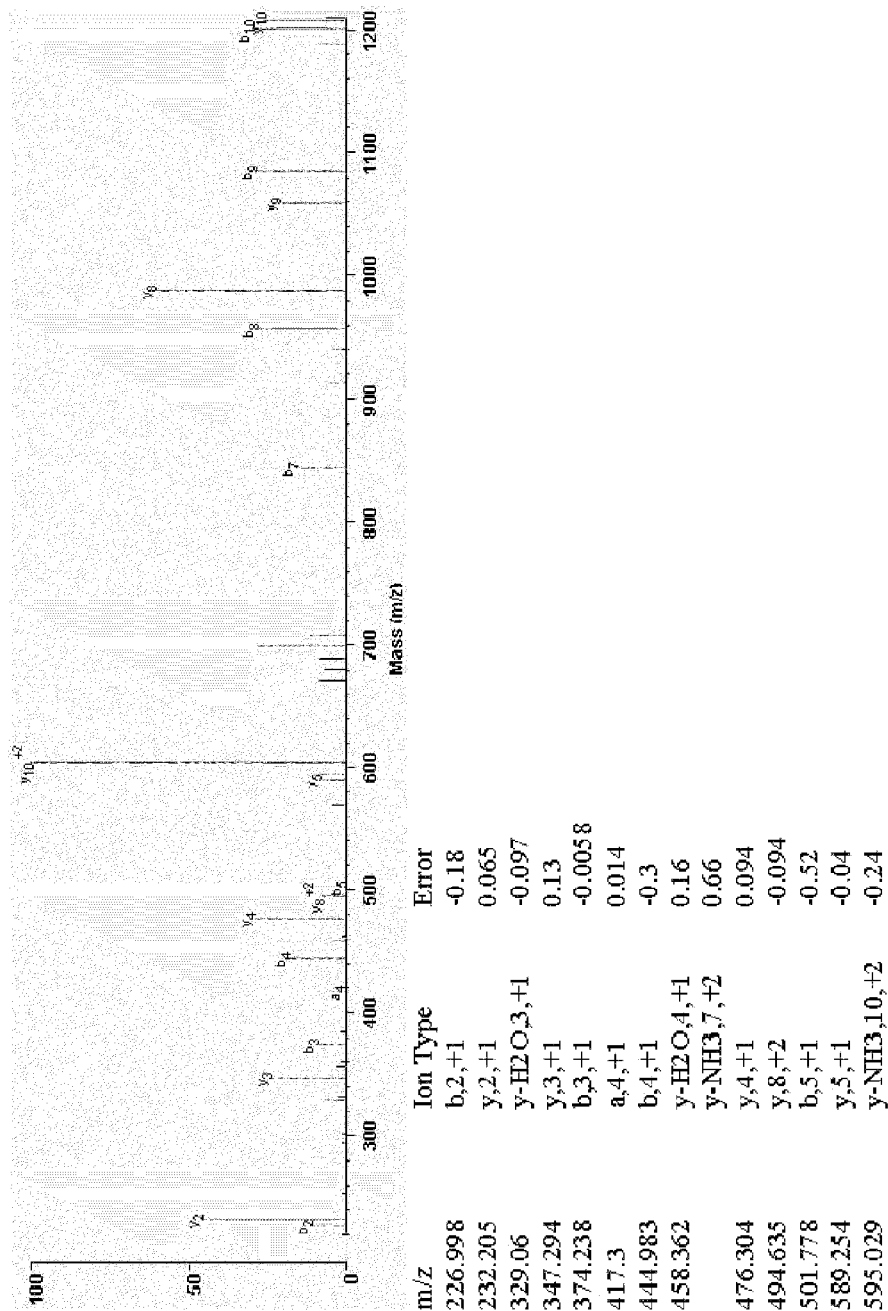
Figure 11B:
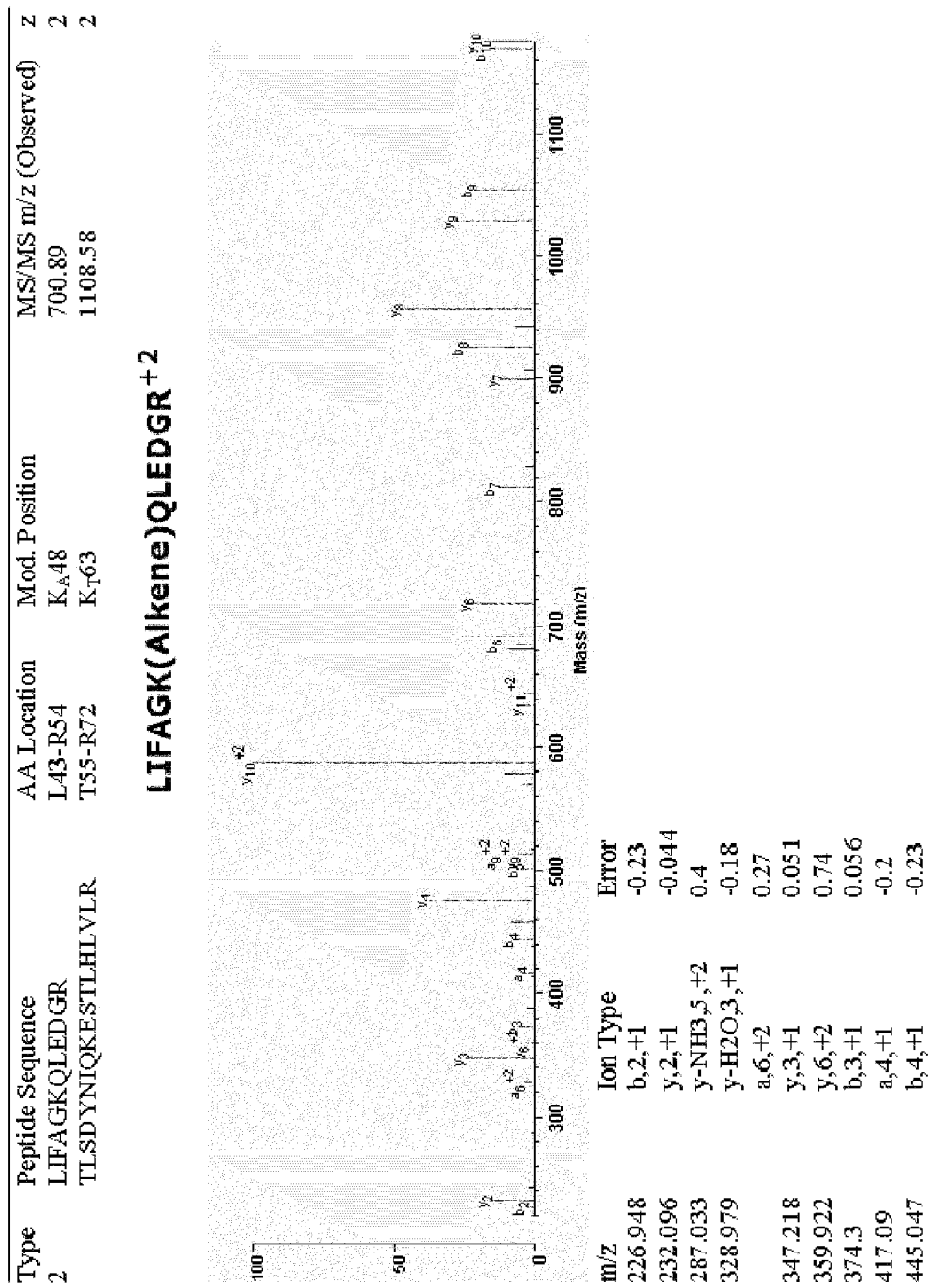
Figure 11B:
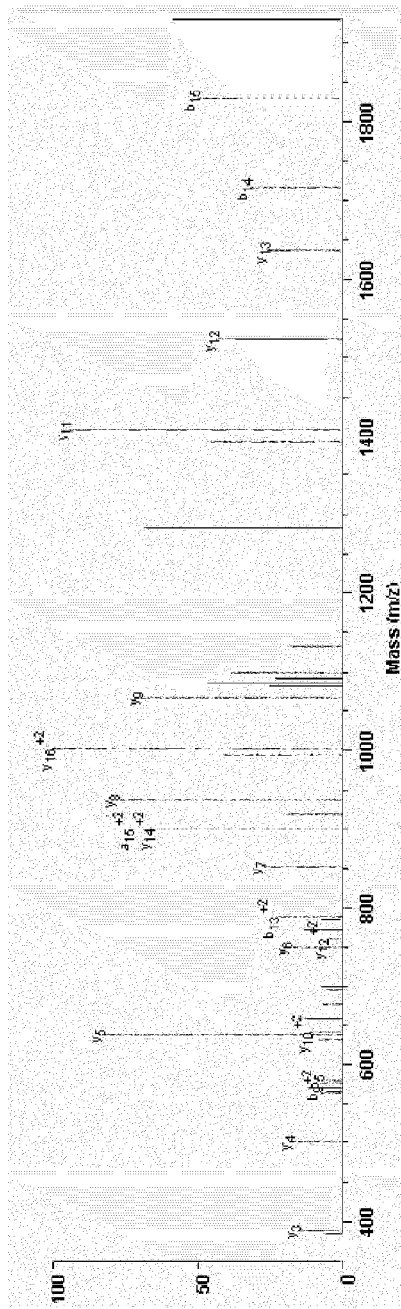

The experimentally determined structure of the yeast 20 S proteasome holocomplex was utilized (Protein Data Bank code 1RYP) to assess the cross-linked lysine pairs identified in this study. For each identified cross-link the distance between the alpha carbons was calculated and the results are summarized in TABLE 2. Considering the spacer length of DSSO and lysine side chains, the theoretical upper limit for the distance between the alpha carbon atoms of paired lysines is approximately 26 Å. The inventors' reported distances are within this upper limit, providing some evidence that the proteasome cross-links are formed in the native state. The quaternary proteasome structure is formed by four stacked seven-member rings in the order αββα. The side view and basal view of the arrangement among one set of the symmetric αβ rings and their subunits are shown in FIG. 9. The alpha carbon trace is shown for all subunits and the cross-linked lysines are shown in space fill representation. Lysines forming intra-subunit cross-links appear in blue and those forming inter-subunit cross-links appear in red. The images in FIG. 9 were generated using UCSF Chimera visualization software (Pettersen, E., Goddard, T., Huang, C., Couch, G., Greenblatt, D., Meng, E., and Ferrin, T. (2004) Ucsf Chimera—a Visualization System for Exploratory Research and Analysis. *Journal of computational chemistry* 25, 1605-1612).

DISCUSSION

The inventors have presented a novel cross-linking strategy for structural analysis of model proteins and the yeast 20 S proteasome complex by combining a newly designed MS-cleavable cross-linker DSSO with an integrated data analysis workflow. As noted above, while this discussion has centered around DSSO (shown as Compound 1 in FIG. 1), other compounds having the General Structure 2, such as Compounds 3-6 can also be used. This approach is effective and facilitates fast and accurate identification of DSSO cross-linked peptides by LC MS$^n$. The new MS-cleavable cross-linker DSSO is attractive for cross-linking studies of protein complexes for a number of reasons: 1) it can be easily synthesized and can cross-link protein complexes effectively at sub-micromolar concentrations (~1 μM); 2) it has two symmetric CID labile C—S bonds that preferentially fragment prior to peptide backbone breakage; 3) the CID-induced cleavage of inter-linked peptides is specific and independent of peptide charges and sequences; 4) DSSO cross-linked peptides can generate characteristic fragmentation patterns in MS/MS spectra that are unique to different types of cross-linked peptides for easy identification; 5) there are unique mass and charge relationships between MS/MS peptide fragment ions and their parent ions, permitting automated data processing. In comparison to existing MS-cleavable cross-linkers (Tang, X., et al.; Zhang, H., et al.; Soderblom, E. J., and Goshe, M. B. et al.; Soderblom, E. J., Bobay, B. G., et al.; and Gardner, M. W., et al.), the DSSO cross-linker can provide a specific and selective fragmentation of cross-linked peptides for identification. The fragmentation patterns of DSSO cross-linked peptides are similar to those of "fixed charge" sulfonium ion containing cross-linked model peptides developed by Lu, Y. et al. Although DSSO does not carry a fixed charge, our results have demonstrated that the preferential cleavage of C—S bond adjacent to the sulfoxide in DSSO is as effective as cleavage of the C—S bond in the sulfonium ion containing cross-linker (i.e. S-methyl 5,5'-thiodipentanoylhydroxysuccinimide) (Lu, Y. et al.). However, fragmentation of the sulfonium ion containing cross-linked peptide requires the formation of a five-membered ring with the sulfonium ion and the amide of the linker such that it is not feasible to change spacer lengths in these cross-linkers. In contrast, the simple fragmentation mechanism gives DSSO the flexibility of changing its spacer lengths to accommodate cross-linking lysines at different distances while maintaining the symmetry of the linker with easily interpretable fragmentation patterns. In addition, DSSO has better potential for studying protein interactions by in vivo cross-linking. It is well known that cross-linking study of protein complexes is extremely challenging due to the inherent limitations of current cross-linkers. With the improvement on database searching of non-cleavable inter-linked peptides, it is possible to identify cross-linked peptides of protein complexes using non-cleavable cross-linkers (Maiolica, A., et al.; and Chen, Z. A. et al.). However, this requires a special program for data interpretation and the false positive rate of identifying inter-linked sequences is higher than that of identifying single sequences. Here the inventors have demonstrated the feasibility of using novel DSSO cross-linking strategy to study the structure of the yeast 20S proteasome complex. This work represents a major advancement in structural elucidation of multi-subunit protein complexes with improved data analysis and accuracy as such application of MS-cleavable cross-linkers has not been reported before.

In addition to the design of this novel MS-cleavable linker, the inventors have developed an integrated data analysis workflow to achieve fast, easy and accurate identification of cross-linked peptides and the cross-linking sites. Identification of DSSO cross-linked peptides from complex mixtures has been accomplished with high confidence by integrating data analyses of three different datasets, MS, MS/MS and MS$^3$ data. Due to the difficulty in interpreting MS/MS spectra of unseparated inter-linked peptides, many of previously reported inter-linked products were determined only based on parent masses. In contrast, all of the inter-linked peptides of cytochrome c, ubiquitin and the yeast 20 S proteasome complex have been identified in this work with three lines of evidence including characteristic fragmentation pairs (Link-Finder), peptide sequence determination by MS$^3$ sequencing (Batch-Tag), and mass mapping (MS-Bridge). This procedure permits the identification of cross-linked peptides with high accuracy, reliability and speed. It is important to note that existing database search programs can be easily adapted for analyzing DSSO cross-linked peptides, thus a broad application of the DSSO-based cross-linking strategy is foreseeable. Furthermore, cross-linked peptides of cytochrome c with two links can be identified, suggesting the capability of the new cross-linking strategy for identifying more complex cross-linked products.

Cross-linking/mass spectrometry has been previously attempted to study the yeast 20S proteasome complex using Ru(II)(bpy)$^{2+/3}$ tris(2,2'-ipyridyl)ruthenium (II) dication)/ammonium persulfate/light-mediated cross-linking (Denison, C., and Kodadek, T. (2004) Toward a General Chemical Method for Rapidly Mapping Multi-Protein Complexes. *J Proteome Res* 3, 417-425), in which multiple subunit interconnectivity has been determined based on MS identification of co-migrated subunits by SDS-PAGE after cross-linking. No cross-linked peptides were identified due to complicated chemistry of the radical based cross-linking reaction. Therefore the inventors' work describes the first successful use of a cross-linking/mass spectrometry strategy to determine inter-subunit and intra-subunit interaction interfaces of the yeast 20 S proteasome complex. Although only 13 inter-linked peptides of the yeast 20 S proteasome have been identified and reported here, this work presents the first step toward full characterization of proteasome structures using cross-linking/mass spectrometry in the future. The feasibility of using the DSSO-based cross-linking strategy to identify cross-linked peptides of a large protein complex at 1 μM or less concentration is very significant and of great promise to structural studies of protein complexes since purifying protein complexes at high concentrations is technically challenging.

During LC MS$^n$ analysis using LTQ-Orbitrap XL MS, collision energy cannot be adjusted on the fly to account for differences in peptide charge states, therefore compromised collision energy is set during the entire LC MS$^n$ run. Thus there exists a possibility that the collision energy may be too high for the highly charged ions while too low for peptides with lower charges. Future improvement on charge selection and energy adjustment during LC MS$^n$ data acquisition may be needed to further enhance the quality of the results. Additionally, optimized peptide separation prior to LC MS$^n$ analysis will be necessary to improve the dynamic range of peptide analysis and allow the detection of low abundance cross-linked peptides. Moreover, refinement of the Link-Finder program is needed to improve the identification of intra-linked peptides. Lastly, the addition of an affinity tag to the sulfoxide containing cross-linker will improve detection of cross-linked peptides, which will be the subject of our future study.

In summary, the inventors have developed a new MS-cleavable cross-linker family of compounds, including DSSO that are applicable for model peptides, proteins and a multi-subunit protein complex. The unique MS features of DSSO cross-linked peptides together with our integrated data analysis workflow for analyzing LC MS$^n$ data greatly reduce the time spent identifying cross-linked peptides. Given its simplicity, speed and accuracy, the inventors believe that this cross-linking strategy will have a broad application in elucidating structures of proteins and protein complexes in the future.

Although embodiments of the present invention have been described in detail herein in connection with certain exemplary embodiments, it will be understood that the invention is not limited to the disclosed exemplary embodiments, but, on the contrary, is intended to cover various modifications and equivalent arrangements. The invention is limited only by the appended claims and their equivalents.

What is claimed is:

1. An isolated MS-cleavable cross-linker for proteins and protein complexes, the cross-linker having two symmetric collision-induced dissociation (CID) cleavable sites and the formula:

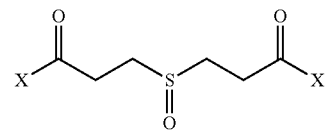

where X is selected from the group consisting of:

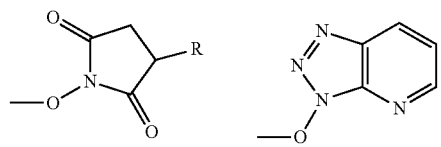

-continued

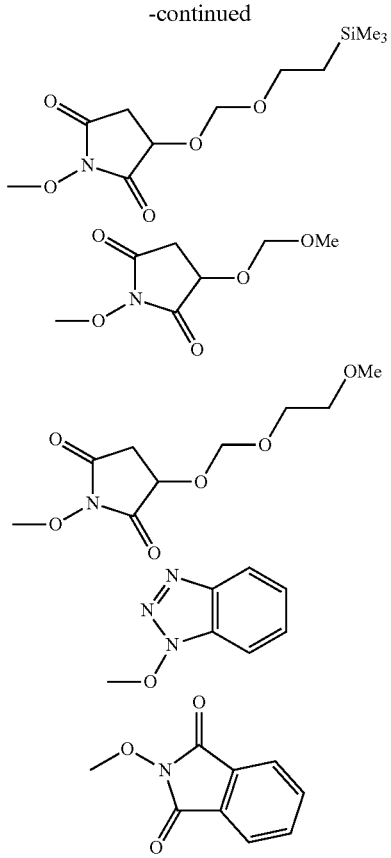

wherein R is H, methyl or ethyl.

2. The isolated MS-cleavable cross-linker of claim 1, having the structure:

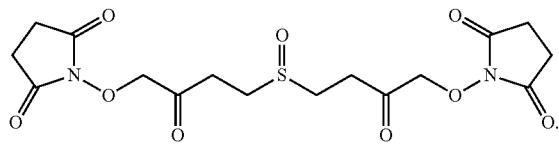 [SMILES: O=C(CCS(=O)CCC(=O)CON1C(=O)CCC1=O)CON1C(=O)CCC1=O]

3. A method for mapping protein-protein interactions of protein complexes, the method comprising:
providing the isolated MS-cleavable cross-linker of claim 1;
forming a cross-linked protein complex by cross-linking proteins with the MS-cleavable cross-linker;
forming protein and/or peptide fragments that are chemically bound to the MS-cleavable cross-linker by digesting the cross-linked protein complex with an enzyme; and
using mass spectrometry (MS) and MS" to identify the protein and/or peptide fragments.

4. A method for integrated data analysis workflow for identification of cross-linked peptides, the method comprising:
cross-linking peptides with an isolated MS-cleavable cross-linker of claim 1;
performing mass spectrometry on the cross-linked peptides to obtain MS data, MS/MS data, and $MS^3$ data;
identifying the MS/MS data comprising characteristic fragmentation profiles of MS-cleavable cross-linked peptides to obtain an MS/MS result comprising a list of parent ions corresponding to cross-linked peptide candidates;
mass mapping the MS data using the list of parent ions corresponding to the cross-linked peptide candidates and the MS-cleavable cross-linker against known protein sequences to obtain an MS result;
peptide sequencing the cross-linked peptides using the $MS^3$ data obtain an $MS^3$ result; and
integrating the MS result, the MS/MS result, and $MS^3$ result to identify at least one of the cross-linked peptides.

5. The method of claim 4, wherein the MS-cleavable cross-linker is

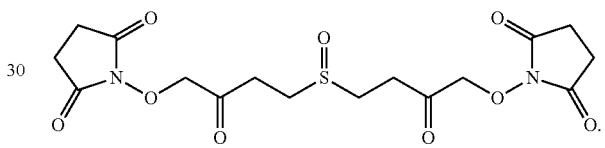

6. The method of claim 4, wherein the MS data is obtained in fourier transform (FT) mode.

7. The method of claim 4, wherein the MS/MS data is obtained in fourier transform (FT) mode.

8. The method of claim 4, wherein the $MS^3$ data is obtained using a linear trap quadrupole (LTQ).

9. The method of claim 4, further comprising reformatting the $MS^3$ data such that data from $MS^3$ fragment ions is linked to data from MS/MS parent ions.

10. The method of claim 4, wherein performing mass spectrometry on the cross-linked peptides to obtain the MS data, the MS/MS data, and the $MS^3$ data comprises:
obtaining an MS spectrum;
obtaining an MS/MS spectrum;
obtaining an $MS^3$ spectrum;
extracting the MS data from the MS spectrum;
extracting the MS/MS data from MS/MS spectrum; and
extracting the $MS^3$ data from the $MS^3$ spectrum.

* * * * *